United States Patent
Rich et al.

(10) Patent No.: US 11,969,424 B2
(45) Date of Patent: *Apr. 30, 2024

(54) LEVOSIMENDAN FOR TREATING PULMONARY HYPERTENSION WITH HEART FAILURE WITH PRESERVED EJECTION FRACTION (PH-HFpEF)

(71) Applicant: Tenax Therapeutics, Inc., Chapel Hill, NC (US)

(72) Inventors: Stuart Rich, Skokie, IL (US); Douglas Randall, Wake Forest, NC (US); Douglas Hay, Ottsville, PA (US)

(73) Assignee: TENAX THERAPEUTICS, INC., Chapel Hill, NC (US)

( * ) Notice: Subject to any disclaimer, the term of this patent is extended or adjusted under 35 U.S.C. 154(b) by 330 days.

This patent is subject to a terminal disclaimer.

(21) Appl. No.: 17/122,921

(22) Filed: Dec. 15, 2020

(65) Prior Publication Data

US 2021/0177840 A1 Jun. 17, 2021

Related U.S. Application Data

(60) Provisional application No. 63/064,671, filed on Aug. 12, 2020, provisional application No. 63/033,773, filed on Jun. 2, 2020, provisional application No. 62/988,720, filed on Mar. 12, 2020, provisional application No. 62/967,920, filed on Jan. 30, 2020, provisional application No. 62/948,735, filed on Dec. 16, 2019.

(51) Int. Cl.
| | | |
|---|---|---|
| A61K 31/50 | (2006.01) |
| A61K 9/00 | (2006.01) |
| A61K 31/216 | (2006.01) |
| A61K 31/41 | (2006.01) |
| A61K 31/495 | (2006.01) |
| A61K 31/502 | (2006.01) |
| A61K 31/55 | (2006.01) |
| A61K 31/7048 | (2006.01) |
| A61K 38/22 | (2006.01) |
| A61K 45/06 | (2006.01) |
| A61K 47/02 | (2006.01) |
| A61K 47/10 | (2017.01) |
| A61K 47/12 | (2006.01) |
| A61K 47/26 | (2006.01) |
| A61K 47/32 | (2006.01) |
| A61K 47/40 | (2006.01) |
| A61P 9/04 | (2006.01) |
| A61P 9/12 | (2006.01) |

(52) U.S. Cl.
CPC ............ *A61K 31/50* (2013.01); *A61K 9/0019* (2013.01); *A61K 9/0053* (2013.01); *A61K 31/216* (2013.01); *A61K 31/41* (2013.01); *A61K 31/495* (2013.01); *A61K 31/502* (2013.01); *A61K 31/55* (2013.01); *A61K 31/7048* (2013.01); *A61K 38/2221* (2013.01); *A61K 38/2242* (2013.01); *A61K 45/06* (2013.01); *A61K 47/02* (2013.01); *A61K 47/10* (2013.01); *A61K 47/12* (2013.01); *A61K 47/26* (2013.01); *A61K 47/32* (2013.01); *A61K 47/40* (2013.01); *A61P 9/04* (2018.01); *A61P 9/12* (2018.01)

(58) Field of Classification Search
CPC .. A61K 2300/00; A61K 31/216; A61K 31/41; A61K 31/495; A61K 31/50; A61K 31/502; A61K 31/55; A61K 31/7048; A61K 38/2221; A61K 38/2242; A61K 45/06; A61K 47/02; A61K 47/10; A61K 47/12; A61K 47/26; A61K 47/32; A61K 47/40; A61K 9/0019; A61K 9/0053; A61P 9/04; A61P 9/12

See application file for complete search history.

(56) References Cited

U.S. PATENT DOCUMENTS

| | | |
|---|---|---|
| 6,730,673 B1 | 5/2004 | Bäckström |
| 10,507,179 B2 | 12/2019 | Weiland |
| 11,213,524 B2 | 1/2022 | Randall |
| 11,607,412 B2 | 3/2023 | Rich |
| 2015/0374689 A1 | 12/2015 | Kelley et al. |
| 2017/0182127 A1 | 6/2017 | Dschietzig |
| 2018/0318210 A1 | 11/2018 | Weiland |
| 2019/0091194 A1 | 3/2019 | Chin et al. |
| 2023/0107461 A1 | 4/2023 | Rich |

FOREIGN PATENT DOCUMENTS

| | | |
|---|---|---|
| WO | WO 1998/001111 | 1/1998 |
| WO | WO 1999/016443 | 4/1999 |
| WO | WO 1999/032081 | 7/1999 |
| WO | WO 1999/055305 | 11/1999 |
| WO | WO 1999/055337 | 11/1999 |
| WO | WO 1999/056134 | 11/1999 |

(Continued)

OTHER PUBLICATIONS

Lam, European Heart Journal, vol. 39, Issue 30, Aug. 7, 2018, pp. 2780-2792. (Year: 2018).*

(Continued)

*Primary Examiner* — Jean P Cornet
(74) *Attorney, Agent, or Firm* — Gary J. Gershik

(57) ABSTRACT

This invention relates to the treatment of Pulmonary Hypertension with heart failure with preserved ejection fraction (PH-HFpEF). More specifically, embodiments of the invention provide compositions and methods useful for the treatment of PH-HFpEF employing the use of levosimendan.

20 Claims, 30 Drawing Sheets

(56) References Cited

FOREIGN PATENT DOCUMENTS

| WO | WO 1999/065888 | 12/1999 |
|---|---|---|
| WO | WO 1999/066912 | 12/1999 |
| WO | WO 2001/000211 | 1/2001 |
| WO | WO 2001/019334 | 3/2001 |
| WO | WO 2001/028560 | 4/2001 |
| WO | WO 2002/000220 | 1/2002 |
| WO | WO 2002/040025 | 5/2002 |
| WO | WO 2002/040026 | 5/2002 |
| WO | WO 2002/047603 | 6/2002 |
| WO | WO 2002/062342 | 8/2002 |
| WO | WO 2003/004035 | 1/2003 |
| WO | WO 2003/007962 | 1/2003 |
| WO | WO 2003/063870 | 8/2003 |
| WO | WO 2004/060375 | 7/2004 |
| WO | WO 2005/102347 | 11/2005 |
| WO | WO 2005/107756 | 11/2005 |
| WO | WO 2005/107757 | 11/2005 |
| WO | WO 2006/087419 | 8/2006 |
| WO | WO 2006/087420 | 8/2006 |
| WO | WO 2006/097570 | 9/2006 |
| WO | WO 2008/082871 | 7/2008 |
| WO | WO 2008/087248 | 7/2008 |
| WO | WO 2009/027577 | 3/2009 |
| WO | WO 2010/097501 | 9/2010 |
| WO | WO 2011/027021 | 3/2011 |
| WO | WO 2016/059287 | 4/2016 |
| WO | WO 2020/041180 A1 | 2/2020 |
| WO | WO 2021/001601 | 1/2021 |
| WO | WO 2021/001601 A1 | 1/2021 |

OTHER PUBLICATIONS

Dec. 1, 2023 Extended European Search Report issued in connection with European Patent Application No. 20900848.1.

Patel et al. "KCNQ-encoded potassium channels as therapeutic targets" Annu. Rev. Pharmacol. Toxicol., Jan. 1, 2019, vol. 59, pp. 41-63.

Levine et al. "Pulmonary vascular disease in the setting of heart failure with preserved ejection fraction" Trends in Cardiovascular Medicine, Elsevier Science, Aug. 17, 2018, vol. 29, No. 4, pp. 2017-2217.

Kleber et al. "Repetitive Dosing of Intravenous Levosimendan Improves Pulmonary Hemodyanmics in Patients with Pulmunoary Hypertension: Results of a Pilot Study." Journal of Clinical Pharmacology, 2009:49:109-115.

Jiang et al. "Efficacy and Safety of a Calcium Sensitizer, Levosimendan, in Patients with Right Heart Failure due to Pulmonary Hypertension." Clin Respir J. Apr. 2018; 12(4):1518-1525. doi: 10.1111/crj. 12699.

Thomas et al. "Clinical Development Success Rates 2006-2015", BIOIndustry Analysis, Jun. 2016, pp. 1-26.

Wong et al. "Estimation of clinical trial success rates and related parameters" Biostatistics 20, 2, 273-286.

Dowden and Munro "Trends in clinical success rates and therapeutic focus" Nat. Rev. Drug Discovery, vol. 18, 495-496 (2019).

Brittain et al. "Elucidating the Clinical Implications and Pathophysiology of Pulmonary Hypertension in Heart Failure With Preserved Ejection Fraction: A call to Action: A science Advisory from the American Heart Association" Circulation 2022; 146:e-73-e88.

Yancy et al. "2013 ACCF/AHA Guideline for Management of Heart Failure: A Report of the American College of Cardiology Foundation / American Heart Association Task Force on Practice Guidelines" ACCF/AHA Practice Guideline, e240-e327.

Wehner et al. "Routinely reported ejection fraction and mortality in clinical practice: where does the nadir of risk lie?" European Heart Journal, (2020) 41, 1249-1257.

Kota et al. "Levosimendan and Calcium Sensitization of the Contractile Proteins in Cardiac Muscle: Impact on Heart Failure," Journal of Cardiovascular Pharmacology and Therapeutics, vol. 13, No. 4, Dec. 2008, 269-278.

Felker and O'Connor "Inotropic therapy for heart failure: An evidenced-based approach," American Heart Journal, Curriculum in Cardiology, Sep. 2001, 142(3), 393-401.

Graffognino et al. "Home Therapies in Advanced Heart Failure: Inotropes and Diuretics" Current heart Failure Reports, 17:314-323 (2020).

Simdax Summary Product Characteristics, Section 4.2, Jun. 2010.

Francis et al. "Inotropes," J Am Coll Cardiol. May 27, 2014; 63(20): 2069-2078.

Chuzi et al. "Palliative Inotrope Therapy: A Narrative Review" JAMA Cardiology Review, 4(8):815-822.

Jennifer Le et al. "Drug Administration" Merck Manual, Consumer Version, Oct. 2020, pp. 1-7.

American Society of Health-System Pharmacists (ASHP) Guidelines on Home Infusion Pharmacy Services, Am J Health-Syst Pharm., 2014; 71:325-41.

Caimmi et al., "Intracoronary Infusion of Levosimendan to Treat Postpericardiotomy Heart Failure" Ann Thorac Surg 2006; 82:e33-4.

Caimmi et al., "Management of acute cardiac failure by intracoronary administration of levosimendan" J Cardiovasc Pharmacol. Sep. 2011; 58(3):245—53.

Kivikko et al. "Oral Levosimendan Increases Cerebral Blood Flow Velocities in Patients with a History of Stroke or Transient Ischemic Attack: A Pilot Safety Study" Current Therapeutic Research 77 (2015) 45-51.

Cudkowicz et al., "Safety and efficacy of oral levosimendan in people with amyotrophic lateral sclerosis (the REFALS study): a randomized, double-blind, placebo-controlled phase 3 trial" Oct. 1, 2021, vol. 20, Issue 10, P821-831.

Kundra et al. "Inhaled Levosimendan versus Intravenous Levosimendan in Patients with Pulmonary Hypertension Undergoing Mitral Valve Replacement" Ann Card Anaesth, 2018; 21:328-32.

Michaels et al., "Effects of Intravenous Levosimendan on Human Coronary Vasomotor Regulation, Left Ventricular Wall Stress, and Myocardial Oxygen Uptake" Circulation, vol. 111, Issue 2, pp. 1504-1509, Mar. 29, 2005.

Strootman and Gregory, "Self-Administration of Intravenous Medications" Specialty Pharmacy Times, Dec. 13, 2013, vol. 4, Issue 6.

Oliva et al. "Repetitive levosimendan treatment in the management of advanced heart failure" European Heart Journal Supplements (2018) 20 (Supplement I), I11-I20.

Lasse Lehtonen, "Levosimendan: A Promising Agent for the Treatment of Hospitalized Patients with Decompensated Heart Failure" Current Cardiology Reports (2000), 2:233-243.

Mushtaq et al. "Levosimendan improves exercise performance in patients with advanced chronic heart failure" ESC Heart Failure 2015; 2: 133-141.

Pieske, Burkert, et al. "Effect of Sacubitril/Valsartan vs Standard Medical Therapies on Plasma NT-proBNP Concentration and Submaximal Exercise Capacity in Patients With Heart Failure and Preserved Ejection Fraction: The PARALLAX Randomized Clinical Trial." JAMA 326.19 (2021): 1919-1929.

Abraham, William T., et al. "Effect of empagliflozin on exercise ability and symptoms in heart failure patients with reduced and preserved ejection fraction, with and without type 2 diabetes." European Heart Journal 42.6 (2021): 700-710.

Armstrong, Paul W., et al. "Effect of vericiguat vs placebo on quality of life in patients with heart failure and preserved ejection fraction: the VITALITY-HFpEF randomized clinical trial." JAMA (2020) Oct. 20; 324(15):1512-1521.

Komajda, Michel, et al. "Effect of ivabradine in patients with heart failure with preserved ejection fraction: the EDIFY randomized placebo-controlled trial." European Journal of Heart Failure 19.11 (2017): 1495-1503.

Altenberger J, et al. "Efficacy and safety of the pulsed infusions of levosimendan in outpatients with advanced heart failure (LevoRep) study: a multicentre randomized trial." Eur J Heart Fail 2014; 16:898—906.

Comín-Colet J, et al. "LION-HEART Study Investigators. Efficacy and safety of intermittent intravenous outpatient administration of levosimendan in patients with advanced heart failure: the LION-HEARTtrial." Eur J Heart Fail 2018.

(56) References Cited

OTHER PUBLICATIONS

García-González, Martín J., et al. "Efficacy and safety of intermittent repeated levosimendan infusions in advanced heart failure patients: the LAICA study." ESC Heart Failure (2021).
Oliva F, et al. on behalf of the RELEVANT-HF Study Group. "Scheduled intermittent inotropes for ambulatory advanced heart failure. The RELEVANT-HF multicentre collaboration." Int J Cardiol (2018).
Nanas JN, et al. "Efficacy and safety of intermittent, long-term, concomitant dobutamine and levosimendan infusions in severe heart failure refractory to dobutamine alone." Am J Cardiol 2005; 95:768—771.
Parissis JT, et al. "Effects of serial levosimendan infusions on left ventricular performance and plasma biomarkers of myocardial injury and neurohormonal and immune activation in patients with advanced heart failure." Heart 2006; 92:1768—1772.
Mavrogeni S, et al. "A 6-month follow-up of intermittent levosimendan administration effect on systolic function, specific activity questionnaire, and arrhythmia in advanced heart failure." J Card Fail 2007; 13:556—559.
Berger R, et al. "Levosimendan and prostaglandin E1 for uptitration of beta-blockade in patients with refractory, advanced chronic heart failure." Eur J Heart Fail 2007; 9:202—208.
Papadopoulou EF, et al. "Assessment of quality of life using three different activity questionnaires in heart failure patients after monthly, intermittent administration of levosimendan during a six-month period." Hell J Cardiol 2009; 50:269—274.
Bonios MJ, et al. "Comparison of three different regimens of intermittent inotrope infusions for end stage heart failure." Int J Cardiol 2012; 159:225—229.
Malfatto G, et al. "Intermittent levosimendan infusions in advanced heart failure: favourable effects on left ventricular function, neurohormonal balance, and one-year survival." J Cardiovasc Pharmacol 2012; 60:450—455.
Slawsky, Mara T., et al. "Acute hemodynamic and clinical effects of levosimendan in patients with severe heart failure." Circulation 102.18 (2000): 2222-2227.
Follath F, Cleland JG, Just H, et al. (2002) "Efficacy and safety of intravenous levosimendan compared with dobutamine in severe low-output heart failure (the LIDO study): a randomised double-blind trial." Lancet. 360 (9328): 196-202.
Moiseyev VS, Poder P, Andrejevs N, et al. (2002) "Safety and efficacy of a novel calcium sensitizer, levosimendan, in patients with left ventricular failure due to AMI. A randomized, placebo-controlled, double-blind study (RUSSLAN)." Eur Heart J. 23(18):1422-32.
Mebazaa A, Nieminen MS, Packer M, et al. (2007) "Levosimendan vs dobutamine for patients with acute decompensated heart failure: the SURVIVE Randomized Trial." JAMA. 297 (17):1883-91.
Packer M, Colucci W, Fisher L, et al. (2013) "Effect of Levosimendan on the Short-Term Clinical Course of Patients With Acutely Decompensated Heart Failure." JCHF. 1 (2): 103-11.
Mehta, Rajendra H., et al. "Levosimendan in patients with left ventricular dysfunction undergoing cardiac surgery." New England Journal of Medicine 376.21 (2017): 2032-2042.
Cavusoglu, Yuksel, et al. "Levosimendan is not effective in reducing pulmonary pressures in patients with idiopathic pulmonary arterial hypertension: report of two cases." Journal of Cardiovascular Medicine 10.6 (2009): 503-507.
Simonneau et al. "Haemodynamic definitions and updated clinical classification of pulmonary hypertension." European Respiratory Journal 2019, 53:1801913, DOI: 10.1183/13993003.01913-2018.
Lai, Yen-Chun, Longfei Wang, and Mark T. Gladwin. "Insights into the pulmonary vascular complications of heart failure with preserved ejection fraction." The Journal of physiology, 597.4 (2019): 1143-1156.
Thenappan, et al. "Clinical characteristics of pulmonary hypertension in patients with heart failure and preserved ejection fraction." Circulation: Heart Failure (2011) DOI: 10.1161/CIRCHEARTFAILURE.110.958801.

Guazzi, Marco. "Pulmonary hypertension in heart failure preserved ejection fraction: prevalence, pathophysiology, and clinical perspectives." Circulation: Heart Failure 7.2 (2014): 367-377.
Dixon, Debra D., Amar Trivedi, and Sanjiv J. Shah, "Combined post-and pre-capillary pulmonary hypertension in heart failure with preserved ejection fraction." Heart Fail Rev (2015): 285-297, DOI 10.1007/s10741-015-9523-6.
Mohammed SF, Roger VL, Abou Ezzeddine OF, Redfield MM. Right ventricular systolic function in subjects with HFPEF: A community-based study. Circulation. 2011; 124: A17407.
Bonderman, Diana, et al. "Acute hemodynamic effects of riociguat in patients with pulmonary hypertension associated with diastolic heart failure (DILATE-1): a randomized, double-blind, placebo-controlled, single-dose study." Chest 146.5 (2014): 1274-1285.
Mascherbauer, Julia, et al. "Evaluation of the pharmacoDYNAMIC effects of riociguat in subjects with pulmonary hypertension and heart failure with preserved ejection fraction." Wiener Klinische Wochenschrift 128.23 (2016): 882-889.
NationalTrials.gov Identifier NCT02744339, "Pharmacodynamic Effects of Riociguat in Pulmonary Hypertension and Heart Failure With Preserved Ejection Fraction (DYNAMIC)"; https://clinicaltrials.gov/ct2/show/NCT02744339.
Gomberg-Maitland, M., et al. "A Multicenter, Randomized, Double-Blind, Placebo-Controlled Study to Evaluate the Safety and Efficacy of Oral Treprostinil in Subjects with Pulmonary Hypertension in Heart Failure with Preserved Ejection Fraction—Design of Study TDE-HF-301." D108. Good Vibrations: Novel Treatment Approaches in Pulmonary Hypertension. American Thoracic Society, 2018. A7591-A7591.
NationalTrials.gov Identifier NCT03037580, "Oral Treprostinil in Subjects With Pulmonary Hypertension Associated With Heart Failure With Preserved Ejection Fraction"; https://clinicaltrials.gov/ct2/show/NCT03037580.
Vachiéry, Jean-Luc, et al. "Macitentan in pulmonary hypertension due to left ventricular dysfunction." European Respiratory Journal 51.2 (2018).
Vachiéry, Jean-Luc, et al. "Pulmonary hypertension due to left heart disease." Eur Respir J (2019); 53:1801897 (2019). Published online Jan. 24, 2019.
NationalTrials.gov Identifier NCT03153111, "A Study to Evaluate Whether Macitentan is an Effective and Safe Treatment for Patients With Heart Failure With Preserved Ejection Fraction and Pulmonary Vascular Disease (SERENADE)"; https://clinicaltrials.gov/ct2/show/NCT03153111.
Hoendermis, Elke S., et al. "Effects of sildenafil on invasive haemodynamics and exercise capacity in heart failure patients with preserved ejection fraction and pulmonary hypertension: a randomized controlled trial." European heart journal 36.38 (2015): 2565-2573.
Koller, B., et al. "Pilot study of endothelin receptor blockade in heart failure with diastolic dysfunction and pulmonary hypertension (BADDHY-Trial)." Heart, Lung and Circulation 26.5 (2017): 433-441.
Ghio, Stefano, et al. "Pulmonary hypertension in left heart disease: The need to continue to explore." International journal of cardiology 288 (2019): 132-134 (abstract).
Sahlholdt Hansen et al. "Levosimendan in pulmonary hypertension and right heart failure." Pulm Circ. Jul.-Sep. 2018;8(3):2045894018790905.
International Search Report issued May 4, 2021 in connection with PCT International Application No. PCT/US2020/065166.
Written Opinion (form PCT/ISA/237) issued May 4, 2021 in connection with PCT International Application No. PCT/US2020/065166.
Senni et al. "New strategies for heart failure with preserved ejection fraction: the importance of targeted therapies for heart failure phenotypes." Eur. Heart J. vol. 35; pp. 2797-2811; Aug. 7, 2014.
Shibata et al., "Congestive heart failure with preserved ejection fraction is associated with severely impaired dynamic Starling mechanism." J. Appl. Physiol. vol. 110; No. 4; pp. 964-971; Feb. 10, 2011.
Valjakka-Koskela et al. "Transdermal delivery of levosimendan." Eur. J. Pharm. Sci. vol. 11; pp. 343-350; Jul. 11, 2000.

(56) References Cited

OTHER PUBLICATIONS

Burkoff et al. "Levosimendan Imporves Hemodynamics and Exercise Tolerance in PH-HFpEF: Results of the randomized Placebo-Controlled HELP Trial." JACC Heart Fail. 2021; 9(5):360-370.
Litwin and Zile. "The Vexing Problem of HFpEF Therapeutics." commentary to: "Levosimendan Imporves Hemodynamics and Exercise Tolerance in PH-HFpEF: Results of the randomized Placebo-Controlled HELP Trial." JACC Heart Fail. 2021; 9(5):371-373.
Borlaug, Barry A., et al. "Levosimendan Improves Hemodynamics and Submaximal Exercise Capacity In Ph-hfpef: Primary Results From the Help-ph-hfpef Multicenter Randomized Controlled Trial." Journal of Cardiac Failure12 (2020): 1108.
Burkhoff, Daniel, et al. "24-hour Levosimendan Infusion Decreases Biventricular Filling Pressures and Increases Cardiac Output at Rest and Exercise in PHHFpEF." CirculationSuppl_3 (2020): A15294-A15294.
Gorter TM, Obokata M, Reddy YNV, Melenovsky V, Borlaug BA. Exercise unmasks distinct pathophysiologic features in heart failure with preserved ejection fraction and pulmonary vascular disease. Eur Heart J 2018; 39:2825—35.
Obokata M, Reddy YNV, Melenovsky V, Pislaru S, Borlaug BA. Deterioration in right ventricular structure and function over time in patients with heart failure and preserved ejection fraction. Eur Heart J 2019; 40:689—97.
Adamson PB, Abraham WT, Bourge RC, et al. Wireless pulmonary artery pressure monitoring guides management to reduce decompensation in heart failure with preserved ejection fraction. Circ Heart Fail 2014; 7:935—44.
Papp Z, Édes I, Fruhwald S, de Hert SG, et al. Levosimendan: molecular mechanisms and clinical implications: consensus of experts on the mechanisms of action of levosimendan. Int J Cardiol 2012; 159:82—7.
Altenberger J, Gustafsson F, Harjola VP, et al. Levosimendan in acute and advanced heart failure: an appraisal of the clinical database and evaluation of its therapeutic applications. J Cardiovasc Pharmacol 2018; 71:129—36.
Lilleberg J, Laine M, Palkama T, Kivikko M, Pohjanjousi P, Kupari M. Duration of the haemodynamic action of a 24-h infusion of levosimendan in patients with congestive heart failure. Eur J Heart Fail 2007; 9:75—82.
Ryerson CJ, Nayar S, Swiston JR, Sin DD. Pharmacotherapy in pulmonary arterial hypertension: a systematic review and meta-analysis. Respir Res 2010; 11:12.
Vanderpool RR, Saul M, Nouraie M, Gladwin MT, Simon MA. Association between hemodynamic markers of pulmonary hypertension and outcomes in heart failure with preserved ejection fraction. JAMA Cardiol 2018; 3:298—306.
Maack C, Eschenhagen T, Hamdani N, et al. Treatments targeting inotropy. Eur Heart J 2019; 40:3626—44.
Fallick C, Sobotka PA, Dunlap ME. Sympathetically mediated changes in capacitance: redistribution of the venous reservoir as a cause of decompensation. Circ Heart Fail 2011; 4: 669—75.
Höhn J, Pataricza J, Petri A, Tóth GK, Balogh A, Varró A, Papp JG. Levosimendan interacts with potassium channel blockers in human saphenous veins. Basic Clin Pharmacol Toxicol 2004; 94: 271—3.
Reddy YNV, Rikhi A, Obokata M, et al. Quality of life in heart failure with preserved ejection fraction: importance of obesity, functional capacity, and physical inactivity. Eur J Heart Fail 2020; 22:1009—18.
D'Alonzo GE, Barst RJ, Ayres SM, et al. Survival in patients with primary pulmonary hypertension. Results from a national prospective registry. Ann Intern Med 1991; 115:343—9.
Zile MR, Bennett TD, El Hajj S, et al. Intracardiac pressures measured using an implantable hemodynamic monitor: relationship to mortality in patients with chronic heart failure. Circ Heart Fail 2017; 10:e003594.

Jan. 16, 2018 Press release—Tenax Therapeutics Announces Plan to Develop Levosimendan for a Pulmonary Hypertension Indication with No FDA Approved Therapies.
Feb. 6, 2018 Press release—World-Recognized Experts Join Tenax Therapeutics' Scientific Advisory Board to Guide New Phase 2 Study.
Mar. 1, 2018 Press release—Tenax Therapeutics Announces New Scientific Publication of Preclinical Data Provides Additional Evidence of Levosimendan Treatment Effects in Pulmonary Hypertension.
Apr. 4, 2018 Press release—Tenax Therapeutics Announces Results of Pre-IND Meeting with FDA for Phase 2 Study of Levosimendan in PH-HFpEF Patients.
Mar. 11, 2019 Press release—Tenax Therapeutics Enrolls First Patient for Phase 2 Pulmonary Hypertension Clinical Trial.
Aug. 23, 2019 Press release—Tenax Therapeutics Provides Clinical Development Update.
Oct. 31, 2019 Press release—Tenax Therapeutics Provides Update on Phase 2 Pulmonary Hypertension Clinical Trial.
Mar. 12, 2020 Press release—Tenax Therapeutics Completes Enrollment in Phase 2 Pulmonary Hypertension Trial.
Apr. 4, 2020 Press release—Tenax Therapeutics Announces Last Patient Completes Final Visit in its Phase 2 "HELP Study" of Levosimendan.
Jun. 2, 2020 Press release—Tenax Therapeutics Reports Positive Results from Phase 2 Trial.
Aug. 31, 2020 Press release—Tenax Announces Late-Breaking Results from the HELP Study.
Oct. 2, 2020 Press release—Tenax Therapeutics Announces Late-Breaking Clinical Trial Presentation.
Nov. 10, 2020 Press release—Tenax Therapeutics Announces Presentation of 24-Hour HELP Study Results at the American Heart Association Scientific Sessions 2020.
Jan. 4, 2022 Press release—Tenax Therapeutics Provides Update on TNX-102, TNX-103 and TNX-201 Clinical Programs.
ClinicalTrials.gov Study No. NCT03541603 (Version 1).
ClinicalTrials.gov Study No. NCT03541603 (Version 2).
ClinicalTrials.gov Study No. NCT03541603 (Version 3).
ClinicalTrials.gov Study No. NCT03541603 (Version 4).
ClinicalTrials.gov Study No. NCT03541603 (Version 5).
ClinicalTrials.gov Study No. NCT03541603 (Version 16).
ClinicalTrials.gov Study No. NCT03541603 (Version 18).
International Preliminary Report on Patentability issued Jun. 30, 2022 in connection with PCT International Application No. PCT/US2020/065166.
Guazzi et al. "Pulmonary Hypertension in HFpEF and HFrEF" JACC vol. 76, No. 9, 2020, Sep. 1, 2020:1102-11.
Palau, Patricia, et al. "Effect of β-blocker withdrawal on functional capacity in heart failure and preserved ejection fraction." Journal of the American College of Cardiology 78.21 (2021): 2042-2056.
Conraads, Viviane M., et al. "Effects of the long-term administration of nebivolol on the clinical symptoms, exercise capacity, and left ventricular function of patients with diastolic dysfunction: results of the ELANDD study." European journal of heart failure 14.2 (2012): 219-225.
Deswal, Anita, et al. "Results of the randomized aldosterone antagonism in heart failure with preserved ejection fraction trial (RAAM-PEF)." Journal of cardiac failure 17.8 (2011): 634-642.
Hosenpud, Jeffrey D. "Levosimendan, a novel myofilament calcium sensitizer, allows weaning of parenteral inotropic therapy in patients with severe congestive heart failure." The American journal of cardiology 83.12 (1999): 9-11.
Ponikowski et al. "2016 ESC Guidelines for the Diagnosis and Treatment of Acute and Chronic Heart Failure" European Heart Journal (2016) 37, 2129-2200.
Yoon and Eom "Heart failure with preserved ejection fraction: present status and future directions" Experimental & Molecular Medicine 51, 1-9 (2019).

* cited by examiner

|  | Placebo n=18 | Levosimendan n=18 |
|---|---|---|
| Any Treatment Emergent AEs (TEAEs) | 8 (44%) | 13 (72%) |
| TEAEs by Severity<br>Mild<br>Moderate<br>Severe | 5 (28%)<br>2 (11%)<br>1 (6%) | 9 (50%)<br>2 (11%)<br>2 (11%) |
| Any Drug-Related TEAEs | 5 (28%) | 9 (50%) |
| TEAEs of Special Interest † | 0 | 0 |
| Serious TEAEs | 1 (6%) | 3 (17%) |

† hypotension, atrial fibrillation, other significant arrhythmia, resuscitated death, stroke

Figure 16

|  | Placebo n=18 | Levosimendan n=18 |
|---|---|---|
| Headache | 1 (6%) | 3 (17%) |
| Heart Rate Increased | 0 (0%) | 2 (11%) |
| Fatigue | 2 (11%) | 1 (6%) |
| Cardiac Failure Acute | 1 (6%) | 2 (11%) |
| Dyspnea | 1 (6%) | 2 (11%) |
| Vascular Access Site Pain | 2 (11%) | 0 (0%) |
| Muscle Spasms | 0 (0 %) | 2 (11%) |
| Hypokalaemia | 1 (6%) | 2 (11%) |

Figure 17

| Event on Levosimendan | Severity | Relatedness/ Change in Dose |
|---|---|---|
| Infections and Infestations, Device related infection | severe | not related, dose interrupted |
| Infections and Infestations, Bacteremia | moderate | not related, dose not changed |
| Cardiac disorders, Cardiac failure acute | mild | not related, dose not changed |
| Cardiac disorders, Cardiac failure acute | moderate | not related, dose not changed |

Figure 18

| Characteristic | All Randomized (N=37) | Placebo (N=19) | Treatment (N=18) | p Placebo vs Treatment |
|---|---|---|---|---|
| Age (years) | 68.1 ± 9.3 | 67.4 ± 11.0 | 68.9 ± 7.5 | 0.65 |
| Male Gender, n (%) | 14 (37.8) | 6 (31.6) | 8 (44.4) | 0.42 |
| Race, n (%) | | | | 0.51 |
|   White | 32 (86.5) | 16 (84.2) | 16 (88.9) | |
|   Black or African American | 3 (8.1) | 2 (10.5) | 1 (5.6) | |
|   American Indian or Alaska Native | 1 (2.7) | 1 (5.3) | 0 (0.0) | |
|   Other | 1 (2.7) | 0 (0.0) | 1 (5.6) | |
| Weight (kg) | 98.2 ± 20.5 | 95.9 ± 20.8 | 100.6 ± 20.4 | 0.50 |
| Height (cm) | 169.9 ± 10.21 | 170.5 ± 9.27 | 169.3 ± 11.36 | 0.72 |
| BSA | 2.14 ± 0.25 | 2.12 ± 0.25 | 2.16 ± 0.23 | 0.6 |
| BMI (kg/m²) | 34.3 ± 8.2 | 33.0 ± 7.2 | 35.6 ± 9.2 | 0.35 |
| Medical History | | | | |
|   Atrial Fibrillation, % of time | 29.7 ± 46.3 | 15.8 ± 37.4 | 44.4 ± 51.1 | 0.06 |
|   Atrial Fibrillation (history) | 28 (75.7) | 12 (63.2) | 16 (88.9) | 0.07 |
|   Obesity, n (%) | 8 (21.6) | 4 (21.1) | 4 (22.2) | 0.93 |
|   DM, n (%) | 6 (16.2) | 2 (10.5) | 4 (22.2) | 0.33 |
|   HTN, n (%) | 19 (51.4) | 10 (52.6) | 9 (50.0) | 0.87 |
|   CAD, n (%) | 11 (29.7) | 5 (26.3) | 6 (33.3) | 0.64 |
|   CKD, n (%) | 11 (29.7) | 5 (26.3) | 6 (33.3) | 0.64 |
|   Obstructive Sleep Apnea, n (%) | 24 (64.9) | 12 (63.2) | 12 (66.7) | 0.82 |
|   COPD, n (%) | 7 (18.9) | 2 (10.5) | 5 (27.8) | 0.18 |
|   Interstitial Lung Disease, n (%) | 2 (5.4) | 0 (0.0) | 2 (11.1) | 0.14 |
|   Pulmonary Embolism/DVT, n (%) | 2 (5.4) | 2 (10.5) | 0 (0.0) | 0.16 |
| NYHA, n (%) | | | | |
|   I | 0 (0.0) | 0 (0.0) | 0 (0.0) | 0.68 |
|   II | 5 (13.5) | 3 (15.8) | 2 (11.1) | |
|   III | 32 (86.5) | 16 (84.2) | 16 (88.9) | |
| Vital Signs | | | | |
|   HR | 71.2 ± 10.76 | 68.5 ± 10.36 | 74.1 ± 10.71 | 0.12 |
|   SBP | 130.3 ± 16.47 | 129.9 ± 16.12 | 130.7 ± 17.30 | 0.89 |
|   DBP | 69.2 ± 11.02 | 70.4 ± 11.40 | 67.9 ± 10.78 | 0.50 |
|   RR | 16.9 ± 2.17 | 17.4 ± 1.98 | 16.4 ± 2.30 | 0.17 |
| 6-Minute Walk Distance | 284.6 ± 106.24 | 279.8 ± 85.24 | 289.7 ± 127.12 | 0.78 |
| Echocardiogram | | | | |
|   LVEF | 58.4 ± 7.5 | 58.8 ± 8.2 | 58.1 ± 6.9 | 0.80 |
|   LA Dimension | 92.0 ± 40.1 | 82.4 ± 33.3 | 102.2 ± 44.9 | 0.13 |
|   TAPSE | 1.8 ± 0.4 | 1.7 ± 0.5 | 1.8 ± 0.3 | 0.76 |

Figure 22

| Parameter | Baseline, mean (SD) | | | Δ24Hr, mean (95% CI) | | |
|---|---|---|---|---|---|---|
| | Legs Down | Legs Up | 25 Watts | Legs Down | Legs Up | 25 Watts |
| HR (bpm) | 69.6 (16.4) | 71.0 (15.9) | 86.3 (18.0) | +5.7 (2.9,8.4)* | +6.7 (3.6,9.7)* | +4.8 (0.2,9.3)* |
| CVP (mmHg) | 15.5 (5.2) | 18.9 (6.5) | 27.1 (8.6) | -3.9 (-5.3,-2.6)* | -3.3 (-4.8,-1.7)* | -4.7 (-6.8,-2.6)* |
| PA Mean (mmHg) | 41.0 (9.3) | 46.4 (9.6) | 57.3 (13.3) | -4.2 (-6.4,-1.9)* | -4.3 (-6.6,-2.1)* | -2.7 (-5.9,0.4) |
| PCWP (mmHg)* | 25.7 (6.3) | 29.7 (7.8) | 36.8 (11.3) | -4.9 (-7.0,-2.9)* | -5.3 (-7.3,-3.3)* | -3.9 (-6.8,-0.9)* |
| AoS (mmHg) | 135.0 (18.8) | 138.4 (18.7) | 155.7 (34.7) | -4.7 (-12.2,2.8) | -1.4 (-8.5,5.7) | -7.2 (-17.5,3.1) |
| CI (L/min/M2) | 2.5 (0.8) | 2.6 (0.9) | 3.2 (1.1) | 0.1 (-0.0,0.3) | 0.1 (-0.0,0.3) | 0.2 (-0.0,0.4) |
| SVR (Wood Units) | 15.5 (4.2) | 15.3 (5.2) | 12.5 (5.6) | -1.1 (-2.2,0.0) | -0.4 (-1.8,1.0) | -1.0 (-2.7,0.8) |
| PVR (Wood Units) | 3.3 (2.6) | 2.7 (1.6) | 3.6 (2.9) | -0.1 (-0.6,0.3) | 0.2 (-0.3,0.7) | 0.0 (-0.4,0.5) |

Figure 23

| Parameter | Group | Baseline, mean (SD) | | | Placebo-Corrected Effect of Change from Baseline at 6 Weeks, LS mean (95% CI) | | |
|---|---|---|---|---|---|---|---|
| | | Legs Down | Legs Up | 25 Watts | Legs Down | Legs Up | 25 Watts |
| HR (bpm) | Placebo | 66.6 (9.6) | 66.8 (10.0) | 79.1 (11.2) | 4.1 (-0.4, 8.7) | 2.8 (-3.5, 9.2) | 9.3 (-0.4, 19.0) |
| | Treatment | 70.6 (14.4) | 70.7 (15.0) | 80.3 (18.4) | | | |
| CVP (mmHg) | Placebo | 16.6 (5.4) | 19.9 (5.0) | 28.4 (6.8) | -3.1 (-6.4, 0.3) | -3.9 (-8.2, 0.4) | -3.0 (-8.1, 2.1) |
| | Treatment | 14.9 (5.2) | 18.8 (8.1) | 27.7 (10.2) | | | |
| PAS (mmHg) | Placebo | 67.2 (21.2) | 75.6 (20.9) | 87.6 (24.9) | -2.3 (-8.3, 3.7) | 0.4 (-7.1, 7.9) | -0.9 (-9.7, 7.9) |
| | Treatment | 64.8 (19.0) | 70.7 (18.7) | 90.7 (22.1) | | | |
| PAD (mmHg) | Placebo | 28.9 (6.9) | 32.3 (7.0) | 39.6 (10.4) | -3.1 (-6.4, 0.3) | -1.8 (-6.2, 3.1) | -1.2 (-6.3, 3.8) |
| | Treatment | 28.6 (5.6) | 32.3 (8.17) | 40.5 (6.6) | | | |
| PA Mean (mmHg) | Placebo | 40.7 (10.8) | 46.7 (11.0) | 55.6 (14.8) | -2.9 (-6.7, 0.1) | -1 (-5.9, 4.8) | -1.3 (-6.7, 4.1) |
| | Treatment | 40.7 (9.3) | 45.1 (10.1) | 57.4 (10.8) | | | |
| PCWP (mmHg)† | Placebo | 24.9 (6.5) | 28.6 (7.6) | 35.5 (11.8) | -3.4 (-7.3, 0.5) | -5.6 (-10.3, -1.0) | -1.4 (-7.7, 4.8) |
| | Treatment | 28.2 (6.3) | 31.1 (7.2) | 37.8 (8.3) | | | |
| AoS (mmHg) | Placebo | 141.5 (18.4) | 141.1 (16.8) | 151.4 (31.1) | 1.6 (-11.6, 14.8) | 0.4 (-13.9, 14.7) | -2.4 (-25.0, 20.1) |
| | Treatment | 132.4 (19.1) | 137.1 (10.1) | 140.0 (30.7) | | | |
| CI (L/m/M2) | Placebo | 2.3 (0.6) | 2.5 (0.5) | 3.0 (0.9) | 0.2 (-0.2, 0.6) | 0.10 (-0.5, 0.7) | 0.2 (-0.4, 0.8) |
| | Treatment | 2.7 (1.0) | 2.9 (1.1) | 3.5 (1.3) | | | |
| SVR (Wood Units) | Placebo | 16.8 (3.4) | 15.3 (3.2) | 12.7 (3.2) | -1.0 (-4.2, 0.3) | 0.04 (-3.5, 3.5) | -2.1 (-5.0, 1.1) |
| | Treatment | 14.0 (4.8) | 13.2 (4.8) | 10.8 (3.9) | | | |
| PVR (Wood Units) | Placebo | 4.1 (3.6) | 2.2 (1.0) | 9.99 (3.6) | -0.24 (-1.46, 0.98) | -0.05 (-1.46, 1.35) | -0.3 (-1.5, 0.9) |
| | Treatment | 2.7 (1.5) | 2.6 (1.5) | 3.1 (1.9) | | | |

Figure 24

LEVOSIMENDAN FOR TREATING PULMONARY HYPERTENSION WITH HEART FAILURE WITH PRESERVED EJECTION FRACTION (PH-HFpEF)

This application claims the benefit of U.S. Provisional Application Nos. 63/064.671 filed Aug. 12, 2020, 63/033,773 filed Jun. 2, 2020, 62/988,720 filed Mar. 12, 2020, 62/967,920 filed Jan. 30, 2020, and 62/948,735 filed Dec. 16, 2019, the contents of each of which are hereby incorporated by reference.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

FIELD OF THE INVENTION

The invention relates to the treatment of heart failure with preserved ejection fraction, specifically in human subjects who also have pulmonary hypertension (PH-HFpEF patients).

BACKGROUND OF THE INVENTION

Levosimendan

Levosimendan is a calcium sensitizer and potassium channel activator drug approved in over 60 countries for intravenous use in hospitalized subjects with acutely decompensated heart failure (ADHF). Levosimendan is currently approved for in-hospital use only, and currently approved only for administration in a hospital setting where adequate monitoring facilities and expertise with the use of inotropic agents are available. (Simdax. Finland: Orion Corporation; 2010.)

Levosimendan enhances the calcium sensitivity of contractile proteins by binding to cardiac troponin C in a calcium-dependent manner. Levosimendan increases the contraction force but does not impair ventricular relaxation. In addition, levosimendan opens ATP-sensitive potassium channels in vascular smooth muscle, thus inducing vasodilatation of systemic and coronary arterial resistance vessels and systemic venous capacitance vessels. Levosimendan is also a selective phosphodiesterase III inhibitor in vitro. (Simdax. Finland: Orion Corporation; 2010.)

Levosimendan has been studied exclusively in heart failure patients with reduced ejection fraction (HFrEF). In fact, with the single exception of the Hemodynamic Evaluation of Levosimendan in HP-HFpEF (HELP) Study (Borlaug 2020, Burkhoff 2020) that this invention is based upon, all of the many prior multicenter randomized placebo-controlled trials of levosimendan in heart failure patients have specifically excluded heart failure patients with preserved ejection fraction (HFpEF). The complete lack of clinical research evaluating levosimendan in HFpEF and PH-HFpEF patients is consistent with the historical treatment paradigm that levosimendan should be used to treat HFrEF patients. The HELP Study represents a major departure from this traditional mindset and as a result the findings from this novel clinical trial represent significant and surprising discoveries regarding the benefits of levosimendan in PH-HFpEF patients.

In HFrEF patients, the positive inotropic and vasodilatory actions of levosimendan result in an increased contractile force, and a reduction in both preload and afterload, without adversely affecting diastolic function. Hemodynamic studies in healthy volunteers and in patients with stable and unstable heart failure have shown a dose-dependent effect of levosimendan given intravenously as loading dose (3 micrograms/kg to 24 micrograms/kg) and continuous infusion (0.05 to 0.2 micrograms/kg per minute). Compared with placebo, in HFrEF patients levosimendan increased cardiac output, stroke volume, ejection fraction, and heart rate and reduced systolic blood pressure, diastolic blood pressure, pulmonary capillary wedge pressure, right atrial pressure, and peripheral vascular resistance. (Simdax. Finland: Orion Corporation; 2010.)

Levosimendan's activity is mediated through unique mechanisms of action, including: increased cardiac contractility by calcium sensitization of troponin C vasodilation through opening of potassium channels, and cardioprotective effects via potassium channel opening in mitochondria. (Haikala et al. 1995, Haikala et al. 1995, Pollesello et al. 1994, Sorsa et al. 2004, Yokoshiki et al. 1997, Patariczia et al. 2000, Kaheinen et al. 2001, Erdei et al. 2006, Maytin et al. 2005, Pollesello et al. 2007, du Toit et al. 2008, Louhelainen et al. 2010)

Levosimendan has been shown to be a potent and selective phosphodiesterase-3 (PDE3) inhibitor in vitro. The drug is PDE3 selective with a PDE3/PDE4 inhibition ratio of 10,000. However, both isozymes must be inhibited in cardiomyocytes to exert an effect on the cAMP concentration and inotropic effects. The classical PDE inhibitors (i.e., milrinone, enoximone, and amrinone) inhibit both PDE3 vs. PDE4 is as low as 17-fold), which accounts fully for their inotropic effect. (Yokoshiki et al. 1997, Szilagyi et al. 2004)

Levosimendan improves endothelial function and enhances diastolic coronary flow by opening the adenosine triphosphate-sensitive potassium channels and increasing nitric oxide production. Levosimendan acts through direct binding to troponin-C at high systolic intracellular calcium concentration as well as detachment from it at low diastolic concentration are facilitated. Levosimendan displayed positive lusitropic effects relative to milrinone and nitroglycerin. The lusitropic effect of levosimendan is independent of the degree of the inotropic effect. (Michaels et al. 2005, Grossini et al. 2005, Hasenfuss et al. 1998, De Luca et al. 2006)

Metabolites OR-1896 and OR-1855

Levosimendan has an active metabolite that extends its effects well beyond the infusion period. Following intravenous or oral dosing, levosimendan is reduced by intestinal bacteria to form OR-1855 (limited activity) that is acetylated to form OR-1896, an active metabolite. While the patient half-life is approximately 1 hour and cleared a few hours after the end of intravenous infusion, OR-1896 has a prolonged half-life of 70-80 hours in heart failure subjects with roughly equal exposures of OR-1855 and OR-1896 maintained through deacetylation/acetylation pathways. The OR-1896 metabolite has been shown to retain similar hemodynamic and pharmacologic properties of levosimendan and maintain roughly equivalents to levosimendan in preclinical models. This activity occurs despite considerably lower plasma concentrations relative to levosimendan, an apparent result of a large percentage of unbound OR-1896 in circulation. Thus, in extended repeated dosing, levosimendan is essentially an active prodrug to an active metabolite moiety, OR-1896. (Louhelainen et al. 2010, Erdei et al. 2006, Szilagyi et al. 2004, Banfor et al. 2008, Louhelainen et al. 2009, Segreti et al. 2008)

OR-1896 is equipotent to levosimendan in its inotropic effects in whole cardiomyocytes and isolated contractile apparatus preparations. However, OR-1896 is profoundly less potent in the inhibition of both PDE3 and PDE4 isozymes. This supports the hypothesis that the main component of the inotropic effect for both levosimendan and OR-1896 is a result of their binding to troponin C and not through PDE inhibition. (Szilagyi et al. 2004)

Clinical observations demonstrate that short-term levosimendan administration is followed by long-term hemodynamic changes that parallel the levels of OR-1896. Patients have been observed with detectable concentrations of both metabolites, OR-1896 and OR-1855, in follow-ups two weeks after treatment. Despite OR-1855's observed inactivity, OR-1896 greatly extends the parent levosimendan's activity and provides the primary active moiety in subjects receiving intermittent intravenous levosimendan therapy. (Banfor et al. 2007, Kivikko et al. 2003, Kivikko et al. 2002)

Based on knowledge of OR-1896 and OR-1855, administration of the metabolites could be used analogously to levosimendan, with adjustments made for the metabolites' own parameters. Both metabolites could be delivered through various routes of administration, including but not limited to, oral, intravenous, and subcutaneous administration. The dose chosen depends on the specific route of administration. In all cases, the target dosing would be intended to achieve a steady-state concentration of OR-1896 of 0.5 to 10.0 ng/ml. The relationship between levosimendan and OR-1896 and OR-1855, along with the interaction between the metabolites, is discussed in Pharmacodynamics and Safety of a New Calcium Sensitizer, Levosimendan, and Its Metabolites during an Extended Infusion in Patients with Severe Heart Failure (Kivikko et al. 2002), the entire contents of which are incorporated by reference.

Types of Heart Failure—HFrEF Vs. HFpEF

HFpEF and HFrEF are distinct clinical entities. While each type of heart failure accounts for approximately 50% of all heart failure patients, many differences exist between these two forms of heart failure.

A recent review by Shaw et al. described some of the distinct features of HFpEF and HFrEF, summarized in the chart below. The review noted that over the past three decades, HFrEF evolved into its own distinct therapeutic entity due to the efficacy of neurohormonal inhibition seen in large outcome clinical trials. However. HFpEF has not undergone a similar evolution due to the consistent failure of large trials testing neurohormonal inhibition either individually or on meta-analysis. (Shaw et al. 2016)

| Unequal Structural, Functional, and Ultra-structural LV Characteristics in HFpEF and HFrEF | | |
|---|---|---|
| | HFpEF | HFrEF |
| LV structure/function | | |
| End-diastolic volume | ↔ | ↑ |
| End systolic volume | ↔ | ↑ |
| Wall thickness | ↑ | ↔ |
| Mass | ↑ | ↑ |
| Mass/volume ratio | ↑ | ↓ |
| Remodeling | Concentric | Eccentric |
| Ejection fraction | ↔ | ↓ |
| Stroke work | ↔ | ↓ |
| End-systolic elastance | ↔ | ↓ |
| End-diastolic stiffness | ↑ | ↓ |
| LV ultrastructure | | |
| Myocyte diameter | ↑ | ↔ |
| Myocyte length | ↔ | ↑ |
| Myocyte remodeling | Concentric | Eccentric |
| Fibrosis | Interstitial/reactive | Focal/replacement |

Pulmonary Hypertension—Heart Failure with Preserved Ejection Fraction (PH-HFpEF)

Many HFpEF patients have coexisting Pulmonary Hypertension. A sustained elevation in left atrial pressure causes pulmonary venous congestion, which often leads to elevation of pulmonary pressures leading to severe right ventricular failure with a low cardiac output, edema, hypoxemia, and severely limited exercise capacity. Pulmonary hypertension (PH) in subjects with heart failure and preserved ejection fraction (PH-HFpEF) is a common form of pulmonary hypertension and has an estimated US prevalence exceeding 1.5 million. (Oktay et al. 2013, Oudiz et al. 2007, Hoeper et al. 2016)

PH-HFpEF has been classified within Group II of the World Health Organization (WHO) clinical classification of PH, characterized by PH arising from left heart disease. Regardless of the basis of left heart disease. PH initially develops from a passive backward transmission of filling pressures, mainly driven by left ventricular (LV) diastolic function, resulting in a chronic increase in left atrial pressure and a loss of left atrial compliance. These mechanical components of pulmonary venous congestion may trigger pulmonary vasoconstriction, decreased nitric oxide (NO) availability, increased endothelin expression, desensitization to natriuretic peptide-induced vasodilation, and vascular remodeling. Finally, these changes often lead to advanced pulmonary vascular disease, increased right ventricle (RV) afterload, and RV failure. PH-HFpEF is defined hemodynamically by a pulmonary artery pressure (mPAP)≥25 mmHg, a pulmonary capillary wedge pressure (PCWP)>15 mmHg, and a diastolic pressure gradient [diastolic PAP−PCWP]>7 mmHg. (Galie et al. 2009, McLaughlin et al. 2009, Simonneau et al. 2009, Dixon et al. 2015)

ESC guidelines in the treatment of PH-HFpEF subjects acknowledge that the accepted treatment target is a reduction of pulmonary wedge pressures using diuretics for congestion. However, clinical studies have demonstrated neutral results with identified concerns that Pulmonary Hypertension (PH)-targeted therapies could have detrimental effects due to rapid increases in LV filling pressures, resulting in acute pulmonary edema. Thus, the ESC guidelines specify that there are currently no established strategies to treat pulmonary vascular disease (PVD) and right ventricular disease (RVD) in HFpEF, with a recommendation (class III) not to use approved PAH treatments in PH-HFpEF subjects. With no demonstrated effective therapy, these subjects have a poor outcome (5 yr. survival <50%, frequent hospitalizations). (Shaw et al. 2016, Galie et al. 2009, Gorter et al. 2018, Klapholz et al. 2004)

Levosimendan has never previously been studied in the PH-HFpEF population. The complete lack of research regarding levosimendan's potential utility in PH-HFpEF likely stems from the fact that inotropes such as levosimendan, are recommended in most heart failure guidelines to be used exclusively in the treatment of HFrEF and not HFpEF patients. As an example, the 2013 ACCF/AHA guidelines for management of heart failure specifically limits its recommendation for inotrope use to HFrEF patients, stating "Use of parenteral inotropic agents in hospitalized patients without documented severe systolic dysfunction, low blood pressure, or impaired perfusion and evidence of significantly depressed cardiac output, with or without congestion, is potentially harmful."

Failed Treatment Attempts

Additionally, none of the currently approved drugs used to treat other forms of pulmonary hypertension have shown to be effective in PH-HFpEF. In fact, all prior trials that have tested other drugs in PH-HFpEF have repeatedly reported neutral to negative results. (ElGuindy et al. 2012).

Numerous review articles have been published attempting to consolidate the repeated failures in attempted treatments of PH-HFpEF. One, in particular, Pulmonary Vascular Disease in the Setting of Heart Failure with Preserved Ejection Fraction, written by Andrea R. Levine et al., consolidated all the background information behind the disease while also applying this background information to previously failed attempts. The comments on failed attempts of various therapeutics is referenced below to help explain the vast difficulty in treating PH-HFpEF.

One targeted pathway in previous clinical trials was the Nitrate-NO-sGC-cGMP pathway. While several small, single-center trials have reported positive results treating PH-HFpEF with PDE5i, a large multicenter study was negative, making it unlikely that PDE5i will ever be an approved therapy for PH-HFpEF. In 2015, Hoendermis et al. found no change in mPAP after 12 weeks of sildenafil administration in 52 patients. The RELAX trial sought to establish whether chronic sildenafil administration changed peak oxygen consumption at 24 weeks in patients with HFpEF. However, long term sildenafil treatment failed to improve six-minute walk time, clinical status, or quality of life in this multicenter trial of 216 patients. The SIOVAC trial was a multicenter placebo control trial of sildenafil in patients with PH-left heart disease (LHD) secondary to valvular heart disease. This study reinforced the risk associated with use of sildenafil in patients with PH-LHD, and it also supported the recommendations against the use of PDE5i in patients with PH-LHD. Due to these negative results seen to date, the efficacy of PDE5i in PH-HFpEF seems highly unlikely. The multicenter INDIE-HFpEF studied the acute cardiopulmonary hemodynamic effects of inorganic nitrite infusion. However, this study was also unsuccessful, as it was unable to demonstrate any improvement in the primary endpoint of peak oxygen consumption during cardiopulmonary exercise or secondary endpoints including activity level, quality of life score, or NT-proBNP in patients treated with inhaled sodium nitrite 3 times a day for 4 weeks. Another study, conducted by Simon et al., further evaluated inhaled nitrites in PH-HFpEF patients with some promising data related to cardiopulmonary hemodynamics; however, improvements in clinical endpoints have not been demonstrated to date. The DILATE trial and SOCRATES-PRESERVED trial both assessed the acute hemodynamic effects of sGC stimulators, riociguat and vericiguat respectively. Although the DILATE trial showed some promising results, the primary outcome was not achieved in mean pulmonary arterial pressure, along with no change in TPG or pulmonary vascular resistance. The SOCRATES-PRESERVED trial ended with similar results, where the primary endpoints also saw no significant changes. (Levine et al. 2019)

Endothelin receptors are another previously targeted molecular target for treatment of PH-HFpEF. MELODY-1 was a small pilot study evaluating macitentan in patients with left heart disease. However, primary outcomes were fluid retention and worsening of the New York Heart Association (NYHA) functional class. Additionally, no change was seen in hemodynamic parameters such as pulmonary vascular resistance, mean pulmonary arterial pressure, or pulmonary artery wedge pressure. The BADDHY trial also attempted using an endothelin receptor antagonist, bosentan, in patients with PH-HFpEF, but no improvements were seen in the six minute walk test or echocardiographic evaluation of pulmonary hypertension. Patients who received bosentan actually had worse clinical outcomes than those who only received the placebo. Neither of these two studies indicated any success with endothelin receptor antagonists in treating PH-HFpEF. (Levine et al. 2019)

The largest clinical trial in HFpEF to date was the PARAGON-HF trial conducted by Novartis. This trial was designed to evaluate the effect of sacubitril/valsartan on HFpEF patients. PARAGON-HF was yet another example of a large clinical trial where the reduction in the primary endpoint was not statistically significant. (Novartis 2019)

According to 2009 ACCF/AHA and 2015 ESC/ERS Guidelines, there is no current clinically approved treatment for PH-HFpEF. Given the numerous amount of failures and adverse effects known in the field as summarized above, no drug can be expected to treat PH-HFPEF, but there is a strong need in the field to find a treatment for this currently untreatable disease. (Levine et al. 2019).

SUMMARY OF THE INVENTION

The invention relates to the treatment of Pulmonary Hypertension with heart failure with preserved ejection fraction (PH-HFpEF). More specifically, embodiments of the invention provide compositions and methods useful for the treatment of PH-HFpEF, employing the use of levosimendan, or OR1896, or OR1855. In other embodiments, the treatment of PH-HFpEF through subcutaneous administration is contemplated. In other embodiments, the treatment of PH-HFpEF through oral administration is contemplated. In other embodiments, the treatment of PH-HFPEF through combination therapy of levosimendan, or OR1896, or OR1855 and other cardiovascular drugs is contemplated.

The invention provides levosimendan and medicaments comprising levosimendan for use in any of the methods of the invention.

Other objects, features and advantages of the present invention will become clear from the following description and drawings.

BRIEF DESCRIPTION OF THE DRAWINGS

FIGS. 1A-1B are graphical representations of Example 1 results, showing a decrease in pulmonary capillary wedge pressure (PCWP) after levosimendan administration in 30 patients. These results are based on single 24-hour open label lead-in infusion data. FIG. 1A shows the decrease in PCWP after levosimendan infusion during rest with the human subjects' legs down. FIG. 1B shows the decrease in PCWP after levosimendan infusion during exercise where the human subject exerts 25 watts.

FIG. 2A shows the decrease in RAP after levosimendan infusion during rest with the human subjects' legs down. FIG. 2B shows the decrease in RAP after levosimendan infusion during exercise where the human subject exerts 25 watts.

FIGS. 3A-3B are graphical representations of Example 1 results, showing a decrease in mean pulmonary artery pressure (mPAP) after levosimendan administration in 30 patients. These results are based on single 24-hour open label lead-in infusion data. Panel A shows the decrease in mPAP after levosimendan infusion during rest with the human subjects' legs down. Panel B shows the decrease in mPAP after levosimendan infusion during exercise where the human subject exerts 25 watts.

FIGS. 4A-4B are graphical representations of Example results, showing an increase in cardiac output (CO) after levosimendan administration in 30 patients. These results are based on single 24-hour open label lead-in infusion data. Panel A shows the increase in CO after levosimendan infusion during rest with the human subjects' legs down. Panel B shows the increase in CO after levosimendan infusion during exercise where the human subject exerts 25 watts.

FIG. 5 is a graphical representation of Example 2 results, showing an increase in 6-minute walk distance after levosimendan administration in 8 patients.

FIG. 6 is a graphical representation of Example 2 results, showing an increase in quality of life assessment after levosimendan administration according to the 5 Point Likert Scale in 8 patients.

FIG. 7 is a graphical representation of Example 1 results, showing a predictor of response for PH-HFpEF patients treated with levosimendan in 21 patients. The graph indicates that the greater the change in a patient's stroke volume between rest and 25 watts of exercise, the greater the reduction in PCWP after administration of levosimendan.

FIG. 8 is a graphical representation of Example 2 results, showing a decrease in pulmonary capillary wedge pressure (PCWP) after levosimendan or placebo was administered via weekly 24-hour IV infusions for a period of 5 weeks to 35 PH-HFpEF patients (18 levosimendan treated and 17 placebo treated patients). The left panel shows the difference in PCWP after placebo administration during rest with the human subjects' legs down, legs raised on a supine bicycle, and during exercise where the human subject exerts 25 watts. The right panel shows the decrease in PCWP after levosimendan infusion during rest with the human subjects' legs down, leg raise on a supine bicycle, and during exercise where the human subject exerts 25 watts. † Tested in a mixed effect model using treatments as factors and position as a random effect.

FIGS. 9A-9C are a graphical representations of Example 2 results, where levosimendan or placebo was administered via weekly 24-hour IV infusions for a period of 5 weeks to 35 PH-HFpEF patients (18 levosimendan treated and 17 placebo treated patients), showing a larger decrease in PCWP after levosimendan administration in 18 PH-HFpEF patients compared to placebo administration in 17 additional PH-HFpEF patients. FIG. 9A shows the decrease in PCWP after levosimendan infusion and placebo infusion during rest with the human subjects' legs down. FIG. 9B shows the decrease in PCWP after levosimendan infusion and placebo infusion with the patients' legs up in a supine position. FIG. 9C shows the decrease in PCWP after levosimendan infusion and placebo infusion during exercise where the human subject exerts 25 watts.

FIG. 10 is a graphical representation of Example 2 results, where levosimendan or placebo was administered via weekly 24-hour IV infusions for a period of 5 weeks to 35 PH-HFpEF patients (18 levosimendan treated and 17 placebo treated patients), showing a decrease in PCWP after levosimendan administration in 18 PH-HFpEF patients.

FIG. 11 is a graphical representation of Example 2 results, where levosimendan or placebo was administered via weekly 24-hour IV infusions for a period of 5 weeks to 35 PH-HFpEF patients (18 levosimendan treated and 17 placebo treated patients), showing a decrease in right atrial pressure (RAP) after levosimendan administration in 18 PH-HFpEF patients compared to 17 placebo treated patients. The figure shows the decrease in RAP during rest with the human subjects' legs down, legs raised on a supine bicycle, and during exercise where the human subject exerts 25 watts.

FIGS. 12A-12C are graphical representations of Example 2 results, where levosimendan or placebo was administered via weekly 24-hour W infusions for a period of 5 weeks to 35 PH-HFpEF patients (18 levosimendan treated and 17 placebo treated patients), showing a larger decrease in RAP after levosimendan administration in 18 PH-HFpEF patients compared to placebo administration in 17 additional PH-HFpEF patients. FIG. 12A shows the decrease in RAP after levosimendan infusion and placebo infusion during rest with the human subjects' legs down. FIG. 12B shows the decrease in RAP after levosimendan infusion and placebo infusion with the patients' legs up in a supine position. FIG. 12C shows the decrease in RAP after levosimendan infusion and placebo infusion during exercise where the human subject exerts 25 watts.

FIG. 13 is a graphical representation of Example 2 results, where levosimendan or placebo was administered via weekly 24-hour W infusions for a period of 5 weeks to 35 PH-HFpEF patients, showing a decrease in mean pulmonary artery pressure (mPAP) after levosimendan administration in 18 PH-HFpEF patients compared to 17 placebo treated patients. The figure shows the decrease in mPAP during rest with the human subjects' legs down, legs raised on a supine bicycle, and during exercise where the human subject exerts 25 watts.

FIGS. 14A-14C are graphical representations of Example 2 results, where levosimendan or placebo was administered via weekly 24-hour IV infusions for a period of 5 weeks to 35 PH-HFpEF patients, showing a larger decrease in mPAP after levosimendan administration in 18 PH-HFpEF patients compared to placebo administration in 17 additional PH-HFpEF patients. FIG. 14A shows the decrease in mPAP after levosimendan infusion and placebo infusion during rest with the human subjects' legs down. FIG. 14B shows the decrease in mPAP after levosimendan infusion and placebo infusion with the patients' legs up in a supine position. FIG. 14C shows the decrease in mPAP after levosimendan infusion and placebo infusion during exercise where the human subject exerts 25 watts.

FIG. 15 is a graphical representation of Example 2 results, where levosimendan or placebo was administered via weekly 24-hour IV infusions for a period of 5 weeks to 35 PH-HFpEF patients, showing an increase in 6-minute walk distance after levosimendan administration in 18 PH-HFpEF patients compared to placebo administration in 17 additional PH-HFpEF patients.

FIG. 16: Treatment Emergent Adverse Events. FIG. 16 shows results of Example 2, where levosimendan or placebo was administered via weekly 24-hour IV infusions for a period of 5 weeks to 36 PH-HFpEF patients, showing a comparison of Treatment Emergent Adverse Events (TEAEs) after levosimendan administration in 18 PH-HFpEF patients compared to placebo administration in 18 additional PH-HFpEF patients.

FIG. 17: Treatment Emergent Adverse Events (Incidence of two or more). FIG. 17 shows results of Example 2, where levosimendan or placebo was administered via weekly 24-hour IV infusions for a period of 5 weeks to 36 PH-HFpEF patients, showing a comparison of specific Treatment Emergent Adverse Events (TEAEs) after levosimendan administration in 18 PH-HFpEF patients compared to placebo administration in 18 additional PH-HFpEF patients.

FIG. 18: Serious Adverse Events. FIG. 18 shows results of Example 2, where levosimendan or placebo was administered via weekly 24-hour IV infusions for a period of 5 weeks to 36 PH-HFpEF patients, showing Serious Adverse Events, and the Relatedness/Change in Dose of levosimendan.

FIG. 19 is a graphical representation of Example 2 results, where levosimendan or placebo was administered via weekly 24-hour IV infusions for a period of 5 weeks to 36 PH-HFpEF patients, showing OR1896 trough blood levels at final RHC in levosimendan treated patients.

FIG. 21A shows impact on CVP. FIG. 21B shows impact on PCWP. In both FIGS. 21-21B, 'Baseline' measurements are shown to the left of "24 Hours' measurements.

FIG. 22: Baseline Characteristics among randomized patients.

FIG. 23: Summary of Overall Hemodynamic Effects of 24-hour Levosimendan Infusion. FIG. 23 shows the acute (24 hours) effects of open-label levosimendan (n=44). 85% of patients exhibited a ≥4 mmHg decrease of PCWP. Abbreviations: HR heart rate; CVP, central venous pressure; PAS, pulmonary artery systolic pressure; PAD, pulmonary artery diastolic pressure; PA, pulmonary artery; PCWP, pulmonary capillary wedge pressure; AoS, arterial systolic pressure; CI, cardiac index; SVR, systemic vascular resistance; PVR, pulmonary vascular resistance. *p<0.05 compared to baseline.

FIG. 24: Baseline and 6 weeks hemodynamic parameters values for all randomized patients (n=18 placebo and 17 levosimendan treatment patients). Least squares (LS) means and confidence intervals (CI) are from analysis of variance (ANOVA) model for change from baseline with treatment group as a factor. †Between group differences p=0.04 by mixed effects mixed effect repeated measures model. Abbreviations: HR heart rate: CVP, central venous pressure; PAS, pulmonary artery systolic pressure; PAD, pulmonary artery diastolic pressure; PA, pulmonary artery: PCWP, pulmonary capillary wedge pressure; AoS, arterial systolic pressure; CI, cardiac index; SVR, systemic vascular resistance; PVR, pulmonary vascular resistance.

DETAILED DESCRIPTION OF THE INVENTION

Figure 1A:
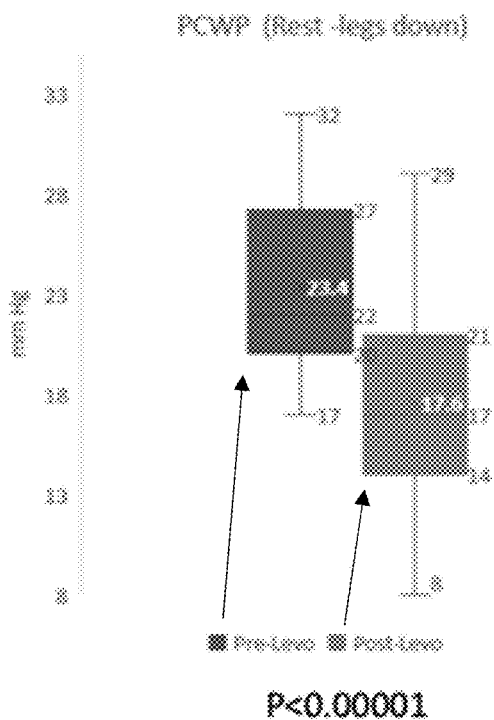
FIGS. 1A-1B: Pulmonary Capillary Wedge Pressure (PCWP) Pre vs Post Levosimendan Lead-in Infusion Open-Label Levosimendan Responders (n=30).

According to some embodiments, the invention provides a method for treating Pulmonary Hypertension Heart Failure with preserved ejection fraction (PH-HFpEF) in a human subject afflicted with PH-HFpEF comprising administering to the human subject an amount of levosimendan, its metabolites OR-1896 or OR-1855, or a combination thereof, that is effective to treat the PH-HFpEF in the human subject.

In some embodiments, the treating comprises a reduction in the human subject's pulmonary capillary wedge pressure at rest.

In some embodiments, the treating comprises a reduction in the human subject's pulmonary capillary wedge pressure at rest by 1 to 30 mmHg.

In some embodiments, the treating comprises stabilization of the human subject's pulmonary capillary wedge pressure at rest at 5 to 35 mmHg.

In some embodiments, the treating comprises stabilization of the human subject's pulmonary capillary wedge pressure at rest at 10 to 35 mmHg.

In some embodiments, the treating comprises a reduction in the human subject's pulmonary capillary wedge pressure during exercise by the human subject.

In some embodiments, the treating comprises a reduction in the human subject's pulmonary capillary wedge pressure during exercise by the human subject by 1 to 40 mmHg.

In some embodiments, the treating comprises stabilization of the human subject's pulmonary capillary wedge pressure during exercise by the human subject at 10 to 50 mmHg.

In some embodiments, the treating does not comprise a significant change in pulmonary capillary wedge pressure during exercise by the human subject.

In some embodiments, the treating comprises a reduction in the human subject's pulmonary capillary wedge pressure when the human subject's legs are elevated.

In some embodiments, the treating comprises a reduction in the human subject's pulmonary capillary wedge pressure when the human subject's legs are elevated and the reduction is 1 to 30 mmHg.

In some embodiments, the treating comprises stabilization of the human subject's pulmonary capillary wedge pressure when the human subject's legs are elevated and the stabilization is at 10 to 50 mmHg.

In some embodiments, the treating comprises a reduction in the human subject's right atrial pressure at rest.

In some embodiments, the treating comprises a reduction in the human subject's right atrial pressure at rest by 1 to 30 mmHg.

In some embodiments, the treating comprises stabilization of the human subject's right atrial pressure at rest at 1 to 30 mmHg.

In some embodiments, the treating comprises stabilization of the human subject's right atrial pressure at rest at 5 to 30 mmHg.

In some embodiments, the treating comprises a reduction in the human subject's right atrial pressure during exercise by the human subject.

In some embodiments, the treating comprises a reduction in the human subject's right atrial pressure during exercise by the human subject by 1 to 30 mmHg.

In some embodiments, the treating comprises stabilization of the human subject's right atrial pressure during exercise by the human subject at 5 to 40 mmHg.

In some embodiments, the treating comprises a reduction in the human subject's right atrial pressure when the human subject's legs are elevated.

In some embodiments, the treating comprises a reduction in the human subject's mean pulmonary artery pressure at rest.

In some embodiments, the treating comprises a reduction in the human subject's mean pulmonary artery pressure at rest by 1 to 30 mmHg.

In some embodiments, the treating comprises stabilization of the human subject's mean pulmonary artery pressure at rest at 15 to 65 mmHg.

In some embodiments, the treating comprises a reduction in the human subject's mean pulmonary artery pressure during exercise by the human subject.

In some embodiments, the treating comprises a reduction in the human subject's mean pulmonary artery pressure during exercise by the human subject by 1 to 30 mmHg.

In some embodiments, the treating comprises stabilization of the human subject's mean pulmonary artery pressure during exercise by the human subject at 25 to 85 mmHg.

In some embodiments, the treating comprises stabilization of the human subject's mean pulmonary artery pressure during exercise by the human subject at 25 to 80 mmHg.

In some embodiments, the treating comprises a reduction in the human subject's mean pulmonary artery pressure when the human subject's legs are elevated.

In some embodiments, the treating comprises an increase in the human subject's cardiac output at rest.

In some embodiments, the treating comprises an increase in the human subject's cardiac output at rest by 0.01 to 3 liters/min.

In some embodiments, the treating comprises stabilization of the human subject's cardiac output at rest at 2 to 10 liters/min.

In some embodiments, the treating comprises an increase in the human subject's cardiac output during exercise by the human subject.

In some embodiments, the treating comprises an increase in the human subject's cardiac output during exercise by the human subject by 0.01 to 5 liters/min.

In some embodiments, the treating comprises an increase in the human subject's cardiac output during exercise by the human subject by 0.01 to 4 liters/min.

In some embodiments, the treating comprises stabilization of the human subject's cardiac output during exercise by the human subject at 3.0 to 15.0 liters/min.

In some embodiments, the treating does not comprise a significant increase in the human subject's heart rate.

In some embodiments, the treating does not comprise an increase in the human subject's heart rate of more than 10 beats/min.

In some embodiments, the treating comprises an improvement in the human subject's quality of life.

In some embodiments, the improvement in the human subject's quality of life is measured by a patient reported outcome assessment tool.

In some embodiments, the improvement in the human subject's quality of life is measured by a Likert scale that is a five (5) point patient reported outcome assessment tool In some embodiments, the treating comprises an improvement in the human subject's quality of life according to a change in the human subject's patient reported outcome assessment tool score of at least 1.

In some embodiments, the treating comprises an improvement in the human subject's quality of life according to a change in the human subject's patient reported outcome assessment tool score of at least 2.

In some embodiments, the treating comprises an improvement in the human subject's six (6) minute walk distance.

In some embodiments, the treating comprises an improvement in the human subject's six (6) minute walk distance of 5 to 150 meters.

In some embodiments, the treating comprises an improvement in the physician's assessment of the human subject's functional class.

In some embodiments, the treating comprises a reduction in the incidence of hospitalization for heart failure.

In some embodiments, the treating comprises a reduction in all-cause mortality.

In some embodiments, the treating comprises an improvement in right heart failure and/or right ventricular dysfunction.

In some embodiments, the improvement is evidenced by a reduction in right atrial pressure at rest and during 25 watts of exercise.

In some embodiments, the human subject is a responder to levosimendan therapy.

In some embodiments, a responder to levosimendan therapy is a human subject whose pulmonary capillary wedge pressure decreases by at least 4 mmHG during bicycle exercise at 25 watts following the initial infusion.

In some embodiments, a responder to levosimendan therapy is a human subject whose cardiac index decreases by no more than 10% between the baseline measurements and repeated measurements following the initial infusion.

In some embodiments, the human subject is a responder to levosimendan therapy if the human subject has cardiac reserve.

In some embodiments, the human subject is a responder to levosimendan therapy if the human subject's stroke volume increases during exercise by the human subject.

In some embodiments, the human subject is a responder to levosimendan therapy if the human subject's stroke volume increases during exercise by the human subject when determined with a catheter in the human subject's heart measuring the blood moving out of the left ventricle with every beat.

In some embodiments, the human subject is a responder to levosimendan therapy if the human subject's stroke volume increases during exercise by the human subject when estimated with an electrocardiogram and/or echocardiogram.

In some embodiments, the human subject is a responder to levosimendan therapy if the human subject's stroke volume increases during exercise by the human subject when determined with a dobutamine stress test.

In some embodiments, the human subject is a responder to levosimendan therapy if the human subject's stroke volume increases during exercise by the human subject by at least 0.005 liters.

In some embodiments, the human subject is a responder to levosimendan therapy if the human subject's stroke volume increases during exercise by the human subject by 1 to 50 mL when determined with a catheter in the human subject's heart measuring the blood moving out of the left ventricle with every beat.

In some embodiments, the human subject is a responder to levosimendan therapy if the human subject's stroke volume increases during exercise by the human subject by 1 to 50 mL when estimated with an echocardiogram, right heart catheterization, or other means.

In some embodiments, the human subject is a responder to levosimendan therapy if the human subject's stroke volume increases during exercise by the human subject by 1 to 50 mL when determined with a dobutamine stress test.

In some embodiments, the human subject afflicted with PH-HFpEF has a left ventricular ejection fraction of at least 40%.

In some embodiments, the human subject afflicted with PH-HFpEF has a baseline pulmonary arterial pressure of at least 35.

In some embodiments, the human subject afflicted with PH-HFpEF has a baseline pulmonary capillary wedge pressure of at least 20.

In some embodiments, the human subject afflicted with PH-HFpEF is classified as classification IIb by the physician's assessment of New York Heart Association Classification.

In some embodiments, the human subject afflicted with PH-HFpEF is classified as classification III by the physician's assessment of New York Heart Association Classification.

In some embodiments, the human subject afflicted with PH-HFpEF has the ability to walk at least 50 meters in a six-minute walk test.

In some embodiments, the human subject afflicted with PH-HFpEF does not have the ability to walk more than 550 meters in a six-minute walk test.

In some embodiments, the human subject afflicted with PH-HFpEF has the ability to walk at least 50 meters, but not more than 550 meters, in a six-minute walk test.

In some embodiments, the human subject afflicted with PH-HFpEF is not afflicted with heart failure with reduced ejection fraction.

In some embodiments, the human subject afflicted with PH-HFpEF is not afflicted with heart failure with preserved ejection fraction without pulmonary hypertension.

In some embodiments, the human subject afflicted with PH-HFpEF has a primary diagnosis of Group 2 PH-HFpEF.

In some embodiments, the human subject afflicted with PH-HFpEF is not afflicted with coronary artery disease.

In some embodiments, the human subject afflicted with PH-HFpEF has not had previous percutaneous coronary intervention.

In some embodiments, the human subject afflicted with PH-HFpEF has not had previous percutaneous coronary intervention, unless the human subject has had a negative stress test within the last year.

In some embodiments, the human subject afflicted with PH-HFpEF has not had previous cardiac surgery.

In some embodiments, the human subject afflicted with PH-HFpEF has not had previous cardiac surgery, unless the human subject has had a negative stress test within the last year.

In some embodiments, the human subject afflicted with PH-HFpEF is not afflicted with congenital heart disease.

In some embodiments, the human subject afflicted with PH-HFpEF is not afflicted with a clinically significant lung disease.

In some embodiments, the human subject afflicted with PH-HFpEF does not have a planned heart or lung surgery.

In some embodiments, the human subject afflicted with PH-HFpEF does not have a cardiac index greater than 4.0 L/min/m2.

In some embodiments, the human subject afflicted with PH-HFpEF does not concomitantly receive pulmonary vasodilator therapy.

In some embodiments, the human subject afflicted with PH-HFpEF has not received pulmonary vasodilator therapy within the last 14 days.

In some embodiments, the human subject afflicted with PH-HFpEF does not receive dialysis treatment.

In some embodiments, the human subject afflicted with PH-HFpEF does not have a Glomerular Filtration Rate less than 30 mL/min/1.73 m2.

In some embodiments, the human subject afflicted with PH-HFpEF does not have liver dysfunction with Child Pugh Class B or C.

In some embodiments, the human subject afflicted with PH-HFpEF does not have evidence of systemic infection.

In some embodiments, the human subject afflicted with PH-HFpEF does not weigh more than 150 kg.

In some embodiments, the human subject afflicted with PH-HFpEF can manage their symptomatic systolic blood pressure to ensure it is greater than 100 mmHg.

In some embodiments, the human subject afflicted with PH-HFpEF does not have a heart rate greater than or equal to 100 beats per minute with the drug.

In some embodiments, the human subject afflicted with PH-HFpEF does not have a heart rate greater than or equal to 100 beats per minute with the drug that is symptomatic and persistent for at least 10 minutes.

In some embodiments, the human subject afflicted with PH-HFpEF does not have hemoglobin less than 80 g/L.

In some embodiments, the human subject afflicted with PH-HFpEF does not have serum potassium less than 3.0 mmol/L at baseline.

In some embodiments, the human subject afflicted with PH-HFpEF does not have serum potassium greater than 5.5 mmol/L at baseline.

In some embodiments, the human subject afflicted with PH-HFpEF does not have serum potassium less than 3.0 mmol or greater than 5.5 mmol/L at baseline.

In some embodiments, the human subject afflicted with PH-HFpEF does not have severely compromised immune function.

In some embodiments, the human subject afflicted with PH-HFpEF is not pregnant.

In some embodiments, the human subject afflicted with PH-HFpEF is not suspected to be pregnant, In some embodiments, the human subject afflicted with PH-HFpEF is not breast-feeding.

In some embodiments, the human subject afflicted with PH-HFpEF is a patient with Biventricular Failure.

In some embodiments, the administration is self-administered by the human subject.

In some embodiments, the self-administration takes place in a hospital by the human subject.

In some embodiments, the self-administration takes place in an outpatient-setting by the human subject.

In some embodiments, the self-administration takes place outside of a hospital by the human subject.

In some embodiments, the self-administration takes place at home by the human subject.

In some embodiments, the administration is not self-administered by the human subject.

In some embodiments, the administration is administered by a trained professional.

In some embodiments, the administration takes place in a hospital by the trained professional.

In some embodiments, the administration takes place in an outpatient-setting by the trained professional.

In some embodiments, the administration takes place outside of a hospital by the trained professional.

In some embodiments, the administration takes place at home by the trained professional.

In some embodiments, the administration is delivered via IV administration.

In some embodiments, the IV administration accesses the vein through a PICC line.

In some embodiments, the IV administration accesses the vein through a Port-a-cath.

In some embodiments, the administration takes place intermittently.

In some embodiments, the administration takes place weekly.

In some embodiments, the administration is given via a 24-hour infusion.

In some embodiments, the administration is given via a weekly 24-hour infusion.

In some embodiments, the administration takes place chronically.

In some embodiments, the administration is chronic administration given via a less than 24-hour infusion.

In some embodiments, the administration is a dose of levosimendan 2.5 mg/mL infusion concentrate that includes levosimendan, povidone, citric acid, and ethanol.

In some embodiments, the administration is a dose of levosimendan 2.5 mg/mL infusion concentrate that includes levosimendan, povidone, citric acid, and ethanol and is supplied in 5 mL of total volume.

In some embodiments, the administration is a dose of levosimendan 2.5 mg/mL infusion concentrate that includes levosimendan, povidone, citric acid, and ethanol and is supplied in 5 mL of total volume that is added to one 250 mL infusion bag of 5% Dextrose.

In some embodiments, the administration is a dose of levosimendan 2.5 mg/mL infusion concentrate that includes levosimendan, povidone, citric acid, and ethanol and is supplied in 5 mL of total volume that is added to one 250 mL infusion bag of 0.9 Normal Saline.

In some embodiments, the administration is a dose of levosimendan 2.5 mg/mL infusion concentrate that includes levosimendan, povidone, citric acid, and ethanol and is supplied in 5 mL of total volume that is added to one 250 mL infusion bag of 5% Dextrose or 0.9 Normal Saline where the human subject weights less than 85 kg.

In some embodiments, the administration is a dose of levosimendan 2.5 mg/mL infusion concentrate that includes levosimendan, povidone, citric acid, and ethanol and is supplied in 10 mL of total volume.

In some embodiments, the administration is a dose of levosimendan 2.5 mg/mL infusion concentrate that includes levosimendan, povidone, citric acid, and ethanol and is supplied in 10 mL of total volume that is added to one 500 mL infusion bag of 5% Dextrose.

In some embodiments, the administration is a dose of levosimendan 2.5 mg/mL infusion concentrate that includes levosimendan, povidone, citric acid, and ethanol and is supplied in 10 mL of total volume that is added to one 500 mL infusion bag of 0.9 Normal Saline.

In some embodiments, the administration is a dose of levosimendan 2.5 mg/mL infusion concentrate that includes levosimendan, povidone, citric acid, and ethanol and is supplied in 10 mL of total volume that is added to one 500 mL infusion bag of 5% Dextrose or 0.9 Normal Saline where the human subject weights at least 85 kg.

In some embodiments, the administration lead-in infusion rate is 0.10 µg/kg/min for 24 hours.

In some embodiments, the administration week 2 infusion rate is 0.075 µg/kg/min for 24 hours.

In some embodiments, the administration week 3 infusion rate is 0.075 µg/kg/min for 24 hours.

In some embodiments, the administration week 4 infusion rate is 0.10 µg/kg/min for 24 hours.

In some embodiments, the administration week 5 infusion rate is 0.10 µg/kg/min for 24 hours.

In some embodiments, the administration infusion rate is reduced to 0.05 µg/kg/min when the higher dose is not well-tolerated by the human subject.

In some embodiments, the administration is via oral dosing.

In some embodiments, the oral dosing comprises an immediate release formulation.

In some embodiments, the oral dosing comprises an extended-release formulation.

In some embodiments, the administration is via inhaled delivery.

In some embodiments, the inhaled delivery comprises an inhaled formulation.

In some embodiments, the administration is via transdermal delivery.

In some embodiments, the transdermal delivery comprises a transdermal formulation.

In some embodiments, the administration is subcutaneous administration.

In some embodiments, the administration is subcutaneous administration via a subcutaneous drug delivery device.

In some embodiments, the drug delivery device is a Continuous ambulatory delivery device (CADD) pump.

In some embodiments, the subcutaneous administration comprises administration of a subcutaneous formulation.

In some embodiments, the subcutaneous formulation is the intravenous formulation with additives.

In some embodiments, the subcutaneous formulation comprises 12.5 mg of levosimendan in a non-aqueous formulation that is added to 150 mL of 5% Dextrose, 0.9 Normal Saline, or other pharmaceutically acceptable diluent or carrier to create a levosimendan concentration of 0.0833 mg/mL in the subcutaneous formulation.

In some embodiments, the subcutaneous formulation comprises 12.5 mg of levosimendan in a non-aqueous formulation that is added to 250 mL of 5% Dextrose, 0.9 Normal Saline, or other pharmaceutically acceptable diluent or carrier to create a levosimendan concentration of 0.05 mg/mL in the subcutaneous formulation.

In some embodiments, the subcutaneous formulation comprises 12.5 mg of levosimendan in a non-aqueous formulation that is added to 500 mL of 5% Dextrose, 0.9 Normal Saline, or other pharmaceutically acceptable diluent or carrier to create a levosimendan concentration of 0.025 mg/mL in the subcutaneous formulation.

In some embodiments, the subcutaneous formulation comprises 12.5 mg of levosimendan in a non-aqueous formulation that is added to 1000 mL of 5% Dextrose, 0.9 Normal Saline, or other pharmaceutically acceptable diluent or carrier to create a levosimendan concentration of 0.0125 mg/mL in the subcutaneous formulation.

In some embodiments, the subcutaneous formulation comprises 12.5 mg of levosimendan in a non-aqueous formulation that is added to 1500 mL of 5% Dextrose, 0.9 Normal Saline, or other pharmaceutically acceptable diluent or carrier to create a levosimendan concentration of 0.008333 mg/mL in the subcutaneous formulation.

In some embodiments, the subcutaneous administration of the subcutaneous formulation comprises water in an amount effective to reduce pain caused by the subcutaneous administration.

In some embodiments, the subcutaneous administration of the subcutaneous formulation comprises buffers to raise the pH higher than 3.5.

In some embodiments, the subcutaneous administration of the subcutaneous formulation has reduced side effects relative to intravenous administration of levosimendan in the human subject.

In some embodiments, the subcutaneous administration of the subcutaneous formulation reduces peak plasma concentrations of levosimendan relative to intravenous administration in the human subject.

In some embodiments, the subcutaneous administration of the subcutaneous formulation reduces peak plasma concentrations of levosimendan relative to intravenous administration in the human subject by at least 1% to 25%.

In some embodiments, the amount of levosimendan its metabolites OR-1896 or OR-1855, or a combination thereof, is administered in combination with a cardiovascular drug.

In some embodiments, an amount of levosimendan its metabolites OR-1896 or OR-1855, or a combination thereof, and an amount of the cardiovascular drug, wherein the amounts when taken together are effective to treat the human subject, are periodically adminstered to the human subject.

In some embodiments, the amount of levosimendan its metabolites OR-1896 or OR-1855, or a combination thereof, and the amount of the cardiovascular drug when administered together is more effective to treat the subject than when each agent at the same amount is administered alone.

In some embodiments, the amount of levosimendan its metabolites OR-1896 or OR-1855, or a combination thereof, and the amount of the cardiovascular drug when taken together is effective to reduce the symptoms of PH-HFpEF.

In some embodiments, the cardiovascular drug is a drug used to treat pulmonary arterial hypertension (PAH), World Health Organization (WHO) Groups 1-5 pulmonary hypertension patients, coronary artery disease (CAD), or heart failure with reduced ejection fraction (HFrEF).

In some embodiments, the cardiovascular drug is a PDE inhibitor, a phosphodiesterase-5 (PDE5) inhibitor, an endothelin receptor antagonist (ERA), a prostanoid, a soluble guanylate cyclase stimulator, a nitrate, a nitrite, an NO donor, a calcium channel blocker (CCB), a fatty acid oxidation inhibitor, a beta-blocker (BB), an angiotensin-converting enzyme (ACE) inhibitor, a neprilysin inhibitor, a neprilysin and angiotensin receptor blocker (ANRI), an angiotensin II receptor blocker (ARB), a diuretic, an aldosterone antagonist, digoxin, ivabradine, hydralazine, seralaxin, a natriuretic peptide, an atrial natriuretic peptide (ANP), a natriuretic peptide, a K-ATP channel activator, a NEP inhibitor, or a prostacyclin.

In some embodiments, the cardiovascular drug is a pulmonary vasodilator drug.

In some embodiments, the pulmonary vasodilator is a phosphodiesterase-5 (PDE5) inhibitor, an endothelin receptor antagonist (ERA), or a prostacyclin.

In some embodiments, the amount of levosimendan, its metabolites OR-1896 or OR-1855, or a combination thereof, administered in combination with the pulmonary vasodilator drug is administered to a human subject afflicted with pre and post capillary pulmonary hypertension and heart failure with preserved ejection fraction (Cpc-PH-HFpEF).

In some embodiments, no arrythmias, atrial or ventricular, are observed when comparing baseline electrocardiographic monitoring with 72-hour monitoring after 5 weeks of treatment.

In some embodiments, weekly 24-hour dosing of levosimendan is safe and well tolerated.

In some embodiments, treating presents no more statistically significant adverse events than the matching placebo.

In some embodiments, the weekly 24-hour dosing of levosimendan results in steady state blood levels of OR1896 in the range of 0.20 ng/mL to 25.00 ng/mL.

According to some embodiments, the invention also provides an article of manufacture comprising:

a. a 5 mL vial dose of levosimendan 2.5 mg/mL infusion concentrate that includes levosimendan, povidone, citric acid, and ethanol;

b. 250 mL of 5% Dextrose or 0.9 Normal Saline; and
c. a buffer for increasing pH.

According to some embodiments, the invention also provides use of an amount of levosimendan, its metabolites OR-1896 or OR-1855, or a combination thereof, to effectively treat Pulmonary Hypertension Heart Failure with preserved ejection fraction (PH-HFpEF) in a human subject.

According to some embodiments, the invention also provides use of an amount of levosimendan, its metabolites OR-1896 or OR-1855, or a combination thereof, for preparing medicament for administering to a human subject afflicted with Pulmonary Hypertension Heart Failure with preserved ejection fraction (PH-HFpEF to effectively treat PH-HFpEF in the human subject.

According to some embodiments, the invention also provides a medicament comprising an amount of levosimendan, its metabolites OR-1896 or OR-1855, or a combination thereof, for use in effectively treating Pulmonary Hypertension Heart Failure with preserved ejection fraction (PH-HFpEF) in a human subject.

According to some embodiments, the invention also provides use of an amount of levosimendan, its metabolites OR-1896 or OR-1855, or a combination thereof, in combination with a cardiovascular drug to effectively treat Pulmonary Hypertension Heart Failure with preserved ejection fraction (PH-HFpEF) in a human subject.

According to some embodiments, the invention also provides use of an amount of levosimendan, its metabolites OR-1896 or OR-1855, or a combination thereof, for preparing a medicament in combination with a cardiovascular drug for administering to a human subject afflicted with Pulmonary Hypertension Heart Failure with preserved ejection fraction (PH-HFpEF) to effectively treat PH-HFpEF in the human subject.

According to some embodiments, the invention also provides a medicament comprising an amount of levosimendan, its metabolites OR-1896 or OR-1855, or a combination thereof, for use in combination with a cardiovascular drug to effectively treat Pulmonary Hypertension Heart Failure with preserved ejection fraction (PH-HFpEF) in a human subject.

According to some embodiments, the invention also provides a subcutaneous formulation of levosimendan for use in treating PH-HFpEF in a human subject afflicted with PH-HFpEF, wherein the subcutaneous formulation is obtained from a dried powder, wherein the dried powder is obtained from a pharmaceutical composition comprising: (a) levosimendan; (b) sulfo-butyl-ether beta-cyclodextrin; (c) sodium hydroxide or acetic acid; and water for injection.

In some embodiments, the amount of levosimendan is 2.5 mg/ml water for injection.

In some embodiments, the amount of sulfo-butyl-ether beta-cyclodextrin is 0.175 mg/ml water for injection.

In some embodiments, the sodium hydroxide or acetic acid is in a suitable amount to adjust the pH to a range of 7.2 to 7.8.

In some embodiments, the pharmaceutical composition is filter sterilized.

In some embodiments, the pharmaceutical composition is lyophilized.

In some embodiments, subcutaneous formulation of levosimendan is obtained from the dried powder by reconstitution of the dried powder in an amount of aqueous solution suitable for subcutaneous administration.

In some embodiments, the reconstituted subcutaneous formulation is pH adjusted to 7.2 to 7.8 with sodium hydroxide or acetic acid.

According to some embodiments, the invention provides a method for treating Pulmonary Hypertension Heart Failure with preserved ejection fraction (PH-HFpEF) in a human subject afflicted with PH-HFpEF comprising administering to the human subject an amount of a cardiovascular drug that is effective to treat the PH-HFpEF in the human subject, wherein the cardiovascular drug is selected from the group consisting of a PDE inhibitor, a phosphodiesterase-5 (PDE5) inhibitor, an endothelin receptor antagonist (ERA), a prostanoid, a soluble guanylate cyclase stimulator, a nitrate, a nitrite, an NO donor, a calcium channel blocker (CCB), a fatty acid oxidation inhibitor, a beta-blocker (BB), an angiotensin-converting enzyme (ACE) inhibitor, a neprilysin inhibitor, a neprilysin and angiotensin receptor blocker (ANRI), an angiotensin II receptor blocker (ARB), a diuretic, an aldosterone antagonist, digoxin, ivabradine, hydralazine, seralaxin, a natriuretic peptide, an atrial natriuretic peptide (ANP), a natriuretic peptide, a K-ATP channel activator, a NEP inhibitor, and a prostacyclin.

According to some embodiments, the invention provides a method for treating Pulmonary Hypertension Heart Failure with preserved ejection fraction (PH-HFpEF) in a human subject afflicted with PH-HFpEF comprising administering to the human subject an amount of a pulmonary vasodilator drug that is effective to treat the PH-HFpEF in the human subject, wherein the pulmonary vasodilator drug is selected from the group consisting of a phosphodiesterase-5 (PDE5) inhibitor, an endothelin receptor antagonist (ERA), and a prostacyclin.

In some embodiments, the amount of the pulmonary vasodilator drug is administered to a human subject afflicted with pre and post capillary pulmonary hypertension and heart failure with preserved ejection fraction (Cpc-PH-HFpEF).

According to some embodiments, the invention provides a cardiovascular drug for use in treating Pulmonary Hypertension Heart Failure with preserved ejection fraction (PH-HFpEF) in a subject, wherein the cardiovascular drug is selected from the group consisting of a PDE inhibitor, a phosphodiesterase-5 (PDE5) inhibitor, an endothelin receptor antagonist (ERA), a prostanoid, a soluble guanylate cyclase stimulator, a nitrate, a nitrite, an NO donor, a calcium channel blocker (CCB), a fatty acid oxidation inhibitor, a beta-blocker (BB), an angiotensin-converting enzyme (ACE) inhibitor, a neprilysin inhibitor, a neprilysin and angiotensin receptor blocker (ANRI), an angiotensin II receptor blocker (ARB), a diuretic, an aldosterone antagonist, digoxin, ivabradine, hydralazine, seralaxin, a natriuretic peptide, an atrial natriuretic peptide (ANP), a natriuretic peptide, a K-ATP channel activator, a NEP inhibitor, and a prostacyclin.

According to some embodiments, the invention provides a pulmonary vasodilator drug for use in treating Pulmonary Hypertension Heart Failure with preserved ejection fraction (PH-HFpEF) in a subject, wherein the pulmonary vasodilator drug is selected from the group consisting of a phosphodiesterase-5 (PDE5) inhibitor, an endothelin receptor antagonist (ERA), and a prostacyclin.

In some embodiments, the Pulmonary Hypertension Heart Failure with preserved ejection fraction (PH-HFpEF) is pre and post capillary pulmonary hypertension and heart failure with preserved ejection fraction (Cpc-PH-HFpEF).

In some embodiments, the subject is orally administered a capsule comprising up to 0.1 mg, 0.25 mg, 0.5 mg, 0.75 mg, 1 mg, 2 mg, 3 mg, or 4 mg, more preferably 1-3 mg, of levosimendan, its metabolites OR-1896 or OR-1855, or a combination thereof.

In some embodiments, the subject is administered a capsule once a day for a time period of 1-60 days, preferably 14 days.

In some embodiments, the subject increases the number of capsules taken per day after every time period if the treatment is tolerated by the subject.

In some embodiments, the subject is orally administered between 0.1-10 mg of levosimendan, its metabolites OR-1896 or OR-1855, or a combination thereof, per day, preferably between 1-4 mg of levosimendan, its metabolites OR-1896 or OR-1855, or a combination thereof per day.

In some embodiments, the subject received a final intravenous injection of levosimendan, its metabolites OR-1896 or OR-1855, or a combination thereof at least one day, more preferably at least one week, before beginning oral administration of levosimendan, its metabolites OR-1896 or OR-1855, or a combination thereof.

Throughout this application, where a parameter range is provided, all integers within that range, and tenths and hundredths thereof as appropriate, shall be considered to also be provided and disclosed in this application as being contemplated by the invention. For example, "0.2-5 mg/kg/day" is to be considered as a disclosure of 0.2 mg/kg/day, 0.3 mg/kg/day, 0.4 mg/kg/day, 0.5 mg/kg/day, 0.6 mg/kg/day etc. up to 5.0 mg/kg/day.

According to some embodiments, the compound to be administered (e.g. levosimendan) is in the form of a composition (referred to as the composition of the invention) comprising a therapeutically effective amount of at least one of said compound. As used herein, the term "effective amount" means an amount of compound that is capable of reducing and/or attenuating a disorder or symptom as described herein. The specific dose of a compound administered according to this invention will, of course, be determined by the particular circumstances surrounding the case including, for example, the compound administered, the route of administration, the physiological state of the subject, and the severity of the condition being treated.

Any suitable route may be used to administer the medicament or levosimendan of the invention to a subject.

According to some embodiments, suitable administration routes may be systemic routes. According to some embodiments, administering is administering systemically. According to some embodiments, the composition is formulated for systemic administration.

According to another embodiment, administration systemically is through an enteral route. According to another embodiment, administration through an enteral route is oral administration. According to some embodiments, the composition is formulated for oral administration.

In an embodiment the administration intermittently takes place via 24-hour, weekly administration.

In an embodiment the administration takes place chronically for less than 24 hours.

In an embodiment the dose is levosimendan 2.5 mg/mL infusion concentrate that includes levosimendan, povidone, citric acid, and ethanol and is supplied in 5 mL of total volume that is added to one 250 mL infusion bag of 5% Dextrose, 0.9 Normal Saline, or other diluent where the human subject weights less than 85 kg.

In an embodiment the dose is levosimendan 2.5 mg/mL infusion concentrate that includes levosimendan, povidone, citric acid, and ethanol and is supplied in 10 mL of total volume that is added to one 500 mL infusion bag of 5% Dextrose, 0.9 Normal Saline, or other diluent where the human subject weights at least 85 kg.

In an embodiment the infusion rate is between 0.075 and 0.10 µg/kg/min for 24 hours.

In an embodiment the administration is delivered via oral dosing. The dosing can be an immediate release or extended release formulation.

In an embodiment the administration is delivered via inhalation of an inhaled formulation.

In an embodiment the administration is delivered via transdermal delivery of a transdermal formulation.

In an embodiment the invention is an article of manufacture including the 5 mL vial dose of levosimendan 2.5 mg/mL infusion concentrate that includes levosimendan, povidone, citric acid, and ethanol; 250 mL of 5% Dextrose or 0.9 Normal Saline; and a buffer for increasing pH.

In an embodiment the amount of levosimendan is effective to treat PH-HFpEF in a human subject.

In an embodiment the amount of levosimendan for preparing medicament for administration is effective to treat PH-HFpEF in a human subject.

In an embodiment the medicament has an amount of levosimendan that is effective to treat PH-HFpEF in a human subject.

In an embodiment the amount of levosimendan in combination with a cardiovascular drug is effective to treat PH-HFpEF in a human subject.

In an embodiment the amount of levosimendan in combination with a cardiovascular drug for preparing medicament for administration is effective to treat PH-HFpEF in a human subject.

In an embodiment the medicament has an amount of levosimendan in combination with a cardiovascular drug that is effective to treat PH-HFpEF in a human subject.

In an embodiment no arrythmias, atrial or ventricular, are observed when comparing baseline electrocardiographic monitoring with 72-hour monitoring after 5 weeks of treatment.

In an embodiment the weekly 24-hour dosing of levosimendan results in steady state blood levels of OR1896 in the range of 0.20 ng/mL to 25.00 ng/mL.

Definitions/Abbreviations

As used herein, the term "levosimendan" means levosimendan base or a pharmaceutically acceptable salt thereof. The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the L-tartrate, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

PH is the abbreviation for Pulmonary Hypertension. PH encompasses a heterogeneous group of disorders with the common feature of elevated pulmonary vascular resistance. (Oldroyd et al. 2019)

HFpEF is the abbreviation for heart failure with preserved ejection fraction. HFpEF is when a patient is afflicted with heart failure while their ejection fraction remains ≥40%. (Kelly et al. 2015)

PH-HFpEF is the abbreviation for Pulmonary Hypertension with heart failure with preserved ejection fraction. PH-HFpEF is defined by a high pulmonary artery pressure, high left ventricular end-diastolic pressure and a normal ejection fraction. (Lai et al. 2019)

PCWP is the abbreviation for pulmonary capillary wedge pressure. PCWP is the pressure measured by wedging a pulmonary catheter with an inflated balloon into a small pulmonary arterial branch. PCWP estimates left atrial pressure. (Peacock et al. 2004)

RAP is the abbreviation for right atrial pressure. RAP is the blood pressure in the right atrium of the heart. RAP reflects the amount of blood returning to the heart and the ability of the heart to pump the blood into the arterial system.

mPAP is the abbreviation for mean pulmonary artery pressure. mPAP is generated by the right ventricle ejecting blood into the pulmonary circulation, which acts as a resistance to the output from the right ventricle.

PVR is the abbreviation for pulmonary vascular resistance. PVR refers to the resistance in the arteries that supply blood to the lungs. (Schnur 2017)

CO is the abbreviation for cardiac output. CO is the volume of blood being pumped by the heart per unit time. (Vincent 2008)

CI is the abbreviation for cardiac index. CI is a hemodynamic parameter that relates the cardiac output from the left ventricle in one minute to the body surface area. This measurement relates heart performance to the size of the individual. (Shea 2019)

HR is the abbreviation for heart rate. HR is the speed of the heartbeat measured by the number of contractions of the heart per minute. (Heart.org 2015)

PR is the abbreviation for pulse rate. PR is the measurement of the heart rate. (Heart.org 2015)

BP is the abbreviation for blood pressure. BP is the pressure of circulating blood within the major arterial system of the body. (Brezinski 1990)

6 MWT is the abbreviation for six-minute walk test. 6 MWT is a performance-based test used to measure functional exercise capacity. The 6 MWT measures the distance an individual is able to walk over a total of 6 minutes at a constant and normal pace. (Vandoni et al. 2018)

Likert scale is a psychometric scale commonly involved in research that employs questionnaires. In the below-mentioned clinical trial, a six-question, five-point Likert Scale is provided to patients to assess their quality of life. (HELP clinical trial protocol)

ECG is the abbreviation for echocardiogram. An ECG is a record of a person's heartbeat produced by echocardiography. An ECG is a test that uses high frequency sound waves (ultrasound) to make pictures of your heart. (heart.org 2015)

Dobutamine stress test is a form of ECG where stress is induced on the heart by administering dobutamine into a vein to assess the heart's function and structures. This test mimics the effects of exercise on the heart. (Hawthorne et al. 2012)

New York Heart Association Functional Classification provides a simple way of classifying the extent of heart failure. A patient in Class I has no limitation of physical activity. A patient in Class II has slight limitation of physical activity. A patient in Class III has marked limitation of physical activity. A patient in Class IV is unable to carry on any physical activity without discomfort. In addition to these class numbers based of patient symptoms, every patient is assigned a class letter based on an objective assessment. A patient in Class A has no objective evidence of cardiovascular disease. A patient in Class B has objective evidence of minimal cardiovascular disease. A patient in Class C has objective evidence of moderately severe cardiovascular disease. A patient in Class D has objective evidence of severe cardiovascular disease. (Yancy et al. 2013)

Self-administration is administration of the formulation administered by the human subject afflicted with the disease. (HELP clinical trial protocol)

Outpatient setting is a setting where the patients do not require admittance for overnight care. (World Health Organization 2009)

Trained professional indicates a doctor, nurse, home healthcare nurse, or other person with training and/or experience and/or a license in the medical profession.

TEAEs is the abbreviation for Treatment Emergent Adverse Events. The TEAEs of special interest are hypotension, atrial fibrillation, other significant arrhythmia, resuscitated death stroke. Other TEAEs include, but are not limited to, headache, increased heart rate, fatigue, cardiac failure acute, dyspnea, vascular access site pain, muscle spasm, and hypokalaemia.

SAEs is the abbreviation for Serious Adverse Events. SAEs include, but are not limited to, infections and infestations, device related infection; infections and infestations, bacteremia; cardiac disorders, cardiac failure acute, and cardiac disorders, cardiac failure acute.

As used herein, the term "acute administration" means administration of a drug, e.g. levosimendan, in a brief period of time, for example, delivery of a single dose of a drug, delivery of doses of a drug in rapid succession, or delivery of a drug on short time scale, preferably less than 48 hours. Acute administration of a drug is generally intended for the drug to have a beneficial effect on a condition in the short-term. For example, acute administration of levosimendan may be performed such that the amount of levosimendan administered is intended for the levosimendan drug to directly improve a condition, e.g. PH-HFpEF, prior to any significant activity of a levosimendan metabolite. Acute administration is generally performed by a trained professional, for example, by intravenous administration in a clinical setting.

As used herein, the term "chronic administration" means an extended and repeated administration of a drug, e.g. levosimendan. For example, delivery of multiple or repeated doses of a drug over the course of a long-time scale, preferably at least a week. Chronic administration of a drug is generally intended for the drug or its metabolites to have a continued beneficial effect on a condition or to prevent or slow deterioration of a disease-state over time. Chronic administration is often delivered to a subject by the subject themselves (i.e. self-administration), for example, by oral or subcutaneous administration.

Subcutaneous Administration

The present invention also relates to subcutaneous administration of levosimendan in a subcutaneous formulation to achieve the effects disclosed herein. Due to the potentially irritating, vesicant, and extravasation effects of administering inotropes and vasoactive substances, such as levosimendan, subcutaneous administration of the existing levosimendan formulation has not previously been investigated. Nevertheless, subcutaneous administration may be used where a less invasive route of delivery would be a novel method of administration.

Notwithstanding the potential extravasation concerns with subcutaneous administration, the subcutaneous route of levosimendan administration may be better tolerated than intravenous delivery. Subcutaneous administration may reduce and delay absorption of levosimendan, resulting in lower peak plasma concentrations of levosimendan as compared to intravenous administration. This may avoid the occurrence of typical side effects of levosimendan administration, particularly hypotension caused by the maximum concentration of levosimendan (Cmax) because higher plasma concentrations and a higher Cmax of levosimendan typically leads to more frequent side effects, such as hypotension.

Subcutaneous administration of levosimendan offers a clear advantage in terms of eliminating the potential for central line infections that are common with IV chronic administration via PICC and port-a-cath devices that are often necessary for convenient repeated IV access.

Despite exhibiting a delay in levosimendan absorption along with lower plasma concentrations, subcutaneous administration of levosimendan unexpectedly results in a similar plasma concentration profile of the levosimendan metabolite OR-1896. This results in a better safety profile, due to the comparable levels of OR-1896 in the blood without the high peak plasma concentration of levosimendan.

There are numerous practical advantages with subcutaneous administration such as: being easily titrated, facilitating patient control, reliable records of dosing, reducing nursing burden, and reducing the risk of drug diversion.

One delivery device suitable for subcutaneous administration is an ambulatory infusion pump, such as a CADD pump, which stands for continuous ambulatory delivery device pump. Additionally, subcutaneous administration could be delivered through a simple prefilled syringe, syringe pump, injection pen, autoinjector, micropump, or patch device. (Bittner et al. 2018)

Although in the present instance the subcutaneous formulation would be substantially similar to the intravenous formulation, certain additives could be introduced to make the treatment more tolerable for the patient. Buffers, such as water, sodium bicarbonate, or other similar buffering agents that are known to increase pH, could be added to increase the pH of the subcutaneous formulation.

Like the administration of the intravenous formulation, the subcutaneous administration of levosimendan can be administered intermittently as well as chronically. The intermittent administration can take place weekly for a 24-hour period. In addition to being administered by a trained professional, subcutaneous administration makes it much simpler for the patient to self-administer the levosimendan formulation.

Subcutaneous administration of levosimendan can support an expanded range of dilutions and corresponding concentration while still being viable.

| Example Simdax Vial (mg) | Vial Vol/ml | Vol Diluent ml | Total Vol ml | Diluted Concentration mg/ml | 24 Hr continuous Infusion Rate ml/hr | Small Volume (0.1-2.0 ml) via Daily injection, Pump, or Patch Delivery |
|---|---|---|---|---|---|---|
| 12.5 | 5 | 0 | 5 | 2.5000 | 0.21 | 0.1-2.0 |
| 12.5 | 5 | 5 | 10 | 1.2500 | 0.42 | 0.5-2.0 |
| 12.5 | 5 | 25 | 30 | 0.4167 | 1.25 | NA |
| 12.5 | 5 | 75 | 80 | 0.1563 | 3.33 | NA |
| 12.5 | 5 | 150 | 155 | 0.0806 | 6.46 | NA |
| 12.5 | 5 | 250 | 255 | 0.0490 | 10.63 | NA |
| 12.5 | 5 | 500 | 505 | 0.0248 | 21.04 | NA |
| 12.5 | 5 | 1000 | 1005 | 0.0124 | 41.88 | NA |
| 12.5 | 5 | 1500 | 1505 | 0.0083 | 62.71 | NA |

Overall, data supports that subcutaneous administration is simpler than intravenous infusions, can reduce drug delivery-related healthcare costs and resources, and is largely preferred by both patients and health care providers (Bittner et al. 2018).

Several methods of subcutaneous administrations are known in the art, and any such method may be used for subcutaneous administration of levosimendan. Examples of subcutaneous administration methods include, but are not limited to, manual needle injection and various subcutaneous drug delivery devices such as subcutaneous administration systems that deliver a drug via a pump apparatus such as performed with certain insulin pump systems. e.g. the Omnipod© system.

In an embodiment the subcutaneous formulation comprises water in an amount effective to reduce pain caused by the administration.

In an embodiment the subcutaneous formulation comprises buffers to raise the pH higher than 3.0.

In an embodiment the subcutaneous administration reduces side effects relative to intravenous administration.

In an embodiment the subcutaneous administration reduces peak plasma concentrations of levosimendan relative to intravenous administration by at least 1% to 25%.

Levosimendan formulations that have been described for subcutaneous administration are described in, for example, PCT International Publication No. WO 2020/041180 A1 (Application No. PCT/US2019/047032), the entire contents of which are incorporated by reference.

In some embodiments, a pharmaceutical composition of levosimendan for treatment in subjects in need thereof, for example, for treatment of heart failure with preserved ejection fraction, specifically in human subjects who also have pulmonary hypertension (PH-HFpEF patients), by subcutaneous administration is in a formulation comprising: (a) an effective amount of levosimendan, its metabolites OR-1896 or OR-1855, or a combination thereof; (b) a cyclodextrin or a cyclodextrin derivative; and (c) one or more additional pharmaceutically acceptable additives.

In an embodiment, the cyclodextrin derivative comprises an alpha-cyclodextrin derivative, a beta-cyclodextrin derivative, or a gamma-cyclodextrin derivative.

In an embodiment, the cyclodextrin derivative comprises sodium sulfonate salt.

In an embodiment, the cyclodextrin derivative comprises a butyl ether spacer group, an alkyl ether space group, or a combination thereof.

In an embodiment, the cyclodextrin derivative comprises sulfobutylether.

In an embodiment, the cyclodextrin derivative comprises sulfobutylether beta-cyclodextrin.

In an embodiment, the cyclodextrin or cyclodextrin derivative is in an amount of about 50 mg/ml to about 400 mg/ml, preferably in an amount of about 100 mg/ml to about 300 mg/ml.

In an embodiment, the formulation comprises a pH of about 5 to about 9, preferably a pH of about 6 to about 8.

In an embodiment, the one or more pharmaceutically acceptable additives comprise one or more non-citrate buffering agents.

In an embodiment, the one or more pharmaceutically acceptable additives comprise a phosphate buffer.

In an embodiment, the one or more pharmaceutically acceptable additives comprise one or more pH-modifying agents.

In an embodiment, wherein the one or more pharmaceutically acceptable additives comprise one or more preservatives, one or more antioxidants, one or more carriers, or a combination thereof.

In an embodiment, the one or more carriers comprise a liquid media selected from a group consisting of solutions, suspensions, hydrogels, liposomes, emulsions, and a combination thereof.

In an embodiment, the one or more carriers alter the absorption characteristics in a way that extend the effectiveness and or minimize side effects.

In an embodiment, the levosimendan is in an amount of about 0.1 mg/ml to about 100 mg/ml, preferably in an amount of about 0.1 mg/ml to about 30 mg/ml.

In an embodiment, the formulation is substantially free of alcohol.

In an embodiment, the formulation is alcohol-free.

In an embodiment, the formulation is preservative-free.

In an embodiment, the formulation is in the form of particles.

In an embodiment, the formulation is lyophilized.

In an embodiment, the formulation is spray-dried.

In an embodiment, a pharmaceutical composition for subcutaneous administration of levosimendan is in a formulation comprising: (a) levosimendan in an amount of about 0.1 mg/ml to about 10 mg/ml; (b) a cyclodextrin or a cyclodextrin derivative in an amount of about 50 mg/ml to about 500 mg/ml; and (c) phosphate buffer of about 1 mM to about 20 mM.

In an embodiment, the formulation has a pH of about 6 to about 8.

In an embodiment, the formulation is substantially free of alcohol.

In an embodiment, the formulation is lyophilized.

Furthermore, levosimendan formulations that have been described for intravenous administration may be adopted for subcutaneous administration. For example, see U.S. Pat. No. 10,507,179, the entire contents of which are incorporated by reference.

In some embodiments, levosimendan formulations suitable for subcutaneous administration include, but are not limited to, a pharmaceutical composition, comprising levosimendan as active ingredient, and a solubilizer selected from the group consisting of cyclodextrins, consisting of sulfo-butyl-ether beta-cyclodextrin, alpha-cyclodextrin and methyl-beta-cyclodextrin and mixtures thereof, fatty acid esters of glycerol, polyethylene derivatives of alpha-tocopherol, bile acids, with the proviso that the use of co-solvents such as ethanol, propyleneglycol, polyethyleneglycol, poloxamers or polyvinylpyrrolidon is excluded.

In an embodiment, the solubilizer is D-alpha tocopheryl polyethylene glycol 1000 succinate or a bile salt, which is preferably selected from the group consisting of sodium glycocholate, taurocholic acid sodium salt, taurodeoxycholic acid sodium salt and sodium cholate, or mixtures thereof.

In an embodiment, the micelles are polymeric micelles, preferably polyethylene oxide)-poly(propylene oxide) block copolymer micelles, or mixed micelles composed of soy phosphatidylcholine/sodium glycocholate or hybrid micelles.

In an embodiment, the pharmaceutical composition comprises levosimendan as active ingredient, and sulfo-butyl-ether beta-cyclodextrin as a solubilizer, with the proviso that the use of co-solvents comprised of ethanol, propyleneglycol, polyethyleneglycol, poloxamers or polyvinylpyrrolidon is excluded.

In an embodiment, sulfo-butyl-ether beta-cyclodextrin is preferably present in a mmolar ratio compared to levosimendan within a range of 1-15 mmol cyclodextrine(s): 1 mmol levosimendan. Preferably the excess of cyclodextrine(s) is 4-12 mmol cyclodextrine(s): 1 mmol levosimendan, still more preferably 6-10 mmol cyclodextrine(s): 1 mmol levosimendan.

In an embodiment, levosimendan is present in solubilized form.

In an embodiment, levosimendan is solubilized by micellarization or by complexation.

In an embodiment, the pharmaceutical composition is in the form of a solution, more preferably in the form of an aqueous solution.

In an embodiment, the amount of the solubilizer is 2 to 45 percent by weight of the pharmaceutical composition.

In an embodiment, the pH of the solution is in the range of 7.0 to 8.0, more preferably in the range of 7.2 to 7.8.

In an embodiment, the levosimendan in an amount of 1 to 15 mg/ml solution.

In an embodiment, a dried powder is obtained from the pharmaceutical composition for use as a medicament in treating heart failure with preserved ejection fraction, specifically in human subjects who also have pulmonary hypertension (PH-HFpEF patients). The dried powder is obtainable by drying a solution comprising the solubilized levosimendan, and is reconstituted to a solution suitable for subcutaneous administration.

In an embodiment, the dried powder for use is a subcutaneous infusion concentrate comprising the levosimendan in an amount of 1 to 15 mg/ml solution.

In an embodiment, the concentrate is to be adjusted to a pH in the range of 7.2 to 8.0.

In an embodiment, the solvent for reconstitution of the dried powder for use is water, or an isotonic buffer system.

In an embodiment, the water has a pH in the range of 7.2 to 7.8, or the isotonic buffer system has a pH in the range of 7.2 to 7.4

In an embodiment, the dried powder is obtainable by drying a solution comprising the solubilized levosimendan and a suitable pharmaceutical vehicle used for freeze-drying.

The present disclosure provides a subcutaneous formulation of levosimendan for use in treating PH-HFpEF in a human subject afflicted with PH-HFpEF, wherein the subcutaneous formulation is obtained from a dried powder, wherein the dried powder is obtained from a pharmaceutical composition comprising: (a) levosimendan; (b) sulfo-butyl-ether beta-cyclodextrin; (c) sodium hydroxide or acetic acid; and water for injection.

In an embodiment, the amount of levosimendan is 2.5 mg/ml water for injection.

In an embodiment, the amount of sulfo-butyl-ether beta-cyclodextrin is 0.175 mg/ml water for injection.

In an embodiment, the sodium hydroxide or acetic acid is in a suitable amount to adjust the pH to a range of 7.2 to 7.8.

In an embodiment, the pharmaceutical composition is filter sterilized.

In an embodiment, the pharmaceutical composition is lyophilized.

In an embodiment, the subcutaneous formulation of levosimendan is obtained from the dried powder by reconstituting the dried powder in an amount of aqueous solution suitable for subcutaneous administration.

In an embodiment, the reconstituted subcutaneous formulation is pH adjusted to 7.2 to 7.8 with sodium hydroxide or acetic acid.

Oral Administration

The present invention also relates to oral administration of levosimendan in an oral formulation to achieve the effects disclosed herein. There are numerous practical advantages with oral administration such as: being easily administered and titrated, facilitating patient control, and reducing nursing burden.

According to some embodiments, oral administration is in the form of hard or soft gelatin capsules, pills, capsules, tablets, including coated tablets, dragees, elixirs, suspensions, liquids, gels, slurries or syrups and controlled release forms thereof. Thus, the invention provides a method of administering levosimendan in the form of a tablet, a capsule, or in a liquid.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin for use in a dispenser may be formulated containing a powder mix of the compound and a suitable powder base, such as lactose or starch.

Solid dosage forms for oral administration include without limitation capsules, tablets, pills, powders, and granules. In such solid dosage forms, the active compound is admixed with at least one inert pharmaceutically acceptable carrier such as sucrose, lactose, or starch. Such dosage forms can also comprise, as it normal practice, additional substances other than inert diluents, e.g., lubricating, agents. In the case of capsules, tablets and pills, the dosage forms may also comprise buffering agents. Tablets and pills can additionally be prepared with enteric coatings. The term "enteric coating", as used herein, refers to a coating which controls the location of composition absorption within the digestive system. Non-limiting examples for materials used for enteric coating are fatty acids, waxes, plant fibers or plastics. Liquid dosage forms for oral administration may further contain adjuvants, such as wetting agents, emulsifying and suspending agents, and sweetening, flavoring and perfuming agents.

In an embodiment, the administration is delivered via oral dosing, and the oral dosing can be an immediate release or extended release formulation.

In some embodiments, a pharmaceutical composition of levosimendan for treatment in subjects in need thereof, for example, for treatment of heart failure with preserved ejection fraction, specifically in human subjects who also have pulmonary hypertension (PH-HFpEF patients), by oral administration is in a formulation comprising an effective amount of levosimendan, its metabolites OR-1896 or OR-1855, or a combination thereof and one or more additional pharmaceutically acceptable additives.

In an embodiment, the oral formulation comprises levosimendan, its metabolites OR-18% or OR-1855, or a combination thereof in the amount of 0.1 mg, 0.25 mg, 0.5 mg, 0.75 mg, 1 mg, 2 mg, 3 mg, or 4 mg.

In an embodiment, the oral formulation comprises microcrystalline cellulose.

In an embodiment, the oral formulation comprises alginic acid.

In an embodiment, the oral formulation comprises steric acid.

In an embodiment, the oral formulation is in a capsule form.

In an embodiment, the oral formulation is the capsule form is a HPMC capsule.

In an embodiment the oral formulation comprise in a capsule form and the oral formulation comprises 1 mg levosimendan, 96.4 mg microcrystalline cellulose, 30.0 mg alginic acid, and 5.3 mg stearic acid.

In an embodiment, the oral dosage form comprises levosimendan in the amount of 0.1 mg, 0.25 mg, 0.5 mg, 0.75 mg, 1 mg, 2 mg, 3 mg, or 4 mg, more preferably in the amount of 1-3 mg.

In an embodiment, a subject is orally administered a capsule comprising levosimendan in the amount of 1 mg once per day. The oral dosing may be titrated according to, for example, the effectiveness of the treatment, tolerability, changes in heart rate, and body weight of the subject. The titration of levosimendan may be in 1 mg increments and range from 1-10 mg per day, more preferably between 1-4 mg per day.

The titration of levosimendan administration may occur over the course of days, weeks, or months. The effect of duration at a particular dosage amount on tolerability should also be considered when titrating, e.g. the tolerability of a subject to the levosimendan oral treatment may increase with an increase in duration at a particular dosage amount.

For example, a subject may begin an oral levosimendan treatment course at 1 mg/day (i.e. ingesting one capsule comprising 1 mg levosimendan per day). The subject may maintain a levosimendan dosage of 1 mg/day for two weeks. After two weeks, if the levosimendan dosage is well-tolerated and heart rate is increased <15 BPM, the subject can titrate up to a dosage of 2 mg/day (i.e. ingesting two capsules, each comprising 1 mg levosimendan, per day). The subject may continue to titrate up in increments of 1 mg levosimendan in this manner until an optimal oral dosage is achieved, for example, up to 10 mg of levosimendan per day.

A subject receiving levosimendan by other administration routes, for example, intravenous injection, may be transitioned to an oral dosing scheme. For example, a subject receiving levosimendan by intravenous injection may begin an oral dosing after receiving a final 24-hour infusion of levosimendan. The oral dosing of levosimendan may begin within days or weeks, for example, one week, of the final 24-hour infusion. The oral dosage may begin at 1 mg/day, followed by titration as indicated above.

Combination Therapy

The administration of two drugs to treat a given condition, such as PH-HFpEF, raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry, 2006). In one example, combined administration of GA and interferon (IFN) has been experimentally shown to abrogate the clinical effectiveness of either therapy. (Brod 2000) In another experiment, it was reported that the addition of prednisone in combination therapy with IFN-β antagonized its up-regulator effect. Thus, when two drugs are administered to treat the same condition, it is unpredictable whether each will complement, have no effect on, or interfere with, the therapeutic activity of the other in a human subject.

Not only may the interaction between two drugs affect the intended therapeutic activity of each drug, but the interaction may increase the levels of toxic metabolites (Guidance for Industry, 2006). The interaction may also heighten or lessen the side effects of each drug. Hence, upon administration of two drugs to treat a disease, it is unpredictable what change will occur in the negative side profile of each drug. In one example, the combination of natalizumab and interferon s-la was observed to increase the risk of unanticipated side effects. (Vollmer, 2008; Rudick 2006; Kleinschmidt-DeMasters, 2005; Langer-Gould 2005)

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs. (Guidance for Industry, 2006)

As used herein, "combination" means an assemblage of reagents for use in therapy either by simultaneous, contemporaneous, or fixed-dose combination delivery. Simultaneous delivery refers to delivery of an admixture (whether a true mixture, a suspension, an emulsion or other physical combination) of the drugs. In this case, the combination may be the admixture or separate containers of the levosimendan and a second agent that are combined just prior to delivery. Contemporaneous delivery refers to the separate delivery of the levosimendan and second agent at the same time, or at times sufficiently close together that an additive or preferably synergistic activity relative to the activity of either the levosimendan or the cardiovascular drug alone is observed. Fixed-dose combination delivery refers to the delivery of two or more drugs contained in a single dosage form for oral administration, such as a capsule or tablet.

As used herein, "second agent" for use in combination therapy includes any one of the following: Phosphodiesterase-5 (PDE5) inhibitor, an endothelin receptor antagonist (ERA) (e.g., Bosentan, Ambrisentan), a Prostanoid (e.g., Trepostinil, Selexipag, Ralinepag), a Soluble Guanylate Cyclase stimulator (e.g., Riociguat), a nitrate or nitrite, a calcium channel blocker (CCB), fatty acid oxidation inhibitors (e.g., Ranolazine, Trimetazidine), a beta-blocker (BB), an Angiotensin-converting enzyme (ACE) inhibitor, a neprilysin inhibitor (e.g., Sacubitril. Sampatrilat, Gemopatrilat, Fasidotril, Omapatrilat, Candoxatril), a neprilysin and angiotensin receptor blocker (ANRI) (e.g., Entresto), an Angiotensin II receptor blocker (ARB), a diuretic, an Aldosterone antagonist, Digoxin, Ivabradine, Hydralazine, Seralaxin, a natriuretic peptide, an atrial natriuretic peptide (ANP), or Nesiritide.

The recommended dose and schedule for Entresto is 24/26 mg twice daily (24 mg of sacubitril and 26 mg of valsartan). The dose is doubled every two to four weeks, as tolerated by the patient. The composition recited hereinabove is described in U.S. Pat. Nos. 7,468,390; 8,101,659; 8,404,744; 8,796,331; 8,877,938; and 9,388,134, the entire contents of which are incorporated by reference.

The recommended dose and schedule for Sacubitril is 24 mg twice daily. The dose is doubled every two to four weeks, as tolerated by the patient.

The recommended dose and schedule for Ranolazine is 500 mg twice daily. The dose is increased to 1000 mg twice daily, as needed, based on clinical symptoms. The composition recited hereinabove is described in U.S. Pat. Nos. 6,303,607; 6,369,062; 6,479,496; 6,503,911; 6,525,057; 6,562,826; 6,617,328; 6,620,814; 6,852,724; and 6,864,258, the entire contents of which are incorporated by reference.

The recommended dose and schedule for Bosentan is 62.5 mg twice daily for patients >12 years of age. After 4 weeks, the dose is increased to 125 mg twice daily if the patient weighs greater than 40 kg, and the dose is not changed if the patient weights less than 40 kg. The composition recited hereinabove is described in U.S. Pat. Nos. 7,959,945 and 8,309,126, the entire contents of which are incorporated by reference.

The recommended dose and schedule for Ambrisentan is 5 mg orally once a day. The dose is increased to 10 mg orally once a day, if 5 mg is tolerated by the patient. The composition recited hereinabove is described in U.S. Pat. Nos. 8,377,933; 9,474,752; and 9,549,926, the entire contents of which are incorporated by reference.

The recommended dose and schedule for Trepostinil is 0.25 mg orally every 12 hours or 0.125 mg every 8 hours for oral extended-release tablets; 3 breaths (18 mcg) per treatment session 4 times per day or if not tolerated then reduce to 1 or 2 breaths and subsequently increase to 3 breaths as tolerated for inhalation: or 1.25 ng/kg/min via continuous subcutaneous or IV infusion or 0.625 ng/kg/min if the larger dose cannot be tolerated for patients new to prostacyclin infusion therapy. The composition recited hereinabove is described in U.S. Pat. Nos. 10,076,505; 7,999,007; 8,653, 137; 8,658,694; 9,199,908; 9,593,066; 9,604,901; and 9,713,599, the entire contents of which are incorporated by reference.

The recommended dose and schedule for Selexipag is 200 mcg orally twice a day. The dose is incrementally increased by 200 mcg orally twice a day at weekly intervals to the highest tolerated dose, not to exceed 1600 mcg orally twice a day. The composition recited hereinabove is described in U.S. Pat. Nos. 7,205,302; 8,791,122; 9,173,881; and 9,284, 280, the entire contents of which are incorporated by reference.

The recommended dose and schedule for Ralinepag is 10 µg twice daily to 300 µg twice daily. The composition recited hereinabove is described in Efficacy and safety of ralinepag, a novel oral IP agonist, in PAH patients on mono or dual background therapy: results from a phase 2 randomised, parallel group, placebo-controlled trial (Torres et al. 2019), the entire contents of which are incorporated by reference.

The recommended dose and schedule for Riociguat is 1 mg orally 3 times a day. This dose is increased as tolerated, but is not to exceed 2.5 mg orally 3 times a day. The composition recited hereinabove is described in U.S. Pat. Nos. 6,743,798 and 7,173,037, the entire contents of which are incorporated by reference.

The recommended dose and schedule for Trimetazidine is 60 mg/day to 140 mg/day. The composition recited hereinabove is described in Defining the Role of Trimetazidine in the Treatment of Cardiovascular Disorders: Some Insights on Its Role in Heart Failure and Peripheral Artery Disease (Chrusciel et al. 2014), the entire contents of which are incorporated by reference.

The recommended dose and schedule for Sampatrilat is 50 mg to 100 mg daily. The composition recited hereinabove is described in Sustained Antihypertensive Actions of a Dual Angiotensin-Converting Enzyme Neutral Endopeptidase Inhibitor, Sampatrilat, in Black Hypertensive Subjects (Norton et al. 1999), the entire contents of which are incorporated by reference.

Gemopatrilat is described in Metabolism Of [14c] Gemopatrilat After Oral Administration To Rats, Dogs, And Humans (Wait et al. 2006), the entire contents of which are incorporated by reference.

The recommended dose and schedule for Fasidotril is 100 mg twice daily. The composition recited hereinabove is described in Antihypertensive effects of fasidotril, a dual inhibitor of neprilysin and angiotensin-converting enzyme, in rats and humans (Laurent et al. 2000), the entire contents of which are incorporated by reference.

The recommended dose and schedule for Omapatrilat is 10 mg to 80 mg daily. The composition recited hereinabove is described in Omapatrilat and enalapril in patients with hypertension: the Omapatrilat Cardiovascular Treatment vs. Enalapril (OCTAVE) trial (Kostis et al. 2004), the entire contents of which are incorporated by reference.

The recommended dose and schedule for Candoxatril is 200 mg twice a day to 400 mg twice a day. The composition recited hereinabove is described in Comparison of the short-term effects of candoxatril, an orally active neutral endopeptidase inhibitor, and frusemide in the treatment of patients with chronic heart failure (Northridge et al. 1999), the entire contents of which are incorporated by reference.

The recommended dose and schedule for Digoxin is 8 to 12 mcg/kg through intravenous administration for the total loading dose and increased to 0.1 to 0.4 mg/day for the maintenance regiment. For oral administration, the dose and schedule is 10 to 15 mcg/kg for the total loading dose and increased to 3.4 to 5.1 mcg/kg/day. Another dosing option is 0.125 to 0.25 mg per day for oral or intravenous administration, with higher doses of 0.375 to 0.5 mg/day rarely needed. The composition recited hereinabove is described in Digoxin: A systematic review in atrial fibrillation, congestive heart failure and post myocardial infarction (Virgadamo et al. 2015), the entire contents of which are incorporated by reference.

The recommended dose and schedule for Ivabradine is 5 mg orally twice a day with meals. This dose is increased as tolerated, but is not to exceed 7.5 mg orally twice a day. The composition recited hereinabove is described in U.S. Pat. Nos. 7,361,649; 7,361,650; 7,867,996; and 7,879,842, the entire contents of which are incorporated by reference.

The recommended dose and schedule for Hydralazine is 10 mg orally 4 times a day for the first 2 to 4 days, increased to 25 mg orally 4 times a day for the balance of the first week. This dose is increased to 50 mg orally 4 times a day for week 2 and subsequent weeks. The composition recited hereinabove is described in U.S. Pat. Nos. 6,465,463 and 6,784,177, the entire contents of which are incorporated by reference.

The recommended dose and schedule for Seralaxin is three 48-hour intravenous infusions of 30 μg/kg/day. The composition recited hereinabove is described in RELAX-REPEAT: A Multicenter, Prospective, Randomized, Double-Blind Study Evaluating the Safety and Tolerability of Repeat Doses of Serelaxin in Patients with Chronic Heart Failure (Teerlink et al. 2016), the entire contents of which are incorporated by reference.

The recommended dose and schedule for Nesiritide is 2 mcg/kg IV bolus, followed by 0.01 mcg/kg/min via continuous IV infusion; not to be titrated more frequently than every 3 hours to a maximum of 0.03 meg/kg/min. The composition recited hereinabove is described in U.S. Pat. No. 5,114,923, the entire contents of which are incorporated by reference.

A subset of second agents that have a beneficial effect in a combination therapy with levosimendan include: K-ATP channel activators (e.g. pinacidil, diazoxide, bimakalim, levocromakalim, cromakalim, rimakalim, and nicorandil, etc.); nitrates (e.g. nitroglycerin-NTG, isosorbide dinitrate, etc.); nitrites (e.g. sodium nitrite, amyl nitrite, etc.); NO donors—(Sodium nitroprusside, Nitric Oxide, Molsidomine, linsidomine); PDE inhibitors (e.g. Milrinone, Pimobendan, Enoximone, etc.); natriuretic peptides, such as BNP (e.g. nesiritide), ANP (e.g. carparetide and ularitide), CDNP (e.g. cenderitide), and others (e.g. CNP, DNP, MANP, etc.); NEP inhibitors (e.g. sacubitril, sampatrilat/sympatril, fasidotril, omapatrilat/omapatril, candoxatril, etc.); and ARNIs (Entresto). Furthermore, a combination therapy with levosimendan may include any of the above second agents, a diuretic, or both.

Additionally, it is noted that combined pre and post capillary pulmonary hypertension and heart failure with preserved ejection fraction (Cpc-PH-HFpEF) is a small and special phenotype of certain PH-HFpEF patients. These patients may benefit from agents that reduce pulmonary vascular resistance (Opitz 2016). The HELP Study identified that Levosimendan did not decrease pulmonary vascular resistance, particularly upon chronic administration. Therefore, Cpc-PH-HFpEF patients may benefit from a combination therapy comprising Levosimendan and an agent that reduces pulmonary vascular resistance. Accordingly, a combination therapy of Levosimendan with a pulmonary vasodilator, including but not limited to, phosphodiesterase-5 inhibitors (PDE-5 inhibitors, e.g. sildenafil, tadalafil, etc.); endothelin receptor antagonists (ERAs, e.g. bosentan, ambrisentan, etc.); and prostacyclins (e.g. epoprostenol, iloprost, Treprostinil, etc.) may provide therapeutic benefits to Cpc-PH-HFpEF patients.

Each drug can be administered in the dose and regiment that has been disclosed in the drug's aforementioned literature.

The embodiments referred to above refer to several drugs being substantially effective in the body at a same time. Several drugs can be administered substantially at the same time, or can be administered at different times but have effect on the body at the same time. For example, this includes administering levosimendan before or subsequently, while functioning of levosimendan in the body is substantially extant.

Therefore, the state of the art at the time of filing is that the effects of combination therapy of two drugs, in particular levosimendan and a second agent, cannot be predicted until the results of combination studies are available.

Each embodiment disclosed herein is contemplated as being applicable to each of the other disclosed embodiments. Thus, all combinations of the various elements described herein are within the scope of the invention.

The following examples are presented in order to more fully illustrate some embodiments of the invention. They should, in no way be construed, however, as limiting the broad scope of the invention.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only. (HELP Study—Hemodynamic Evaluation of Levosimendan in PH-HFpEF)

Example 1

Brief Summary

A multicenter, Phase 11, double-blind, randomized, placebo-controlled study is conducted of levosimendan in pulmonary hypertension patients with heart failure and preserved left ventricular ejection fraction (PH-HFpEF) designed to evaluate the efficacy and safety of intermittent levosimendan compared with placebo in hemodynamic improvement with exercise in PH-HFpEF subjects.

Intervention

Drug: Levosimendan

Subjects are administered Levosimendan as follows: A sterile Levosimendan 2.5 mg/mL concentrated solution that is diluted in 250-500 mL of 5% Dextrose or 0.9 Normal Saline to achieve a 50 microgram/mL solution for infusion.

Subjects are administered Matching Placebo as follows: A sterile Placebo 2.5 mg/mL concentrate solution that is diluted in 250-500 mL of 5% Dextrose or 0.9 Normal Saline to achieve a 50 microgram/mL solution for infusion.

Study Arms

Experimental: Levosimendan 2.5 mg/mL Injectable Solution
  a. 0.075-0.1 μg/kg/min for 24 hours (weekly)
  b. Intervention: Drug: Levosimendan
Experimental: Matching Placebo
  a. 0.075-0.1 μg/kg/min for 24 hours (weekly)
  b. Intervention: Drug: Levosimendan Estimated Enrollment 36 subjects Inclusion Criteria Men or women, at least 18 years of age.

Confirmed diagnosis of WHO Group 2 Pulmonary Hypertension (PH) with heart failure and preserved ejection fraction (HFpEF).

WHO Group 2 Pulmonary Hypertension subjects with heart failure and preserved ejection fraction as defined by:
  a. Mean pulmonary arterial pressure (mPAP)≥35 mmHg at rest or with legs up (at baseline right heart catheter/Lead-In)
  b. Pulmonary capillary wedge pressure (PCWP)≥20 mmHg at rest or with legs up (at baseline right heart catheter/Lead-In)
  c. NYHA Class II or III
  d. LVEF ≥40% by echocardiogram within three months of enrollment with no change in clinical status suggesting the potential for deterioration in systolic function.

Signed (by the subjects or their legally acceptable representatives) informed consent document indicating that they understand the purpose of and procedures required for the study and are willing to participate in the study.

Ability to walk at least 50 meters, but not more than 550 meters in a six-minute walk test.

Long term oxygen treatment (if applicable) must be stable for 30 days prior to enrollment.

Subjects on a chronic medication or therapy for any underlying cardiac condition must be on a stable dose for ≥30 days prior to randomization, with the exception of diuretics and antihypertensive medication for blood pressure control which may be discontinued if deemed appropriate.

Subjects on chronic medications for any underlying respiratory condition must be on a stable dose for ≥30 days prior to randomization.

Randomization Criteria

Response to Lead-In Levosimendan: Patients who demonstrate a ≥4 mmHg reduction in PCWP from baseline measured during bicycle exercise (25 watts) with no more than a 10% decrease from baseline cardiac index following the 24-hour infusion of levosimendan.

Exclusion Criteria

Previous PCI or cardiac surgery (CABG) unless documented to have a negative stress test within the last 12 months.

Clinically symptomatic mitral or aortic valvular heart disease.

Cardiac index greater than 4.0 L/min/m$^2$.

In the opinion of the Principal Investigator, the subject has a primary diagnosis of PH other than WHO Group 2 PH-HFpEF Congenital heart disease other than surgically corrected pre and post tricuspid shunts for at least 10 years.

Symptomatic coronary artery disease based on a positive stress test.

Patients planning lung or heart transplant; or cardiac surgery in the next 4 months.

Patients diagnosed with pulmonary hypertension associated with clinically significant lung disease at the time of initial diagnosis, or patients with a congenital defect of the lung.
  a. Clinically significant obstructive lung disease is defined as FEV1/FVC<60% of predicted, unless a high-resolution chest CT scan shows no more than mild areas of emphysematous changes.
  b. Clinically significant restrictive lung disease is defined as a FVC of <60% of predicted, unless a high resolution chest CT scan shows no more than mild areas of interstitial lung disease or pulmonary fibrosis.

Dialysis at randomization (either hemodialysis, peritoneal dialysis, continuous venovenous hemofiltration, or ultrafiltration).

Estimated glomerular filtration rate (eGFR)<30 mL/min/1.73 m$^2$.

Liver dysfunction with Child Pugh Class B or C.

Evidence of systemic bacterial, systemic fungal, or viral infection in last 2 weeks.

Weight >150 kg.

Symptomatic low systolic blood pressure (SBP) that cannot be managed to ensure SBP≥100 mmHg at initiation of study drug.

Heart rate ≥100 bpm with study drug, symptomatic and persistent for at least 10 minutes at Lead-In.

Hemoglobin <80 g/L.

Serum potassium <3.0 mmol/L or >5.5 mmol/L at baseline.

Pregnant, suspected to be pregnant, or breast-feeding.

Known allergic reaction or sensitivity to levosimendan or excipients.

A history of Torsades de Pointes.

Received levosimendan within 30 days before the planned start of study drug.

Received an experimental drug or used an experimental medical device within 30 days before the planned start of the study drug.

Concomitant administration of pulmonary vasodilator therapy, or taken within 14 days of randomization.

Employees of the investigator or study center, with direct involvement in the proposed study or other studies under the direction of that investigator or study center, as well as family members of the employees or the investigator.

Inability to comply with planned study procedures.

Description of Study (HELP Study)

This is a multicenter, Phase 11, double-blind, randomized, placebo-controlled study of levosimendan in pulmonary hypertension patients with heart failure and preserved left ventricular ejection fraction (PH-HFpEF) designed to evaluate the efficacy and safety of intermittent levosimendan compared with placebo in hemodynamic improvement with exercise in PH-HFpEF subjects.

Enrolled PH-HFpEF subjects receive a lead-in 24-hour levosimendan infusion to determine their hemodynamic response and eligibility for the double-blind phase of the study. A total of 36 "responders" are randomized in the double-blind, placebo-controlled phase. "Responders" are identified as those subjects with a ≥4 mmHg reduction in PCWP during bicycle exercise (25 watts) and no more than a 10% decrease in cardiac index between the baseline measurements and repeated measurements following the initial infusion.

Study drug is administered via i.v. infusion over 24 hours weekly through Week 5 via a PICC line. Infusions (Week 2-5) are done in the subject's home by a study nurse. Patients return to the study site for a visit between the Week 3 and Week 4 infusions for assessment of subject safety/response and need for dose adjustment. Each subject is to return on Week 6 for assessment of efficacy and safety on study drug. A right heart catheter will be inserted to obtain hemodynamic measurements at rest and exercise at baseline, the following day after the lead-in 24-hour infusion, and during Week 6.

During the Lead-in phase of the study, a sufficient number of subjects are enrolled and receive levosimendan to identify a total of 36 'responders.' The levosimendan 'responders' are randomized 1:1, levosimendan or placebo, for the double-blind phase of the study.

During the Lead-in phase, levosimendan, supplied as a concentrated solution (2.5 mg/mL), is mixed with diluent and administered intravenously at 0.10 μg/kg/min for 24 hours+/−30 min.

During the Double-blind phase, study drug concentrated solution (2.5 mg/mL), levosimendan or placebo, is mixed with diluent and administered via a PICC line as weekly infusions at 0.075 μg/kg/min for 24 hours. Patients undergo a dose escalation at Week 4 and 5 (0.10 μg/kg/min for 24 hours) unless there has been a meaningful change in blood pressure or heart rate. Infusion rates may be reduced to 0.05 μg/kg/min if the higher dose is not well-tolerated at any time during the initial 5 weeks.

The study is divided into a Screening phase, a Lead-In phase, and a Double-Blind treatment phase. The Screening, Lead-In, Interim Office (between Weeks 3 and 4) and Week 6 visits occurs at the investigator's office. Infusions at Weeks 2, 3, 4 and 5 occur at the subject's home under the care of a home healthcare nurse. Subjects are instructed to contact the investigator at any time during the 24 hour at home infusions to report adverse events, or at any time they would like to speak with the investigator regarding the study or to report adverse events during the entirety of the trial.

Visits during the Lead-In phase of the trial require a subject to be hospitalized for the entire infusion period, which at a minimum will last 24 hours. Once the infusion is complete, hemodynamic measurements are collected to ensure subject eligibility. Visits for Week 2 through Week 6 are calculated based on the date of the Lead-in infusion.

At least 72 hours prior to the first infusion (Lead-In Visit), all patients wear a small, lightweight cardiac monitoring sensor on their chest to measure heart rate and to detect any arrhythmias. This patch is water-resistant and can be worn in the shower by the patient. The patch is removed prior to the first infusion of study drug. Additionally, the following procedures are performed: Obtain signed main study ICF (must be obtained prior to performance of any study-specific tests or evaluations that are not considered standard of care), confirm inclusion/exclusion criteria, history of qualifying hemodynamics, conduct a medical history, body weight, record prior/concomitant medications including all prescription and non-prescription drugs, vitamins, and dietary or herbal supplements, record demographic information, perform complete physical examination, including height and body weight, urine pregnancy test (women of child-bearing potential only), hematology and clinical chemistry blood samples, measure vital signs (BP, PR, respiratory rate, temperature), Child-Pugh Class, NYHA Functional Class, Conduct 12-lead ECG, Echocardiogram (within 3 months of Day 0) that must be repeated prior to Baseline, and perform 6-minute walk test.

During the Lead-in Infusion (Day 0) the following procedures are performed: Measure vital signs (BP, PR, respiratory rate, temperature), venous sheath placement for right heart catheterization (The sheath will remain following the baseline study, and the patient is hospitalized where they receive the 24-hour levosimendan infusion (preferably through the venous sheath). The sheath is then used for access for the right heart catheterization study following the 24-hour levosimendan infusion, and then removed), right heart catheterization measurements: baseline (prior to levosimendan infusion) and post 24-hour infusion to establish qualifying baseline hemodynamics at rest and exercise and to establish qualifying response to levosimendan during exercise, assess adverse events, assess concomitant medications and/or procedures, pharmacokinetic sampling (to be taken at the end of infusion: 24+/−2 hours), genotyping sampling (to be taken at the end of infusion: 24+/−2 hours). Subjects who do not respond to levosimendan based on hemodynamic measurements are withdrawn from screening. A PICC line is placed in patients that meet eligibility criteria and who are randomized into the Double-Blind phase of the study.

Once eligibility is confirmed via hemodynamic measurements, post-lead-in infusion, subjects are randomized 1:1 to either receive levosimendan or placebo. This occurs at the same visit as the lead-in dose day (Day 0).

Visits at Weeks 2, 3, 4, and 5 are performed within +/−48 hours of the scheduled visit. Visits for Weeks 2-5 are calculated based on the date of the Lead-in infusion. These visits are performed at the subject's home with the aid of the home health care nurse. The home health care nurse remains with the patient for the first 2-3 hours of the infusion to ensure patient safety. The home health care nurse visits the patient again at 24 hours to stop the infusion and assess the patient's status. During this visit, the following procedures are performed: Record any changes in procedures, prescription and non-prescription drugs, vitamins, and dietary or herbal supplements; measure vital signs prior to starting the infusion, after the first 2 hours (+/−30 min), and after 24 hours (+/−30 min); assess adverse events and study drug administration. At Week 5, all patients are given a new cardiac monitoring sensor to wear on their chest to measure cardiac rhythm, as was done during Screening. The patch is applied prior to (<1 hour) the 24-hour infusion, remain monitoring the patient for a minimum of 72 hours and returned to the investigational site at the Week 6 visit.

The Interim Office Visit is performed 48 hours prior to the Week 4 infusion visit. This visit is performed at the investigator's office. Infusions do occur at the office during these visits. During this visit, the following procedures are performed: 6-minute walk test, quality of life (QOL) assessment, NYHA Functional Class determination, body weight, dispense cardiac monitoring patch, and all procedures listed in the Weekly infusion visits with the exception of infusion.

Visits at Week 6 should be performed 3-6 days following completion of the Week 5 infusion. During this visit, the following procedures are performed: record any changes in procedures, prescription and non-prescription drugs, vitamins, and dietary or herbal supplements; measure vital signs (BP, PR, respiratory rate, temperature); hematology and clinical chemistry blood samples: conduct 12-lead ECG; echocardiogram within +/−72 hours of the Week 6 visit: right heart catheterization at rest and with exercise; QOL assessment; Child-Pugh Class, NYHA Functional Class, assess adverse events, 6 minute walk test; and pharmacokinetic sampling (sample to be taken prior to enrollment in Open-Label phase.

The 6-minute walk test (6 MWT) is performed at approximately the same time of day at each study visit after the Baseline Visit and ideally, one of the first assessments to be performed. The ECHO and subject questionnaire are performed after the 6 MWT has been completed. The 6 MWT is performed using the methods described in the American Thoracic Society (ATS) Statement: Guidelines for the Six-Minute Walk Test. The test is performed at approximately the same time of day when assessed and by the same evaluator whenever possible.

The 2-dimensional (2D) echocardiogram complete with contrast is performed by trained personnel. These assessments are standard transthoracic 2D echocardiograms (with contrast to optimize accuracy and precision of intracardiac measurements. These may include, but are not limited to: left ventricular systolic and diastolic function, size, mass, and geometry; right ventricular size and function; pulmonary artery size; left atrial dimensions, volumes, and pressures; valvular (aortic, mitral, tricuspid and pulmonary) stenosis and regurgitation (severity); and pulmonary artery systolic pressure (PASP) and inferior vena cava (IVC) caliber.

Vital signs and body weight include: body temperature, heart rate, respiratory rate, and blood pressure (systolic and diastolic blood pressure). Blood pressure is determined by cuff (using the same method, same arm, and in the same position throughout the study).

All blood laboratory test collections must be performed prior to study drug dosing (where other exclusions do not apply). Blood specimens and serum chemistry are collected, and results obtained by local laboratories, except for the pharmacokinetic and genotyping samples. These samples are sent to external labs for analysis of Levosimendan, OR-1855 and OR-18% metabolites. All clinical laboratory assays will be performed according to the laboratory's normal procedures. Reference ranges are supplied by the laboratory and used to assess the clinical laboratory data for clinical significance and out-of-range pathological changes.

The Hematology and Coagulation Panel includes the following tests: hematocrit, hemoglobin, white blood cell (WBC) count with differential, platelet count, prothrombin time, and partial thromboplastin time.

The Serum Chemistry Panel includes the following test: sodium, potassium, bicarbonate, blood urea nitrogen (BUN), and creatinine.

Results

Primary and Secondary Outcome Measures from Open-Label Lead-in Phase of the HELP Study—First 30 Randomized Patients (~3% of Planned Enrollment)

Figure 1B:
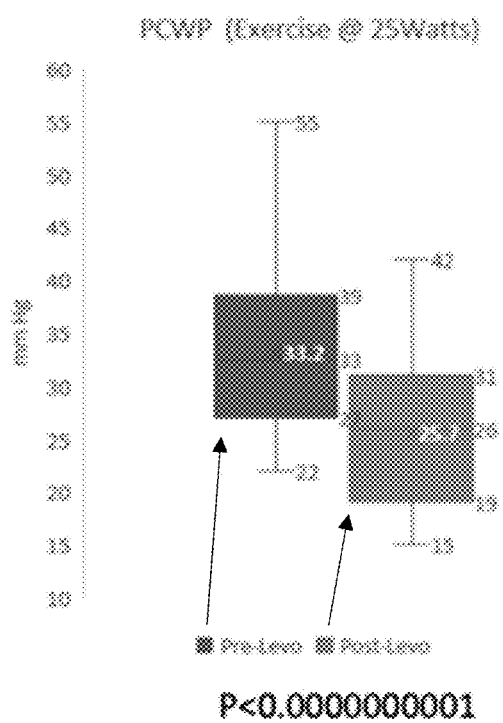

Treatment with weekly 24-hour infusions of 0.075-0.1 μg/kg/min of levosimendan reduces pulmonary capillary wedge pressure during rest by an average of 5.8 mmHg (23.4 to 17.6 mmHg), and during 25 watts of exercise by an average of 7.53 mmHg (33.2 to 25.7 mmHg). These results are presented in FIG. 1.

| | | PCWP | | | | | |
|---|---|---|---|---|---|---|---|
| | | PCWP-Rest (down) | | | PCWP Exercise | | |
| Patient | ID | Pre-Levo | Post-Levo | Change | Pre | Post | Change |
| 1 | 9001 | 28 | 14 | −14 | 37 | 31 | −6 |
| 2 | 9002 | 25 | 23 | −2 | 32 | 28 | −4 |
| 3 | 9003 | 28 | 27 | −1 | 42 | 37 | −5 |
| 4 | 9004 | 21 | 20 | −1 | 26 | 20 | −6 |
| 5 | 9005 | 23 | 19 | −4 | 36 | 28 | −8 |
| 6 | 9006 | 20 | 17 | −3 | 35 | 27 | −8 |
| 7 | 9007 | 22 | 19 | −3 | 40 | 33 | −7 |
| 8 | 17001 | 20 | 12 | −8 | 30 | 23 | −7 |
| 9 | 17004 | 32 | 21 | −11 | 55 | 42 | −13 |
| 10 | 17006 | 17 | 18 | 1 | 40 | 35 | −5 |
| 11 | 4001 | 24 | 12 | −12 | 30 | 20 | −10 |
| 12 | 4002 | 20 | 23 | 3 | 22 | 15 | −7 |
| 13 | 4003 | 27 | 21 | −6 | 35 | 31 | −4 |
| 14 | 7002 | 32 | 14 | −18 | 40 | 18 | −22 |
| 15 | 16001 | 29 | 16 | −13 | 36 | 28 | −8 |
| 16 | 010002 | 23 | 21 | −2 | 32 | 28 | −4 |

-continued

| | | PCWP | | | | | |
|---|---|---|---|---|---|---|---|
| | | PCWP-Rest (down) | | | PCWP Exercise | | |
| Patient | ID | Pre-Levo | Post-Levo | Change | Pre | Post | Change |
| 17 | 019002 | 30 | 17 | −13 | 44 | 30 | −14 |
| 18 | 21001 | 32 | 29 | −3 | 38 | 33 | −5 |
| 19 | 110003 | 20 | 17 | −3 | 23 | 18 | −5 |
| 20 | 21002 | 20 | 14 | −6 | 24 | 18 | −6 |
| 21 | 10003 | 19 | 17 | −2 | 27 | 22 | −5 |
| 22 | 21003 | 22 | 17 | −5 | 27 | 18 | −9 |
| 23 | 9008 | 20 | 8 | −12 | 32 | 23 | −9 |
| 24 | 19004 | 20 | 22 | 2 | 30 | 24 | −6 |
| 25 | 21004 | 20 | 20 | 0 | 22 | 15 | −7 |
| 26 | 17010 | 18 | 8 | −10 | 25 | 19 | −6 |
| 27 | 19006 | 20 | 15 | −5 | 30 | 25 | −5 |
| 28 | 21005 | 22 | 13 | −9 | 33 | 19 | −14 |
| 29 | 21006 | 27 | 16 | −11 | 34 | 29 | −5 |
| 30 | 22002 | 20 | 17 | −3 | 40 | 34 | −6 |
| | | | Avg | −5.800 | | Avg | −7.53 |
| | | | t Test P Value | 0.0000020 | | t Test P Value | 0.0000000000140 |

Treatment with weekly 24-hour infusions of 0.075-0.1 g/kg/min of levosimendan reduces right atrial pressure during rest by an average of 4.83 mmHg (16.2 to 11.3 mmHg), and during 25 watts of exercise by an average of 4.97 mmHg (27.9 to 23.0 mmHg). These results are presented in FIG. 2.

| | | RAP | | | | | |
|---|---|---|---|---|---|---|---|
| | | RAP (Rest-down) | | | RAP (Exercise) | | |
| Patient | ID | Pre | Post | Change | Pre | Post | Change |
| 1 | 9001 | 15 | 10 | −5 | 33 | 25 | −8 |
| 2 | 9002 | 21 | 19 | −2 | 37 | 38 | 1 |
| 3 | 9003 | 27 | 18 | −9 | 40 | 37 | −3 |
| 4 | 9004 | 25 | 20 | −5 | 40 | 38 | −2 |
| 5 | 9005 | 23 | 15 | −8 | 34 | 29 | −5 |
| 6 | 9006 | 17 | 12 | −5 | 27 | 26 | −1 |
| 7 | 9007 | 20 | 17 | −3 | 42 | 34 | −8 |
| 8 | 17001 | 9 | 5 | −4 | 21 | 17 | −4 |
| 9 | 17004 | 8 | 4 | −4 | 13 | 10 | −3 |
| 10 | 17006 | 12 | 12 | 0 | 26 | 20 | −6 |
| 11 | 4001 | 12 | 7 | −5 | 28 | 16 | −12 |
| 12 | 4002 | 11 | 12 | 1 | 35 | 24 | −11 |
| 13 | 4003 | 21 | 18 | −3 | 35 | 36 | 1 |
| 14 | 7002 | 26 | 3 | −23 | 36 | 18 | −18 |
| 15 | 16001 | 13 | 8 | −5 | 21 | 12 | −9 |
| 16 | 010002 | 13 | 12 | −1 | 27 | 22 | −5 |
| 17 | 019002 | 16 | 9 | −7 | 28 | 20 | −8 |
| 18 | 21001 | 20 | 13 | −7 | 43 | 29 | −14 |
| 19 | 110003 | 17 | 13 | −4 | 27 | 25 | −2 |
| 20 | 21002 | 15 | 10 | −5 | 22 | 16 | −6 |
| 21 | 10003 | 11 | 11 | 0 | 22 | 25 | 3 |
| 22 | 21003 | 19 | 12 | −7 | 22 | 28 | 6 |
| 23 | 9008 | 12 | 8 | −4 | 20 | 17 | −3 |
| 24 | 19004 | 15 | 15 | 0 | 30 | 28 | −2 |
| 25 | 21004 | 18 | 12 | −6 | 11 | 12 | 1 |
| 26 | 17010 | 7 | 1 | −6 | 20 | 12 | −8 |
| 27 | 19006 | 12 | 10 | −2 | 20 | 20 | 0 |
| 28 | 21005 | 12 | 9 | −3 | 19 | 19 | 0 |
| 29 | 21006 | 23 | 14 | −9 | 35 | 20 | −15 |
| 30 | 22002 | 15 | 11 | −4 | 24 | 16 | −8 |
| | | | Avg | −4.83 | | Avg | −4.97 |
| | | | t Test P Value | 0.0000011 | | t Test P Value | 0.00003430 |

Figure 3A:
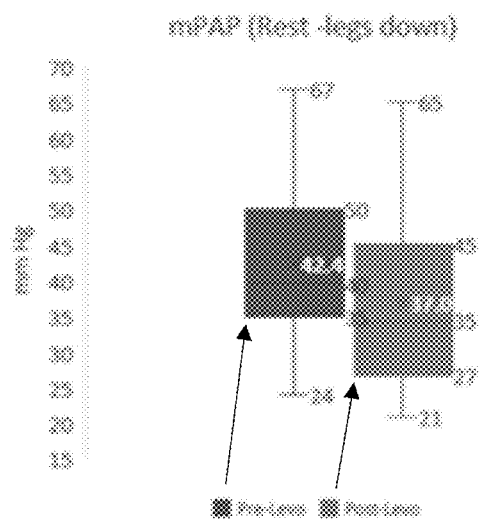
FIGS. 3A-3B: Mean Pulmonary Arterial Pressure (mPAP) Pre vs Post Levosimendan Leand-in Infusion Open-Label Levosimendan Responders (n=30).
Figure 3B:
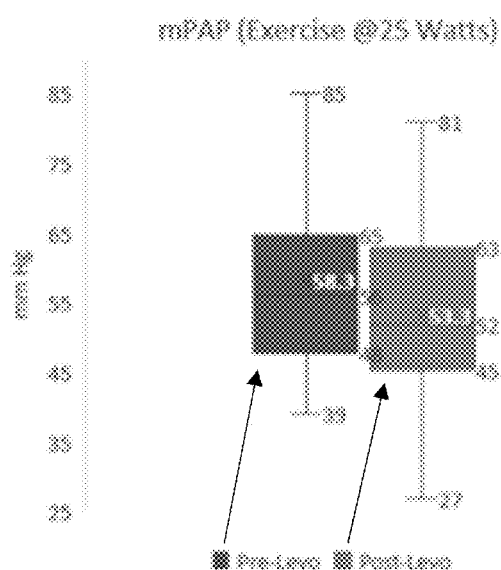

Treatment with weekly 24-hour infusions of 0.075-0.1 g/kg/min of levosimendan reduces mean pulmonary arterial pressure during rest by an average of 5.4 mmHg (42.4 to 37.0 mmHg), and during 25 watts of exercise by an average of 5.1 mmHg (58.3 to 53.3 mmHg). These results are presented in FIG. 3.

| Patient | ID | mPAP Rest (down) | | | mPAP Exercise | | |
|---|---|---|---|---|---|---|---|
| | | Pre-Levo | Post-Levo | Change | Pre | Post | Change |
| 1 | 9001 | 37 | 28 | −9 | 57 | 51 | −6 |
| 2 | 9002 | 57 | 62 | 5 | 84 | 81 | −3 |
| 3 | 9003 | 57 | 57 | 0 | 80 | 68 | −12 |
| 4 | 9004 | 55 | 57 | 2 | 67 | 68 | 1 |
| 5 | 9005 | 67 | 59 | −8 | 74 | 75 | 1 |
| 6 | 9006 | 58 | 49 | −9 | 75 | 62 | −13 |
| 7 | 9007 | 50 | 45 | −5 | 59 | 52 | −7 |
| 8 | 17001 | 35 | 27 | −8 | 50 | 47 | −3 |
| 9 | 17004 | 46 | 35 | −11 | 70 | 67 | −3 |
| 10 | 17006 | 24 | 25 | 1 | 51 | 48 | −3 |
| 11 | 4001 | 31 | 21 | −10 | 55 | 40 | −15 |
| 12 | 4002 | 60 | 65 | 5 | 85 | 80 | −5 |
| 13 | 4003 | 40 | 38 | −2 | 55 | 57 | 2 |
| 14 | 7002 | 50 | 28 | −22 | 60 | 38 | −22 |
| 15 | 16001 | 33 | 21 | −12 | 48 | 35 | −13 |
| 16 | 010002 | 35 | 37 | 2 | 46 | 50 | 4 |
| 17 | 019002 | 42 | 30 | −12 | 60 | 52 | −8 |
| 18 | 21001 | 46 | 37 | −9 | 64 | 55 | −9 |
| 19 | 110003 | 39 | 42 | 3 | 39 | 51 | 12 |
| 20 | 21002 | 36 | 30 | −6 | 42 | 38 | −4 |
| 21 | 10003 | 36 | 41 | 5 | 54 | 52 | −2 |
| 22 | 21003 | 37 | 35 | −2 | 46 | 47 | 1 |
| 23 | 9008 | 31 | 26 | −5 | 52 | 47 | −5 |
| 24 | 19004 | 50 | 46 | −4 | 52 | 58 | 6 |
| 25 | 21004 | 37 | 24 | −13 | 42 | 27 | −15 |
| 26 | 17010 | 40 | 29 | −11 | 64 | 60 | −4 |
| 27 | 19006 | 44 | 34 | −10 | 62 | 66 | 4 |
| 28 | 21005 | 35 | 26 | −9 | 47 | 36 | −11 |
| 29 | 21006 | 38 | 24 | −14 | 46 | 38 | −8 |
| 30 | 22002 | 26 | 32 | 6 | 64 | 52 | −12 |
| | | | Avg | −5.4 | | Avg | −5.1 |
| | | | t Test P Value | 0.00019443 | | t Test P Value | 0.00068 |

Figure 4A:
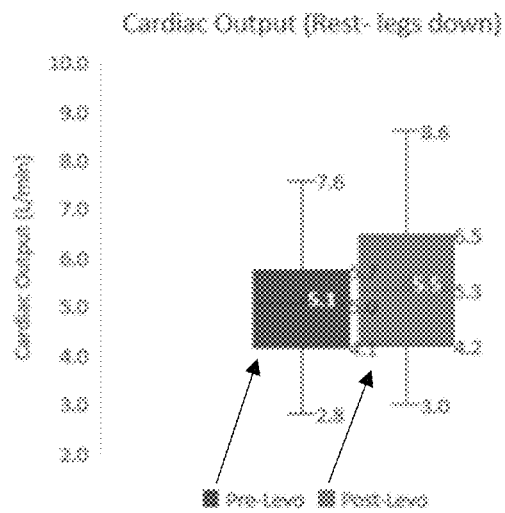
FIGS. 4A-4B: Cardiac Output Pre vs Post Levosimendan Lead-in Infusion Open-label Levosimendan Responders (n=30).
Figure 4B:
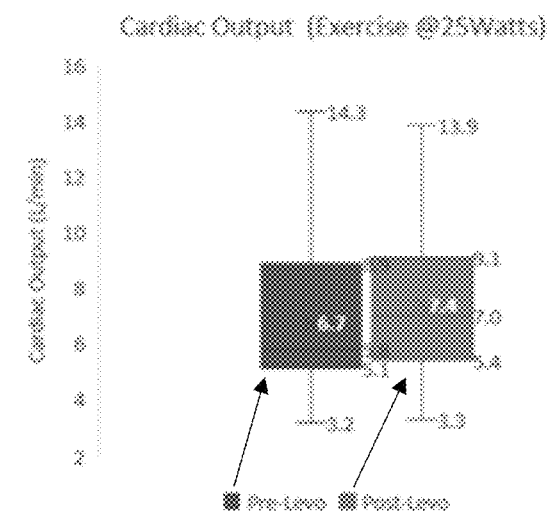

Treatment with weekly 24-hour infusions of 0.075-0.1 μg/kg/min of levosimendan increases cardiac output during rest by an average of 0.33 l/min (5.1 to 5.5 l/min), and during 25 watts of exercise by an average of 0.60 l/min (6.7 to 7.4 l/min). These results are presented in FIG. 4.

| Patient | ID | Rest (down) CO | | | Exercise CO | | |
|---|---|---|---|---|---|---|---|
| | | Pre-Levo Rest | Post-Levo | Change | Pre-Levo Exercise | Post | Change |
| 1 | 9001 | 3.1 | 3.9 | 0.85 | 3.3 | 4.23 | 1.0 |
| 2 | 9002 | 4.3 | 5.4 | 1.06 | 5.5 | 6.93 | 1.4 |
| 3 | 9003 | 4.3 | 5.8 | 1.50 | 5.3 | 6.05 | 0.8 |
| 4 | 9004 | 4.1 | 5.3 | 1.20 | 5.2 | 6.5 | 1.3 |
| 5 | 9005 | 6.1 | 7.0 | 0.87 | 8.2 | 7.7 | −0.5 |
| 6 | 9006 | 2.8 | 3.0 | 0.17 | 3.2 | 3.55 | 0.4 |
| 7 | 9007 | 3.0 | 3.2 | 0.23 | 3.3 | 3.25 | 0.0 |
| 8 | 17001 | 4.2 | 4.5 | 0.27 | 4.7 | 5.5 | 0.8 |
| 9 | 17004 | 3.6 | 3.8 | 0.23 | 5.3 | 5.05 | −0.3 |
| 10 | 17006 | 6.4 | 6.9 | 0.43 | 9.3 | 9.1 | −0.2 |
| 11 | 4001 | 5.1 | 6.2 | 1.06 | 9.1 | 9.1 | 0 |
| 12 | 4002 | 4.1 | 4.2 | 0.05 | 4.4 | 4.68 | 0.3 |
| 13 | 4003 | 4.5 | 5.2 | 0.62 | 4.1 | 5.725 | 1.7 |
| 14 | 7002 | 5.1 | 6.5 | 1.40 | 5.7 | 5.9 | 0.2 |
| 15 | 16001 | 5.4 | 5.3 | −0.07 | 7.3 | 9 | 1.7 |
| 16 | 010002 | 4.9 | 5.6 | 0.67 | 5.8 | 7.65 | 1.8 |
| 17 | 019002 | 5.5 | 7.6 | 2.03 | 9.5 | 11.3 | 1.8 |
| 18 | 21001 | 5.1 | 4.1 | −0.97 | 6.0 | 7.9 | 1.9 |
| 19 | 110003 | 4.9 | 6.0 | 1.03 | 8.8 | 7.1 | −1.7 |
| 20 | 21002 | 7.0 | 8.6 | 1.60 | 8.0 | 12.8 | 4.8 |
| 21 | 10003 | 5.9 | 5.9 | 0.00 | 5.5 | 5.2 | −0.3 |
| 22 | 21003 | 4.1 | 4.3 | 0.20 | 7.6 | 8.0 | 0.4 |
| 23 | 9008 | 7.0 | 6.4 | −0.53 | 9.0 | 10.5 | 1.5 |
| 24 | 19004 | 4.0 | 4.0 | 0.07 | 4.1 | 4.2 | 0.1 |

| Patient | ID | Cardiac Output | | | | | |
|---|---|---|---|---|---|---|---|
| | | Rest (down) CO | | | Exercise CO | | |
| | | Pre-Levo Rest | Post-Levo | Change | Pre-Levo Exercise | Post | Change |
| 25 | 21004 | 11.5 | 11.0 | −0.53 | 14.3 | 13.9 | −0.5 |
| 26 | 17010 | 5.2 | 4.7 | −0.47 | 7.0 | 7.2 | 0.2 |
| 27 | 19006 | 5.1 | 5.3 | 0.13 | 9.8 | 10.6 | 0.8 |
| 28 | 21005 | 7.6 | 6.5 | −1.07 | 12.0 | 11.1 | −1.0 |
| 29 | 21006 | 5.7 | 3.8 | −1.87 | 5.6 | 5.4 | −0.2 |
| 30 | 22002 | 4.7 | 4.4 | −0.30 | 5.6 | 6.5 | 0.9 |
| | | | Avg | 0.33 | | Avg | 0.6 |
| | | | t Test P Value | 0.04563 | | t Test P Value | 0.006588 |

Exploratory Outcome Measures

Hemodynamic response (PCWP decrease) to treatment with weekly 24-hour infusions of 0.075-0.1 μg/kg/min of levosimendan to subjects afflicted with PH-HFpEF can be predicted by a patient's change in stroke volume seen between rest and exercise.

Treatment with weekly 24-hour infusions of 0.075-0.1 μg/kg/min of levosimendan to subjects afflicted with PH-HFpEF results in a greater decrease in pulmonary capillary wedge pressure compared to subjects afflicted with PH-HFpEF treated with a placebo.

Treatment with weekly 24-hour infusions of 0.075-0.1 μg/kg/min of levosimendan to subjects afflicted with PH-HFpEF results in a significantly greater reduction in right atrial pressure compared to subjects afflicted with PH-HFpEF treated with a placebo.

Treatment with weekly 24-hour infusions of 0.075-0.1 μg/kg/min of levosimendan to subjects afflicted with PH-HFpEF results in a significantly greater reduction in mean pulmonary arterial pressure compared to subjects afflicted with PH-HFpEF treated with a placebo.

Treatment with weekly 24-hour infusions of 0.075-0.1 μg/kg/min of levosimendan to subjects afflicted with PH-HFpEF results in a significantly greater increase in cardiac output compared to subjects afflicted with PH-HFpEF treated with a placebo.

Treatment with weekly 24-hour infusions of 0.075-0.1 μg/kg/min of levosimendan to subjects afflicted with PH-HFpEF results in a significantly increased six-minute walk test distance compared to subjects afflicted with PH-HFpEF treated with a placebo.

Treatment with weekly 24-hour infusions of 0.075-0.1 μg/kg/min of levosimendan to subjects afflicted with PH-HFpEF results in a significantly higher proportion of subjects with an improved sense of well-being compared to subjects afflicted with PH-HFpEF treated with a placebo.

Example 2

Brief Summary

An open-label rollover study is conducted to allow patients to continue levosimendan treatment if the patient has tolerated treatment in the HELP clinical study seen in Example 1.

Inclusion Criteria

Completed double-blind therapy in a PH-HFpEF clinical study sponsored by Tenax Therapeutics. Inc.

May, in the opinion of the Investigator, benefit from continued levosimendan treatment.

Female patients of childbearing potential must agree to use a highly effective method of contraception.

Willingness and ability to comply with scheduled visits, treatment plan, laboratory tests and other study procedures.

Exclusion Criteria

Discontinued treatment in the parent study for any reason other than study completion or Sponsor termination of the study.

Pregnant or breastfeeding women.

Local access to commercially available levosimendan.

Inability to comply with planned study procedures.

Patients with scheduled lung or heart transplant or cardiac surgery.

Dialysis developed since enrollment in parent study (either hemodialysis, peritoneal dialysis, continuous venovenous hemofiltration, or ultrafiltration).

Estimated glomerular filtration rate (eGFR)<30 mL/min/$1.73^2$.

Livery dysfunction with Child Pugh Class B or C.

Evidence of systemic bacterial, systemic fungal, or viral infection refractory to treatment.

Weight >150 kg.

Systolic blood pressure (SBP) cannot be managed to ensure SBP≥100 mmHg at initiation of study drug.

Heart rate ≥100 bpm with study drug, persistent for at least 10 minutes at screening.

Hemoglobin <80 g/L.

Serum potassium <3.0 mmol/L or >5.5 mmol/L at baseline that is unresponsive to management.

Description of Study

This is an open-label rollover study to allow patients to continue levosimendan treatment if the patient has tolerated treatment in the HELP clinical study seen in Example 1.

Subjects are visited by the home healthcare nurse until they can satisfactorily demonstrate their ability to self-administer the study drug with a target for self-administration at Weeks 4-6, but not lasting past 8 weeks. After 8 weeks, home healthcare support ceases. Home healthcare visits can be scheduled later in the study if the investigator identifies a clinically urgent need. The subject is instructed on the preparation, administration, and disposal/return of levosimendan (including ancillary supplies) by the home healthcare nurse. The process for distribution of study drug to the subject's home is the same throughout the study Study drug concentrated solution (2.5 mg/mL), levosimendan, is mixed with diluent and administered as weekly infusions at 0.075 μg/kg/min for 24 hrs. Patients may have a dose escalation at Weeks 3 at a rate of 0.10 μg/kg/min for 24 hours, unless there has been a meaningful change in blood pressure or heart rate or other prohibitive rationale.

If a subject was down-titrated to 0.05 µg/kg/min in the HELP study for either the Lead-In or during the double-blind portion of the study, the subject starts at this dose, with the first opportunity to up-titrate at Week 3 of this Open-Label Extension Study.

If at the Week 3 visit the open-label levosimendan has been well-tolerated by the patient, the investigator reviews with the subject the opportunity to convert the PICC line to a port-a-cath in the coming weeks. Some patients may choose to continue use of the PICC line or have a port-a-cath inserted later in the study. Following the placement of a port-a-cath, the home health care nurse visits the subject to assist with the infusions to ensure the patient is self-sufficient in use of the port-a-cath. A subject that chooses to continue with a PICC line after Week 3 is transitioned to a port-a-cath once the PICC line fails or will be discontinued from the study.

At the final visit in the parent study, the Investigator (or an appropriate delegate at the study site) obtains written informed consent from each patient, after which confirmation of eligibility criteria is performed. During the screening visit, the following procedures are performed: Obtain signed main study ICF (must be obtained prior to performance of any study-specific tests or evaluations that are not considered standard of care); confirm inclusion/exclusion criteria, concomitant medications including all prescription and non-prescription drugs, vitamins, and dietary or herbal supplements; perform complete physical examination, including height and body weight; and information documented in the parent study for the following procedures is transferred to the eCRF of the current study.

Weekly visits, occurring approximately every 7 days, are performed within 48 hours of the scheduled visit. The first infusion for this extension study is typically scheduled a week after the last dose (Week 5) of the HELP study. As some patients will be receiving active study drug (levosimendan) for the first time (i.e., they were receiving placebo in the HELP study), subjects are visited by the home healthcare nurse to assure safety and tolerability through 8 weeks from the initiating the Open-Label Extension Study.

Subjects are visited by the home healthcare nurse until they can satisfactorily demonstrate their ability to self-administer the study drug, with a target for self-administration 4-6 weeks after beginning the study. After 8 weeks, home healthcare support ceases. Home health care visits can be scheduled later in the study if the investigator identifies a clinically urgent need. Once a subject adequately demonstrates their ability to self-administer the study drug, the procedures listed below will become not-applicable, other than reporting any adverse events to the investigational site. These visits may be performed at the subject's home. Subjects are instructed to inform the investigator of any infusion related events or AEs that occur during this visit. During these visits, the following procedures are performed (as applicable): Record any changes in procedures, prescription and non-prescription drugs, vitamins, and dietary or herbal supplements; measure vital signs; assess adverse events; and study drug administration and accountability.

At the Week 3 office visit, patients are assessed for potential up-titration to 1.0 µg/kg/min for 24 hours. The decision to increase the dose is based on the absence of disease or drug related adverse events and the investigator's discretion.

Visits at Weeks 3, 6, 12, 24, 48 and Follow-Up Visit (at termination) are performed within 72 hours of the scheduled weekly visit. These visits are performed at the investigator's office. The Follow-Up Visit (at termination) is calculated as the earlier of two years from the subject's date of entry into this extension study or as soon as possible after study discontinuation, but within 1 week. During this visit, the following procedures are performed: Vital signs; body weight (Week 3 only); 6 MWT; Quality of Life assessment; NYHA Functional Class; Physician Assessment; assess adverse events, and concomitant medications and/or procedures.

Results

Figure 5:
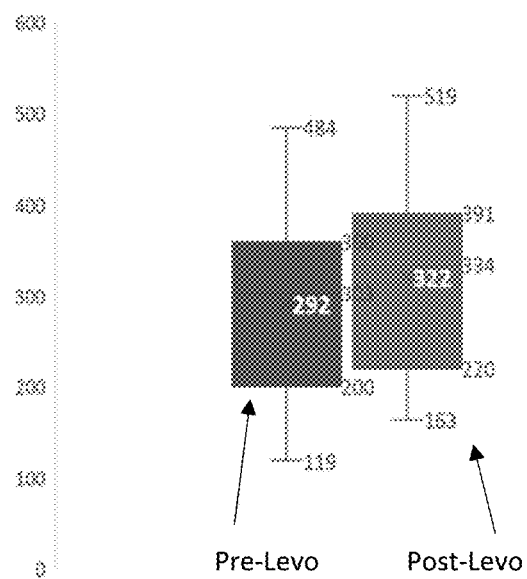
FIG. 5: Six Minute Walk Distance Open-Label Extension Study (n=8).

Treatment with weekly 24-hour infusions of 0.075-0.1 µg/kg/min of levosimendan increases exercise capacity as measured by six-minute walk distance by an average of 30 meters (292 to 322 meters). These results are presented in FIG. 5.

Figure 6:
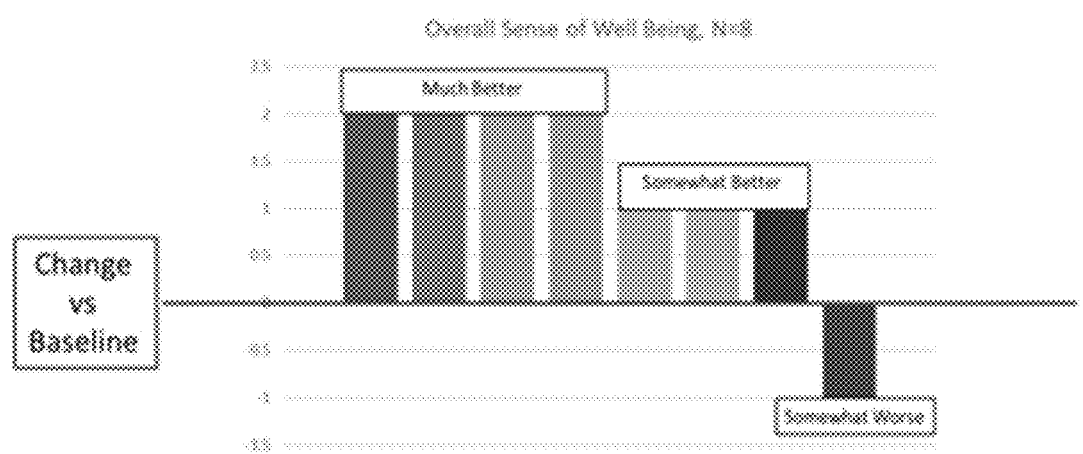
FIG. 6: Evidence of Improved Quality of Life—Patient Self-Assessment—Extension Study, 5 Point Likert Scale.
Figure 7:
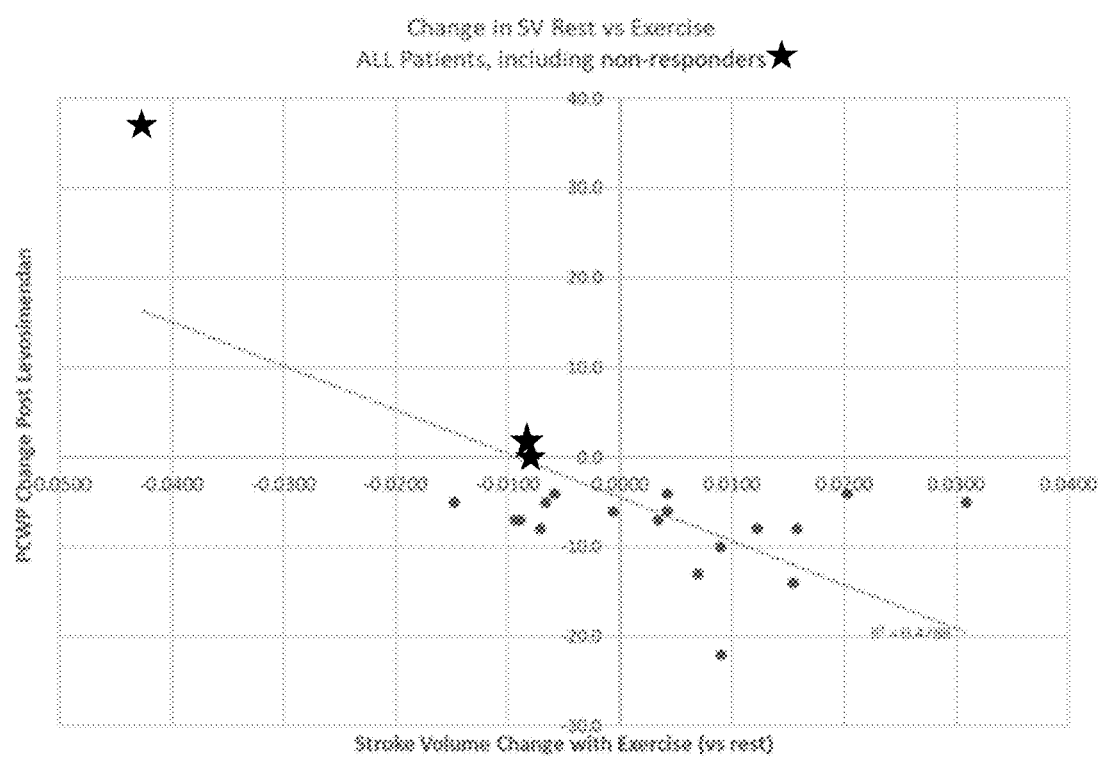
FIG. 7: Exercise Stroke Volume May Predict Response to Levosimendan.
Figure 8:
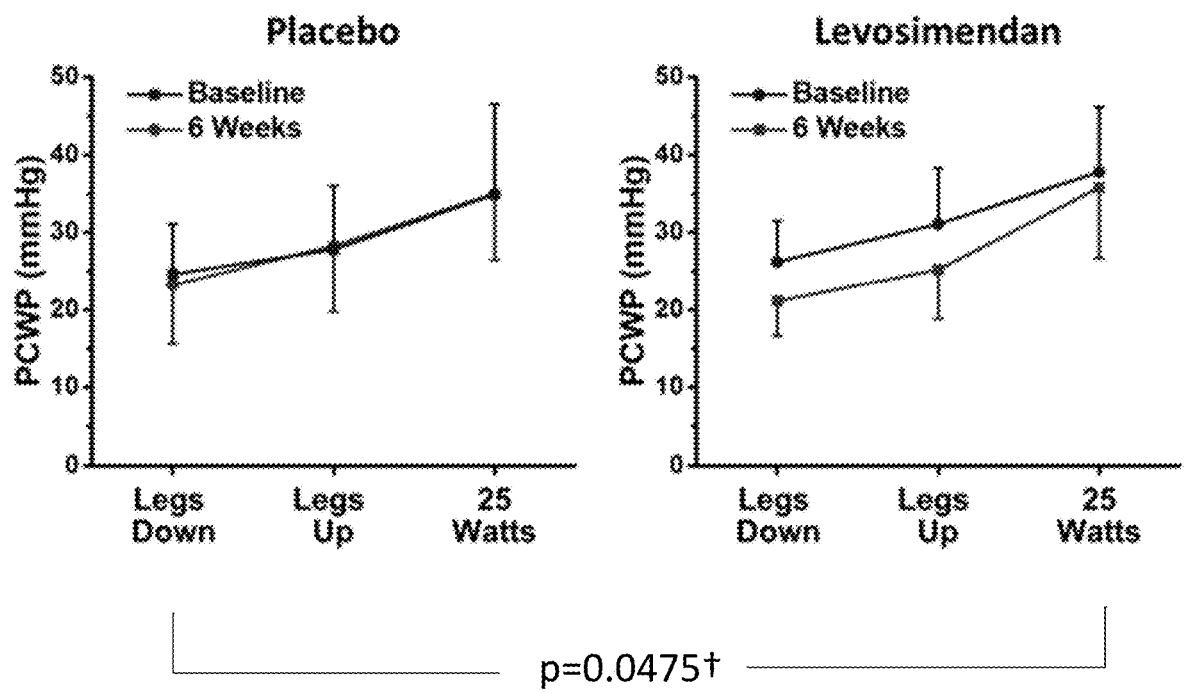
FIG. 8: PCWP Endpoint—Baseline vs. 6 Weeks. Levosimendan effect on PCWP across positions is significant vs placebo.
Figure 9A:
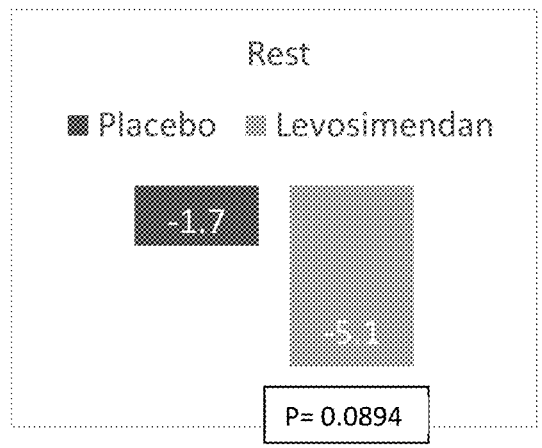
FIGS. 9A-9C: PCWP Change from Baseline at Week 6—Levosimendan vs Placebo.
Figure 9B:
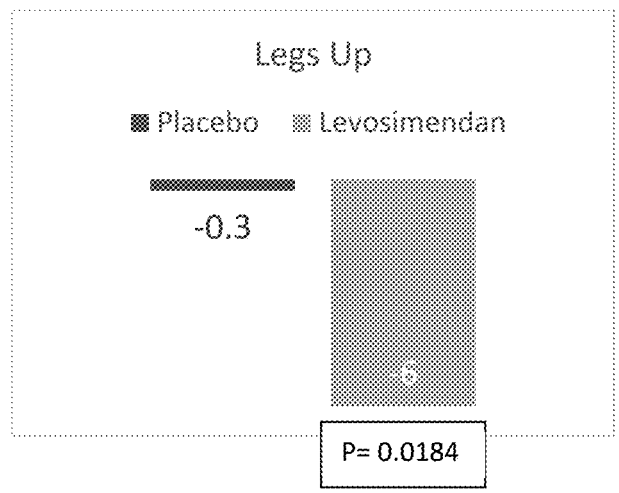
Figure 9C:
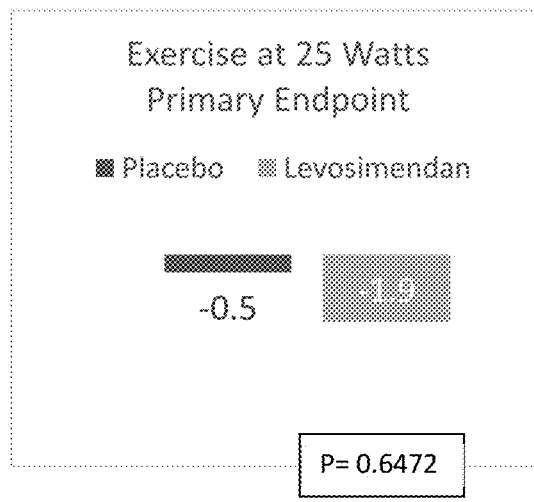
Figure 10:
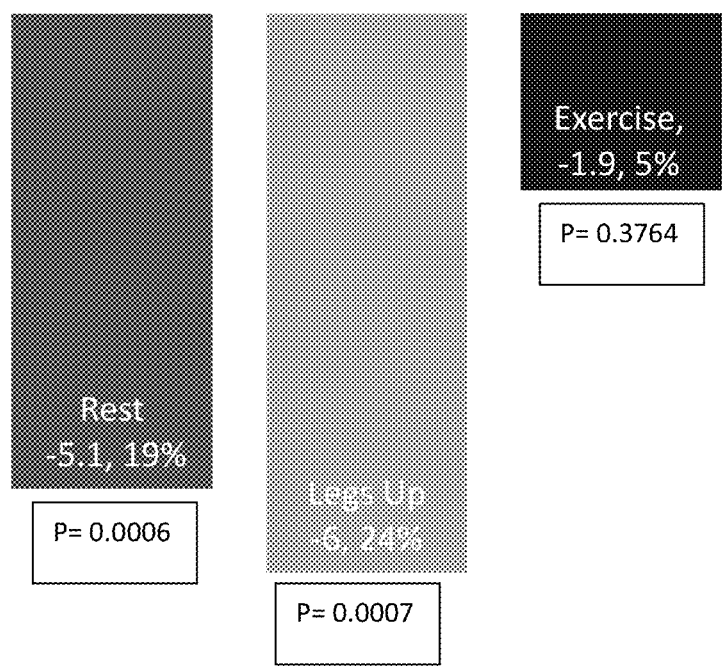
FIG. 10: PCWP Week 6—Levosimendan Change from Baseline.
Figure 11:
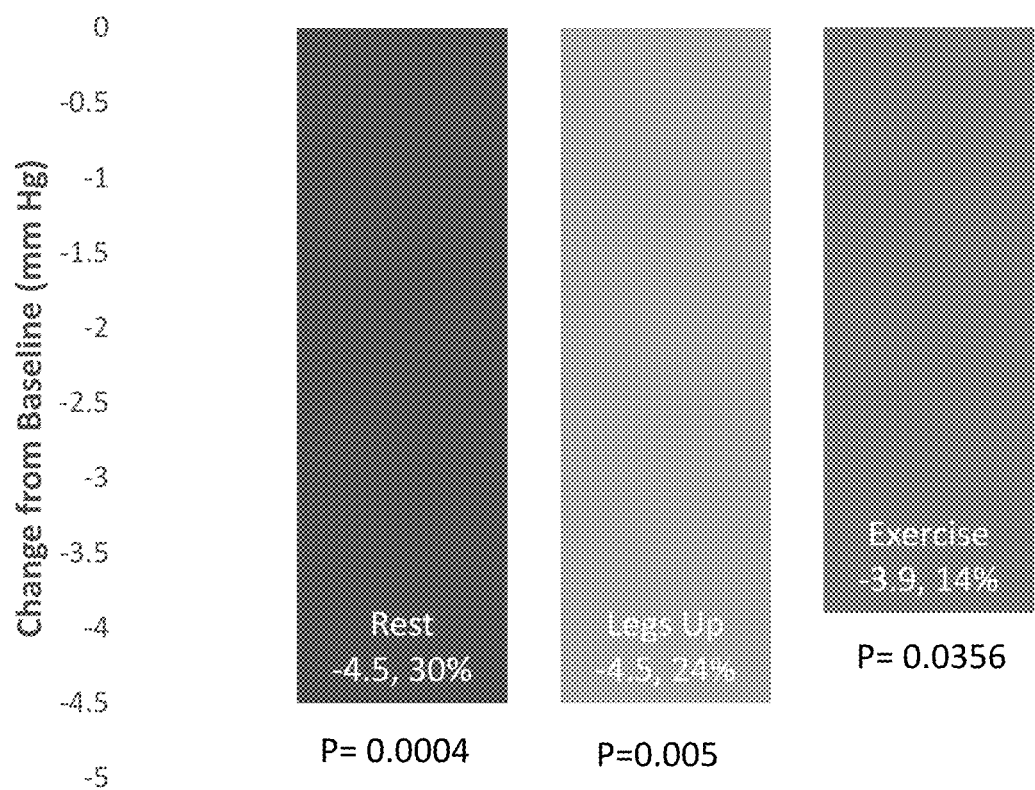
FIG. 11: RAP Change from Baseline at Week 6—Levosimendan Treated Patients.
Figure 12A:
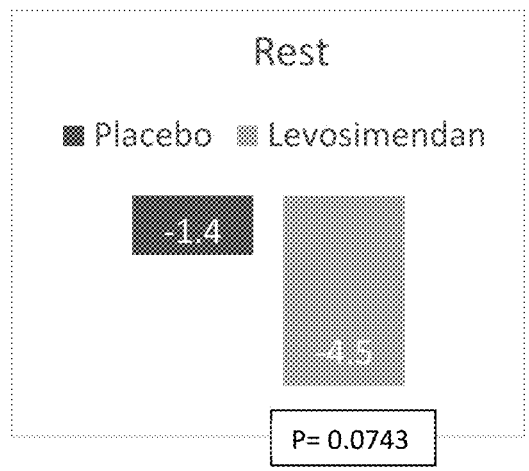
FIGS. 12A-12C: RAP Change at Week 6—Levosimendan vs Placebo.
Figure 12B:
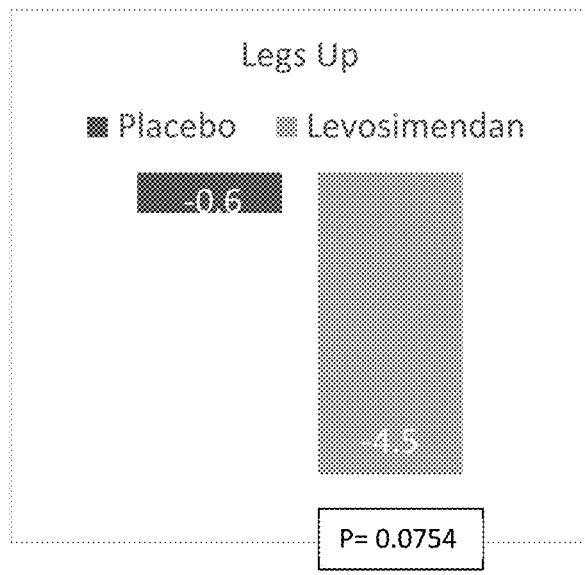
Figure 12C:
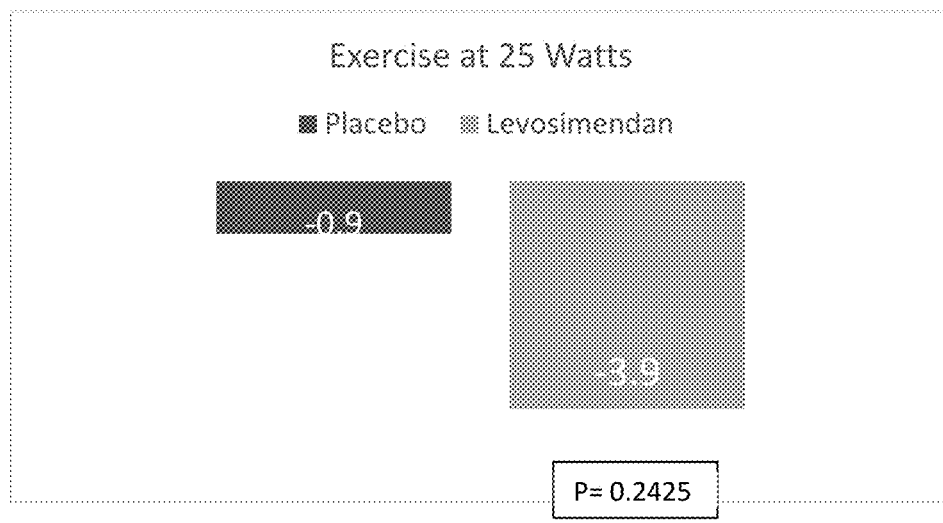
Figure 13:
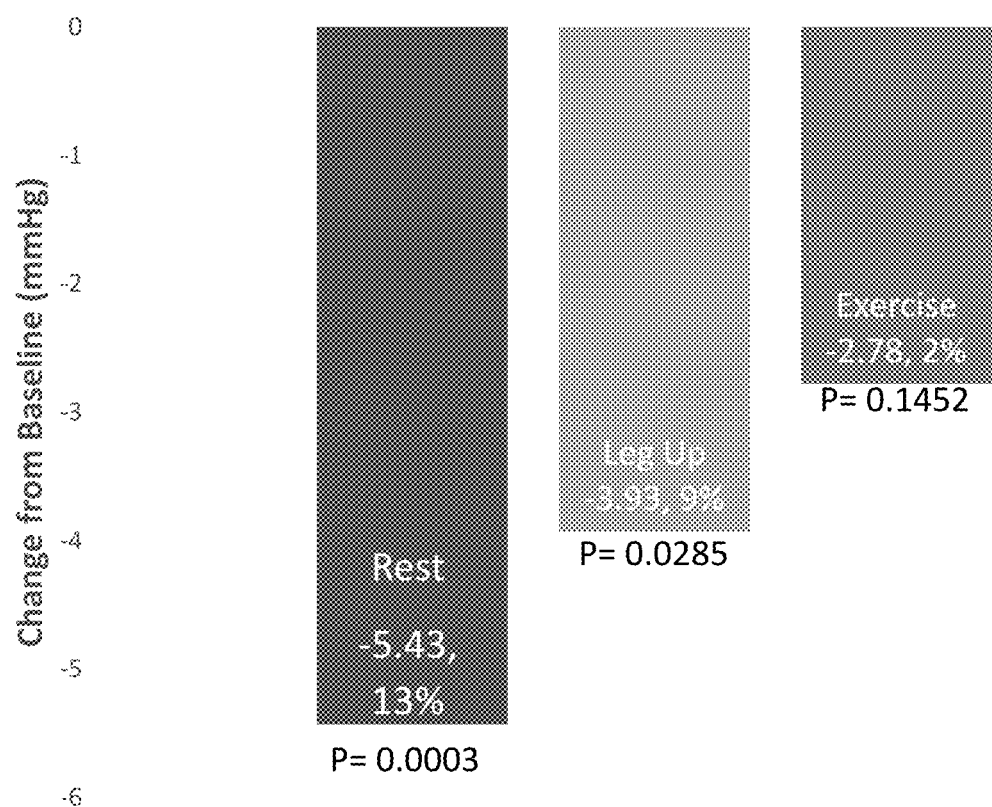
FIG. 13: mPAP Week 6—Levosimendan Change from Baseline.
Figure 14A:
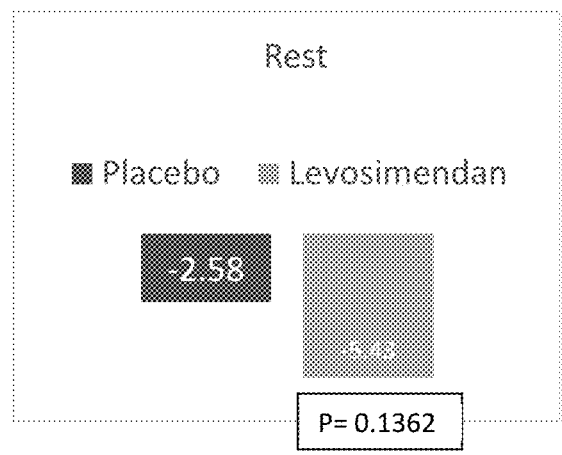
FIGS. 14A-14C: mPAP (mmHg) Change at Week 6—Levosimendan vs Placebo.
Figure 14B:
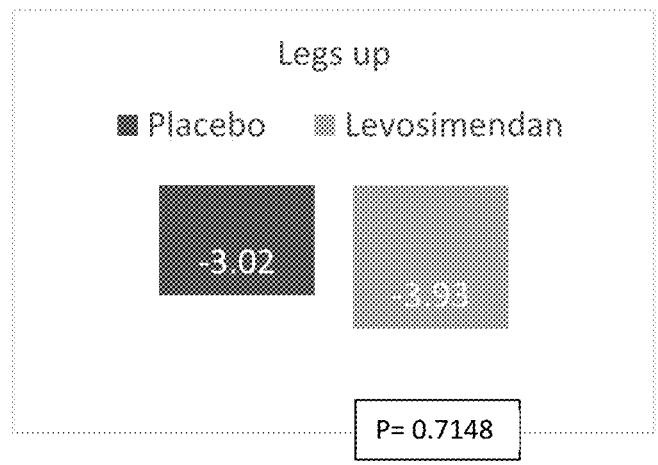
Figure 14C:

Treatment with weekly 24-hour infusions of 0.075-0.1 µg/kg/min of levosimendan increases overall sense of well-being as measured by a five-point Likert Scale in 7 out of 8 patients, with an improvement of 1-2 points on the five-point Likert scale. These results are presented in FIG. 6.

The HELP Study results indicate that weekly 24-hour dosing of Levosimendan improves PCWP (left Heart Failure) in PH-HFpEF.

The HELP Study results indicate that weekly 24-hour dosing of Levosimendan improves 6-Minute Walk Distance (exercise capacity) in PH-HFpEF.

The HELP Study results indicate that weekly 24-hour dosing of Levosimendan improves right atrial pressure (right heart function) in PH-HFpEF.

The HELP Study results indicate that weekly 24-hour dosing of Levosimendan reduces Pulmonary Artery Pressure in PH-HFpEF.

The HELP Study results indicate that weekly 24-hour dosing of Levosimendan is safe and well tolerated.

HELP Study enrolled PH-HFpEF patients with biventricular failure (right and left failure) and therefore the positive results from the trial, support a claim for use in PH-HFpEF patients, including those with biventricular failure.

Example 3

A study is conducted analogous to Example 1. However, certain parameters are modified to allow for a different form of administration.

A subcutaneous levosimendan formulation administered via subcutaneous administration. The subcutaneous formulation will be substantially similar to the intravenous formulation in Example 1.

Results are substantially similar to the result of Example 1, with a decrease in injection site and/or central line infections when compared to intravenous infusion administration. Additionally, an increase in quality of life assessment and/or convenience of administration occurs due to the easier route of delivery.

Example 4

A study is conducted analogous to Example 1. However, certain parameters are modified to allow for the combined administration of levosimendan with additional cardiovascular drugs.

A levosimendan formulation is administered substantially as in Example 1, but administered in combination with Entresto.

Results are substantially similar to Example 1, with an improvement in cardiovascular hemodynamics, exercise performance, and quality of life.

Example 5

A study is conducted analogous to Example 1. However, certain parameters are modified to allow for the combined administration of levosimendan with additional cardiovascular drugs A levosimendan formulation is administered substantially as in Example 1, but administered in combination with Sacubitril and/or other neprilysin inhibitors.

Results are substantially similar to Example 1, with an improvement in cardiovascular hemodynamics, exercise performance, and quality of life.

Example 6

A study is conducted analogous to Example 1. However, certain parameters are modified to allow for the combined administration of levosimendan with additional cardiovascular drugs.

A levosimendan formulation is administered substantially as in Example 1, but administered in combination with Ranolazine.

Results are substantially similar to Example 1, with an improvement in cardiovascular hemodynamics, exercise performance, and quality of life.

Example 7

Brief Summary

A pharmacokinetic study was conducted in male Sprague Dawley rats to compare subcutaneous administration of a composition of the present invention with IV administration of a formulation of levosimendan. The study evaluated levosimendan blood levels and pain at the injection site.

Methodology

This study involved comparing the results of administering two subcutaneous compositions according to embodiments of the present invention to a previous pharmacokinetic study in which male rats were dosed by tail vein levosimendan as an IV bolus injection at 0.5 mg/kg using a 0.25 mg/ml solution. Thus, this study comprised three study arms:

a. IV administration of a composition comprising levosimendan (0.25 mg/ml) and phosphate buffer (10 mmolar), prepared in sterile water for injection and adjusted to a pH of 7.0 to 7.9 using 1 N NaOH or 10 N NaOH; this composition was administered at a dose of 0.5 mg/kg.

b. Subcutaneous administration of a composition comprising levosimendan (1.0 mg/ml), Captisol® (100 mg/ml), and phosphate buffer (10 mmolar), prepared in sterile water for injection and adjusted to a pH of 7.0 to 7.9 using 1 N NaOH or 10 N NaOH; this composition was administered at a dose of 0.5 mg/kg.

c. Subcutaneous administration of a composition comprising levosimendan (1.0 mg/ml), Captisol® (300 mg/ml), and phosphate buffer (10 mmolar), prepared in sterile water for injection and adjusted to a pH of 7.0 to 7.9 using 1 N NaOH or 10 N NaOH; this composition was administered at a dose of 0.5 mg/kg.

Each of the compositions was sterile filtered using a sterile 0.22 micron Millex-GV PVDF filter syringe filter prior to administration.

For the study, naïve male Sprague Dawley rats were used that were between 10 to 12 months old. Blood samples were collected from the rats pre-dose and at the following time points after the dose: 5 min, 15 min, 30 min, 1 hr, 2 hr, 4 hr, 8 hr, 12 hr, and 18 hr. Five 0.5-ml to 1.0-ml blood samples were collected from each rat. Four of these samples were collected from the tail vein and the fifth sample was collected by cardiac puncture following deep anesthesia with isoflurane inhalation and exsanguination. In each study arm, rats were divided into two groups, group A and group B, that contained three rats each. Sample collection points were alternated between three rats in group A and three rats in group B. Thus, samples were collected from group A rats at pre-dose, 15 min, 1 hr, 4 hr and 12 hr. Samples were collected from group B rats at 5 min, 30 min, 2 hr, 8 hr and 18 hr. A thoracotomy was preformed to insure death. Each arm of the study used six rats for a total of 18 rats.

During the study following the subcutaneous and IV injections, the rats were observed for any clinical signs of adverse reactions. Behavior including licking, biting or scratching of the injection area, any loss of mobility, restlessness, unresponsiveness, and abnormal postures was monitored. No abnormal observations occurred, as the rats continued to act normally throughout the study.

Immediately after the rats were euthanized, the subcutaneous injection site along the back between the shoulders was examined for any signs of swelling or irritation. Three rats that received the 100 mg/ml Captisol® formulation for 12 hours and three rats that received the 300 mg/ml Captisol® formulation for 18 hours were compared to three naïve rats with no injection as a control. The epidermis of the rats was carefully removed, exposing the tissue directly surrounding the subcutaneous injection site. No swelling or signs of irritation were observed in the tissue.

Blood samples were stored in tubes containing EDTA as an anticoagulant and kept in an ice bath until centrifuged to separate the plasma. The plasma samples were stored at −20° C. until assayed. Plasma obtained from each of the samples was used for liquid chromatographic/mass spectroscopic analysis of the compound.

Plasma samples were analyzed for levosimendan and OR-1896 (the primary metabolite) by HPLC/MS/MS. A protein precipitation method was employed for sample preparation by the addition of an acetonitrile spiking solution or acetonitrile, and internal standard to a plasma sample or blank plasma. The internal standard for levosimendan was 13C6-labeled levosimendan, and for OR-1896 was 13C6-labeled ORM-25632 (racemic form of OR-1896). After addition of reagents, the mixture was vortexed and centrifuged. Approximately 75-80 µl was transferred to an autosampler vial with a plastic insert.

The HPLC/MS/MS method consisted of a Restek Raptor Biphenyl column, 2.7 µm, 100×3 mm. Mobile phase A consisted of 5 mM Ammonium Formate/0.1% Formic acid and mobile phase B was methanol. The flow rate was set to 0.6 m/min and injection volume was 10 µl. Detection was performed with a Sciex 3200 Qtrap mass spectrometer in MRM mode.

Results

Figure 2A:
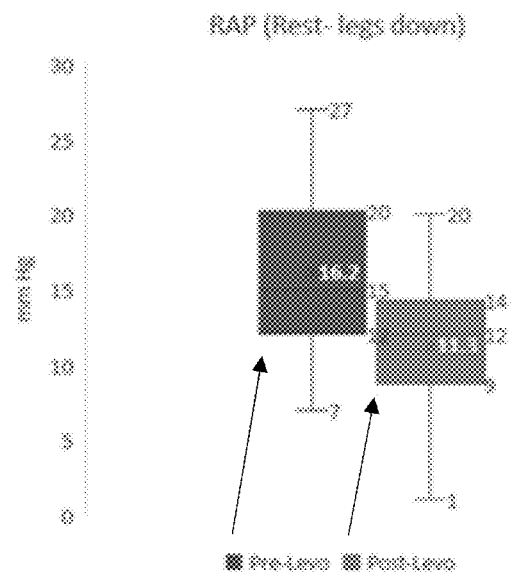
FIGS. 2A-2B: Right Atrial Pressure (RAP) Pre vs Post Levosimendan Lead-in Infusion Open-Label Levosimendan Responders (n=30) is a graphical representation of results of Example 1, showing a decrease in right atrial pressure (RAP) after levosimendan administration in 30 patients. These results are based on single 24-hour open label lead-in infusion data.
Figure 2B:
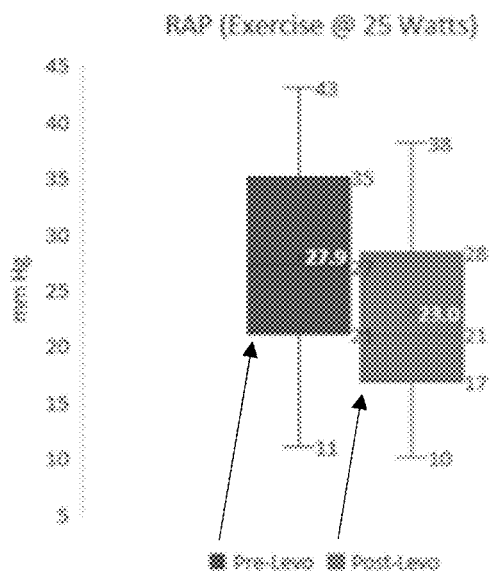

Levosimendan plasma concentrations after IV and subcutaneous dosing. The higher initial plasma levels for the IV formulation are typical for an IV injection. The more rapid initial decrease in the blood levels (α phase) is the distribution of the drug throughout the tissues in the body. After the initial distribution of the drug, the loss of drug from the blood is mainly due to metabolism (β phase). In levosimendan, the . . . phase starts at about 2 hours. Notably, Table 7 and FIG. 2 show that the metabolism of levosimendan is very similar for the IV and the subcutaneous compositions. This is also supported by the nearly identical results for the plasma levels of the primary active metabolite OR-1896.

| Time | IV Formulation | | Subcutaneous Composition (100 mg/ml Captisol ®) | | Subcutaneous Composition (300 mg/ml Captisol ®) | |
|---|---|---|---|---|---|---|
| | Concentration (ng/ml) | Std. Dev. | Concentration (ng/ml) | Std. Dev. | Concentration (ng/ml) | Std. Dev. |
| Pre-Dose | <LOQ | <LOQ | <LOQ | <LOQ | <LOQ | <LOQ |
| 5 min | 2013 | 180 | 402 | 19 | 213 | 56 |
| 15 mm | 4890 | 2973 | 541 | 53 | 361 | 86 |
| 30 min | 3386 | 2238 | 564 | 139 | 422 | 119 |
| 1 hr | 2385 | 2105 | 673 | 83 | 568 | 183 |
| 2 hr | 175 | 46.5 | 337 | 166 | 287 | 42.8 |
| 4 hr | 77.2 | 44.5 | 87.7 | 30.3 | 77.0 | 28.6 |
| 8 hr | 3.0 | 2.0 | 7.9 | 5.4 | 4.8 | 3.0 |
| 12 hr | 1.6 | 0.5 | 1.6 | 0.2 | 6.5 | 2.2 |
| 18 hr | 1.1 | 0.7 | 2.4 | 1.0 | 0.6 | 0.2 |

OR-1896 plasma concentrations after IV and subcutaneous dosing. OR-1896, the major active metabolite of levosimendan, demonstrated very similar plasma concentrations regardless of route of administration or formulation.

| Time | IV Formulation | | Subcutaneous Composition (100 mg/ml Captisol ®) | | Subcutaneous Composition (300 mg/ml Captisol ®) | |
|---|---|---|---|---|---|---|
| | Concentration (ng/ml) | Std. Dev. | Concentration (ng/ml) | Std. Dev. | Concentration (ng/ml) | Std. Dev. |
| Pre-Dose | <LOQ | <LOQ | <LOQ | <LOQ | <LOQ | <LOQ |
| 5 min | <LOQ | <LOQ | <LOQ | <LOQ | <LOQ | <LOQ |
| 15 min | <LOQ | <LOQ | <LOQ | <LOQ | <LOQ | <LOQ |
| 30 min | 0.623 | 0.069 | <LOQ | <LOQ | <LOQ | <LOQ |
| 1 hr | 0.854 | 0.196 | <LOQ | <LOQ | <LOQ | <LOQ |
| 2 hr | 2.340 | 0.416 | 1.690 | 0.197 | 0.946 | 0.298 |
| 4 hr | 3.207 | 0.337 | 3.253 | 0.600 | 2.377 | 0.401 |
| 8 hr | 5.767 | 0.973 | 5.330 | 0.320 | 4.883 | 0.737 |
| 12 hr | 6.347 | 1.325 | 7.173 | 1.255 | 6.037 | 1.053 |
| 18 hr | 5.007 | 3.441 | 4.265 | 0.997 | 4.110 | 1.720 |

Pharmacokinetic parameters for levosimendan after administration of the IV formulation and the subcutaneous compositions. A significantly lower Cmax was observed for both subcutaneous compositions versus the IV formulation, but the half-life for elimination was comparable for all formulations.

| Pharmacokinetic Parameter | Units | IV Formulation | Subcutaneous Composition (100 mg/ml Captisol ®) | Subcutaneous Composition (300 mg/ml Captisol ®) |
|---|---|---|---|---|
| $C_{max}$ | ng/ml | 4890 | 568 | 673 |
| $T_{max}$ | hr | 0.25 | 1 | 1 |
| $AUC_{(0-\infty)}$ | ng/ml*hr | 4932 | 1402 | 1699 |
| $K_{el}$ | $hr^{-1}$ | 0.942 | 0.683 | 0.632 |
| $T_{1/2}$ | hr | 0.736 | 1.015 | 1.097 |
| Cl | ml/hr/kg | 101 | — | — |
| F | % | — | 28 | 34 |

Pharmacokinetic parameters for OR-896 after administration of the IV formulation and the subcutaneous compositions. The Cmax, Tmax, and AUC for both subcutaneous compositions are very similar to the IV route of administration. The bioavailability of OR-1896 is 95-113% from the subcutaneous formulations.

| Pharmacokinetic Parameter | Units | IV Formulation | Subcutaneous Composition (100 mg/ml Captisol ®) | Subcutaneous Composition (300 mg/ml Captisol ®) |
|---|---|---|---|---|
| $C_{max}$ | ng/ml | 6.35 | 6.04 | 7.17 |
| $T_{max}$ | hr | 12 | 12 | 12 |
| $AUC_{(0-\infty)}$ | ng/ml*hr | 83.90 | 71.07 | 83.12 |
| F | % | | 95 | 113 |

These results show that OR-1896 plasma concentrations following administration of the subcutaneous compositions of the invention were comparable to those observed following IV levosimendan administration. This was an unexpected finding given the substantially lower Cmax and AUC of levosimendan observed following the subcutaneous administration of the compositions of the invention as compared to IV administration.

In addition, there was no evidence of pain or visible signs of irritation at the injection site, nor were there any clinical-related adverse events or other signs of pain or distress observed for the rats. The Captisol®-containing subcutaneous compositions did not cause any apparent irritation of adverse reactions when administered subcutaneously.

Example 8

A study is conducted analogous to Example 7. However, certain parameters are modified to allow for the subcutaneous administration of levosimendan.

Results are substantially similar to Example 7, with a decrease in injection site and/or central line infections when compared to intravenous infusion administration. Additionally, an increase in quality of life assessment and/or convenience of administration occurs due to the easier route of delivery.

Discussion

Clinical trials of levosimendan have focused exclusively on HFrEF patients. Patients afflicted with heart failure with preserved ejection fraction (HFpEF), who have an ejection fraction ≥40% have been excluded from these levosimendan clinical trials. One reason that levosimendan has not been studied in HFpEF patients may be the historical concern that inotropes, and particularly calcium sensitizing inotropes such as levosimendan, have been thought to impair ventricular relocation which would be detrimental in HFpEF patients. One example of this safety concern is referenced by Hajar et al. in Cardiovascular Drugs and Therapy that states: "This leads us to the conclusion that inotropic agents that increase the sensitivity of the myofilaments to $CA^{2+}$ further impair relaxation in myopathic hearts, resulting in a reduced contractile reserve and diminished force production."

Examples of major HFrEF clinical trials that have excluded HFpEF patients include: LIDO, REVIVE, SURVIVE, RUSSLAN, and LEVO-CTS. All of these trials have excluded patients with an ejection fraction >36%. In addition, all clinical trials that have evaluated chronic intermittent dosing of levosimendan have excluded HFpEF patients. Examples of clinical trials that have evaluated chronic intermittent dosing of levosimendan that have excluded HFpEF patients include: LIONHEART, LEVOREP, LAICA, and numerous other single-center trials. Kleber et al. conducted a trial on intermittent dosing with levosimendan in patients afflicted with pulmonary hypertension, but this trial also did not recruit HFpEF patients and failed to show efficacy following chronic dosing over an 8-week period. Lastly, Jiang et al. conducted a trial of levosimendan in patients with various types of pulmonary arterial hypertension and acute heart failure; however, none of the patients were PH-HFpEF patients.

Levosimendan dosing in previous acute heart failure trials employed single 24-hour infusions of 0.5 to 0.2 mcg/kg/min to treat acutely decompensated heart failure patients in a hospital setting. Other trials have evaluated repeated or intermittent dosing of levosimendan in chronic heart failure patients, and these studies have employed a range of dosing alternatives that utilize IV infusions of less than 24 hours and administered with a repeated dosing frequency of every 2 to 4 weeks in a hospital setting. No studies to date have employed weekly 24-hour infusions administered outside of a hospital setting.

The data from the HELP study that evaluates the hemodynamic effects of levosimendan in PH-HFpEF patients is the first and only study to evaluate levosimendan in PH-HFpEF patients. Since no drugs have been shown to be effective and safe in PH-HFpEF patients, including numerous drugs that are effective in other forms of pulmonary hypertension, no one could have predicted the results of the HELP Study. In particular, in view of the numerous failed attempts, it was unreasonable to expect that in the HELP study levosimendan would lower PCWP, lower PA pressure, or increase cardiac output, increase 6-minute walk distance, or improve quality of life for PH-HFpEF patients.

Figure 15:
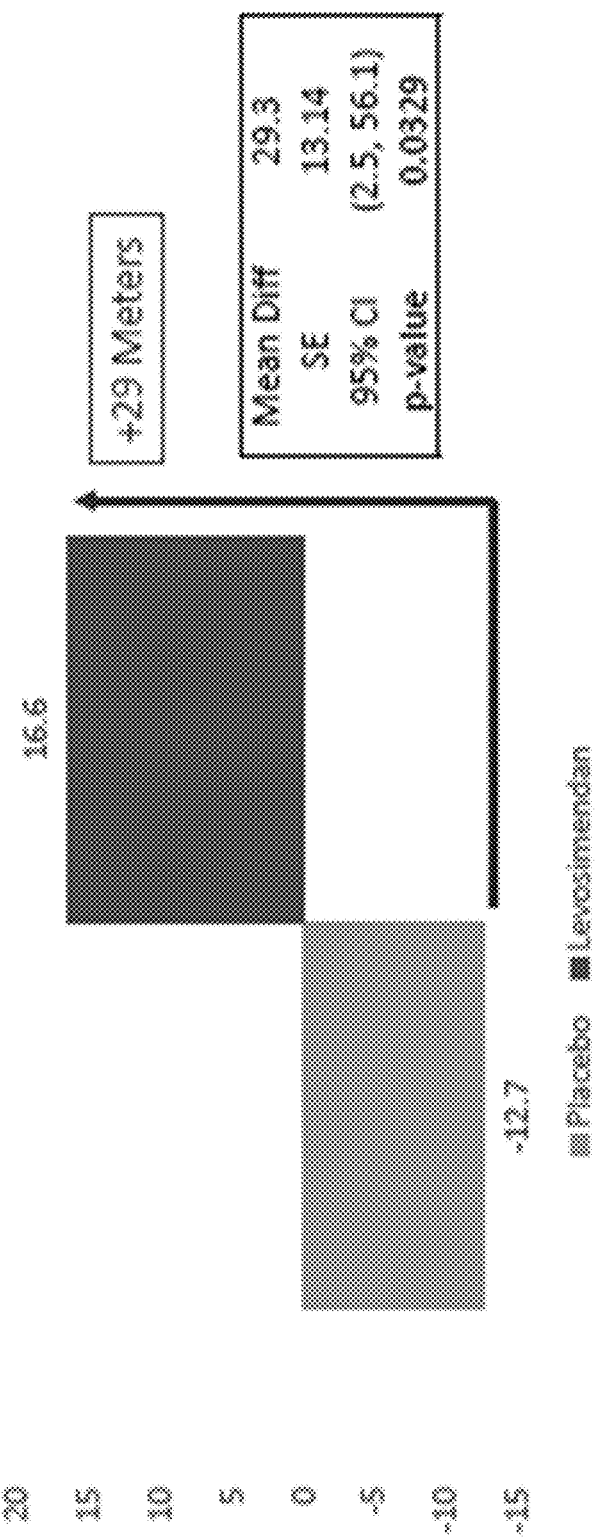
FIG. 15: Change in Six Minute Walk Distance (meters) from Baseline at Week 6—Levosimendan vs. Placebo.
Figure 19:
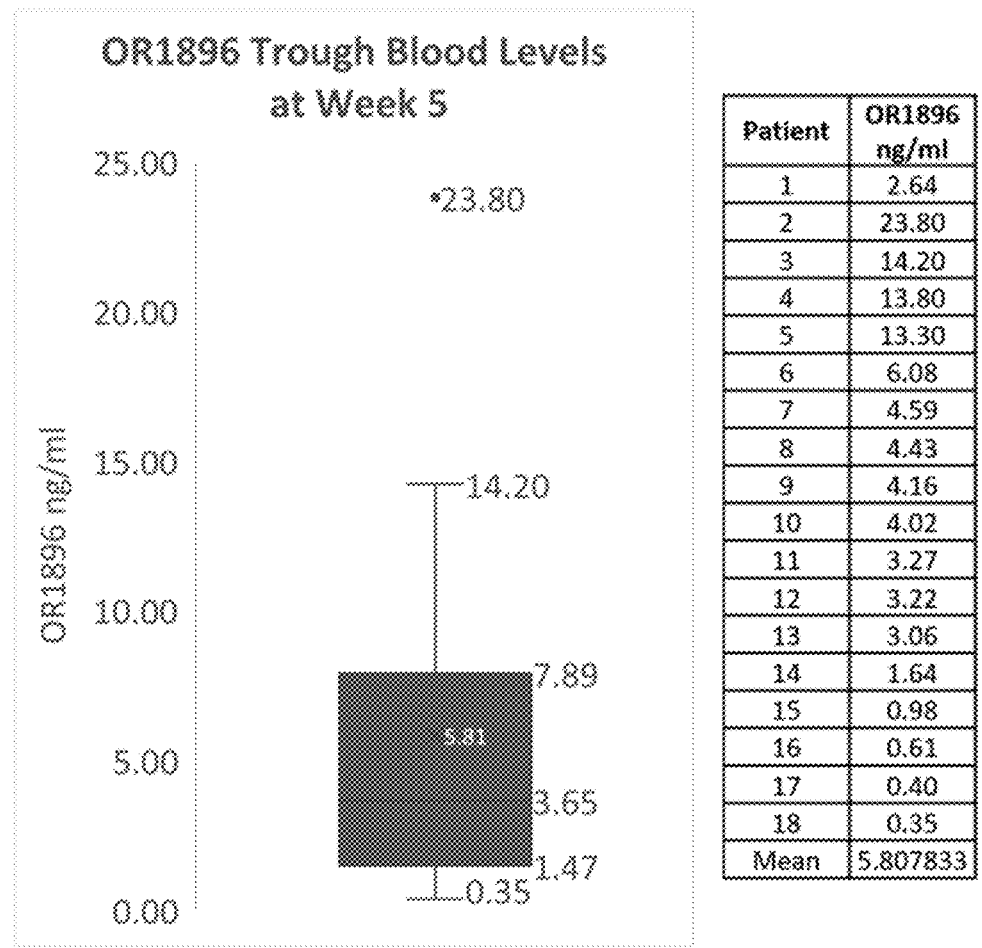
FIG. 19: OR1896 Trough Blood Levels at Final RHC Levosimendan Treated Patients.
Figure 20A:
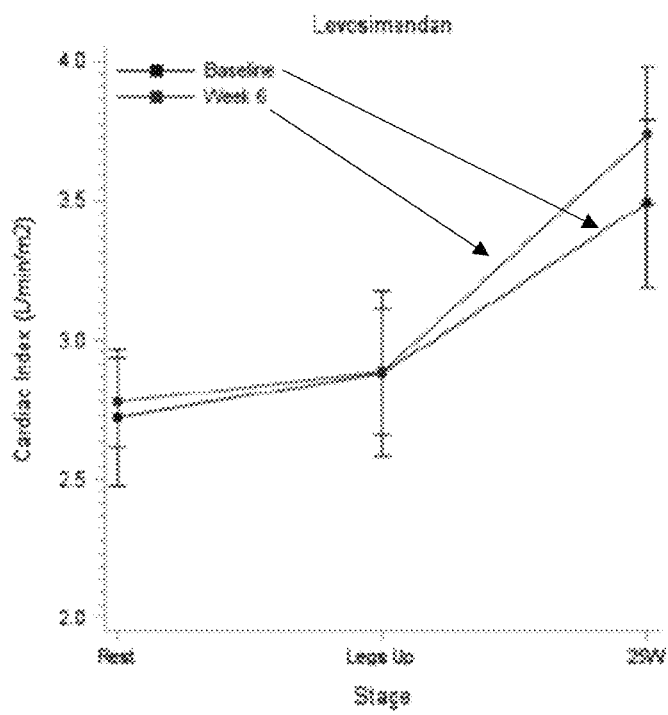
FIGS. 20A-20B are graphical representations of Example 2 results, where levosimendan or placebo was administered via weekly 24-hour IV infusions for a period of 5 weeks to 35 PH-HFpEF patients, showing Cardiac Index (CI) (FIG. 20A) and pulmonary vascular resistance (PVR) (FIG. 20B) after levosimendan administration in 36 PH-HFpEF patients. PVR and CI behaved surprisingly different compared to other variables (i.e. unchanged at week 6). This data suggests that levosimendan is acting differently with respect to chronic (weekly for 5 weeks) vs. acute (24-hour) administration (See, for example, FIGS. 4A-4B).
Figure 20B:
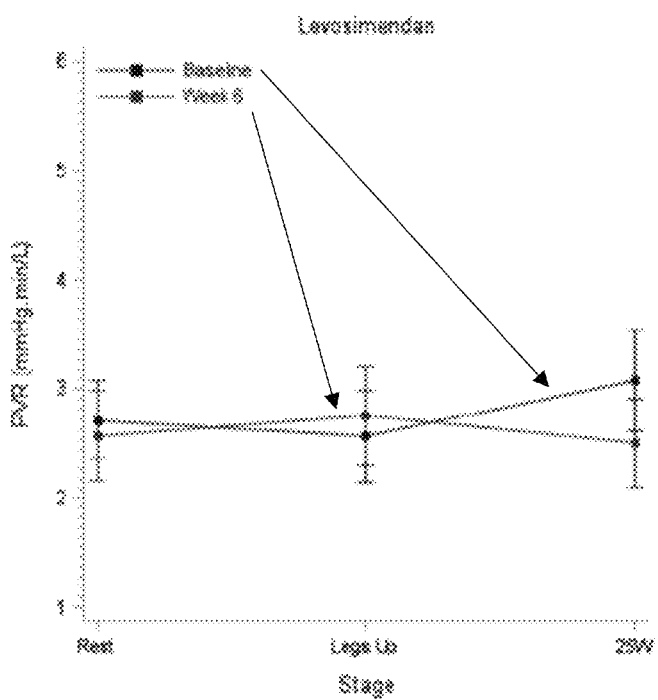
Figure 21A:
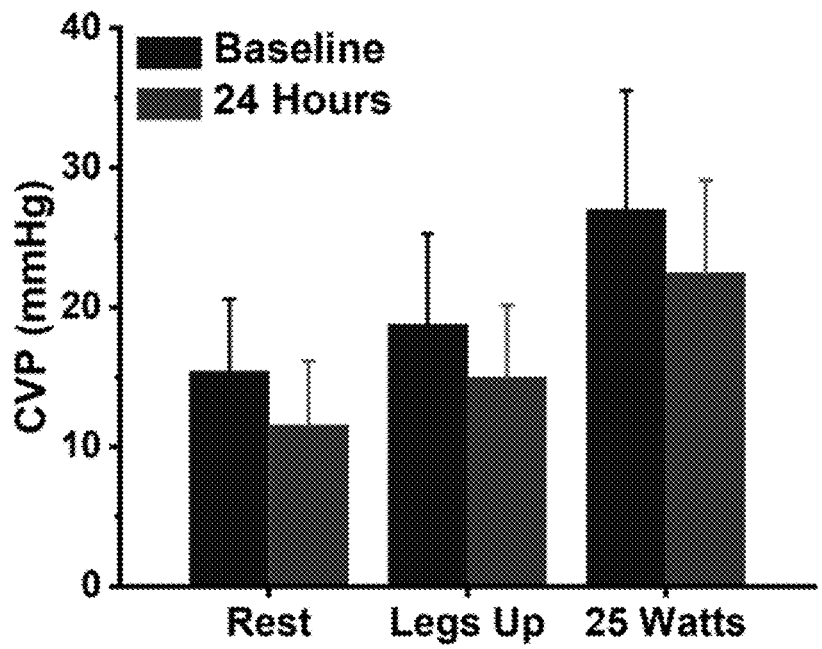
FIGS. 21A-21B: Baseline vs 24-hour Levosimendan Infusion—Impact on CVP and PCWP. All values differ between baseline and 24-hours LEVO infusion by paired t-test.
Figure 21B:
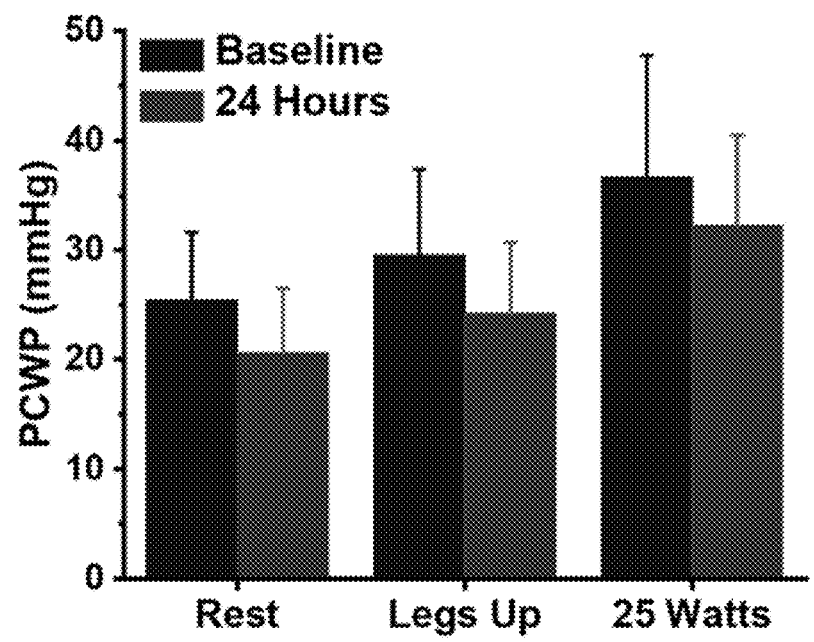
Figure 25:
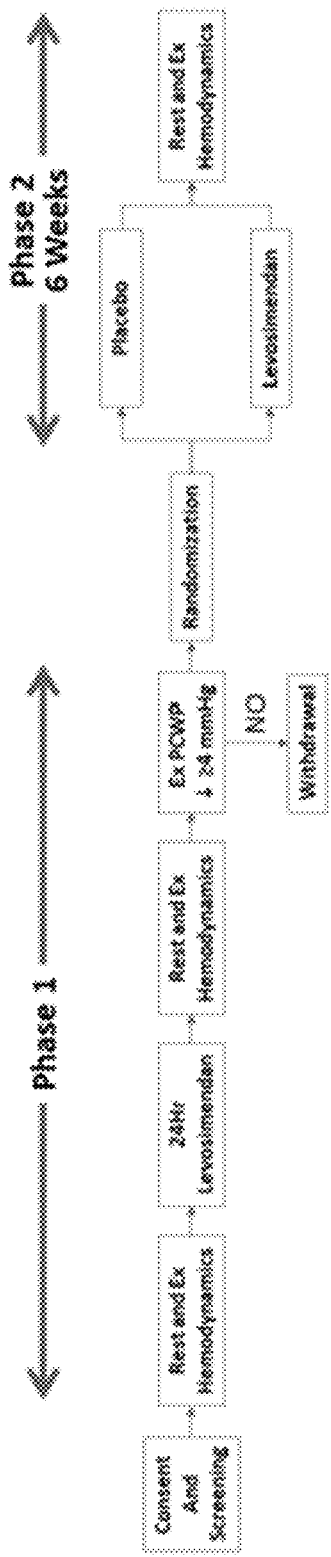
FIG. 25: Overview of two phase study, with an initial unblinded levosimendan infusion to identify levosimendan "responders" defined as a ≥4 mmHg reduction of pulmonary capillary wedge pressure (PCWP) during 25 Watt exercise (EX) followed by a subsequent randomized double blind phase.
Figure 26:
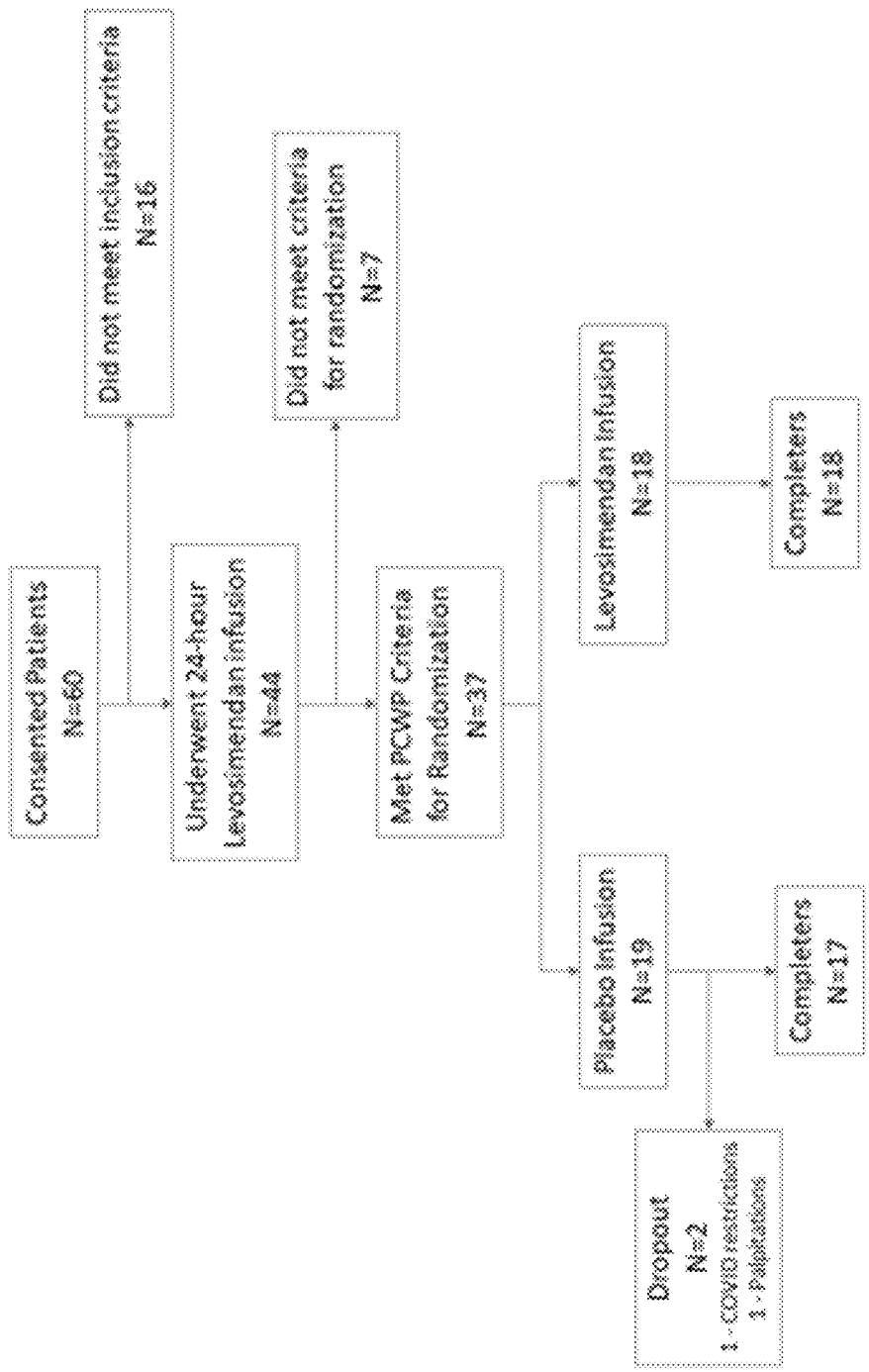
FIG. 26: CONSORT diagram showing flow a patients through entire study
Figure 27A:
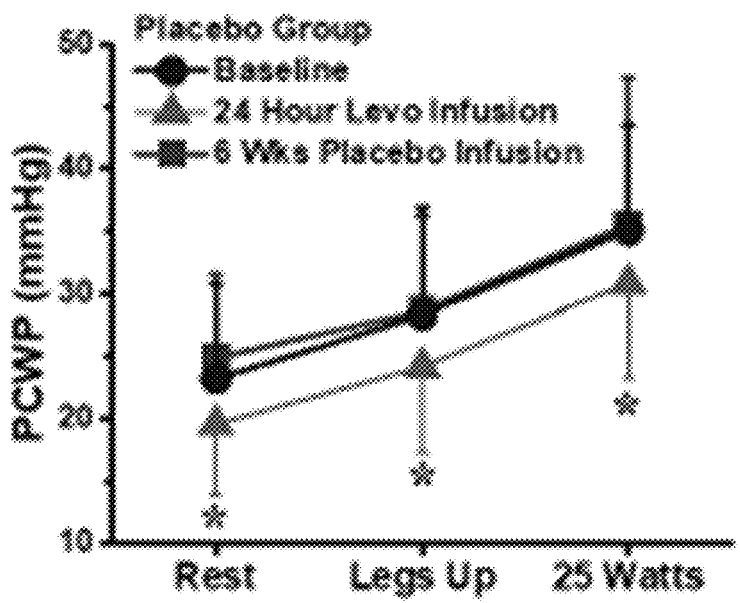
FIGS. 27A-27B: Comparison of pulmonary capillary wedge pressure (PCWP) and central venous pressure (CVP) between baseline, 24 hours and 6 weeks at rest, with legs up and during 25 Watts exercise. Placebo group shown in FIG. 27A and FIG. 27B; levosimendan group shown in FIG. 27C and FIG. 27D. *p<0.05 for comparison between respective baseline and 24-hour measurements.
Figure 27B:
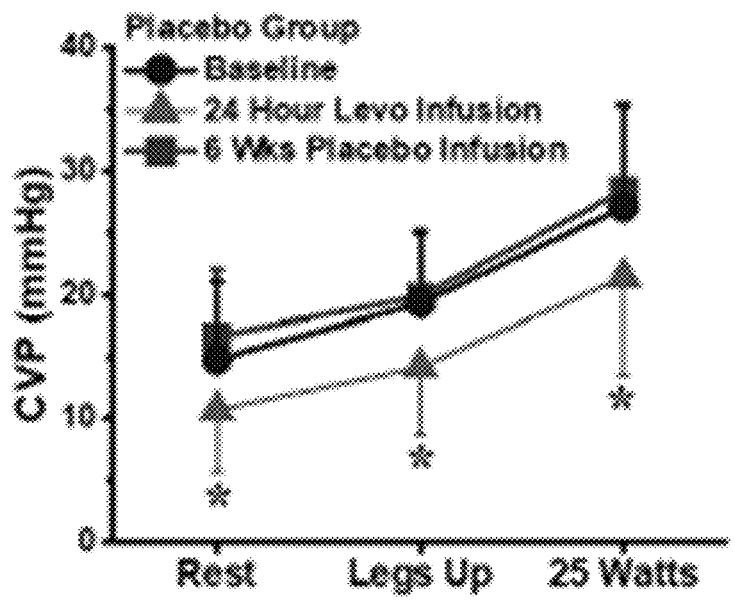
Figure 27C:
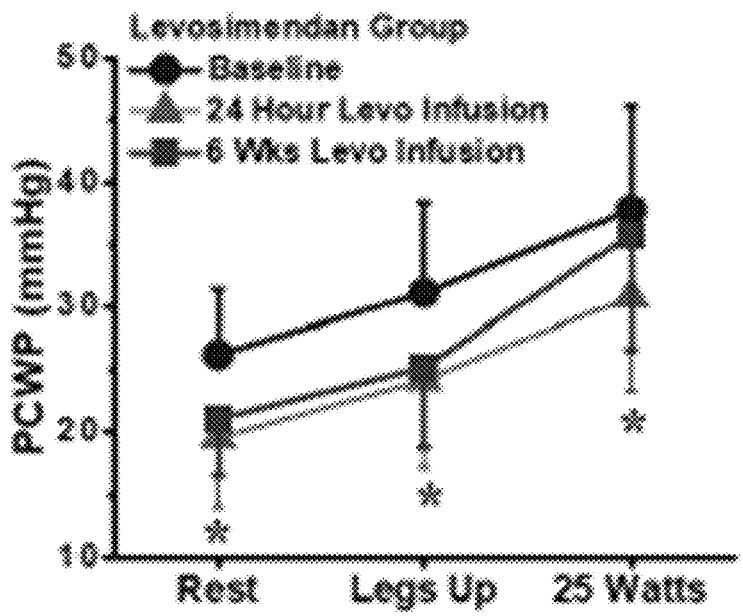
Figure 27D:
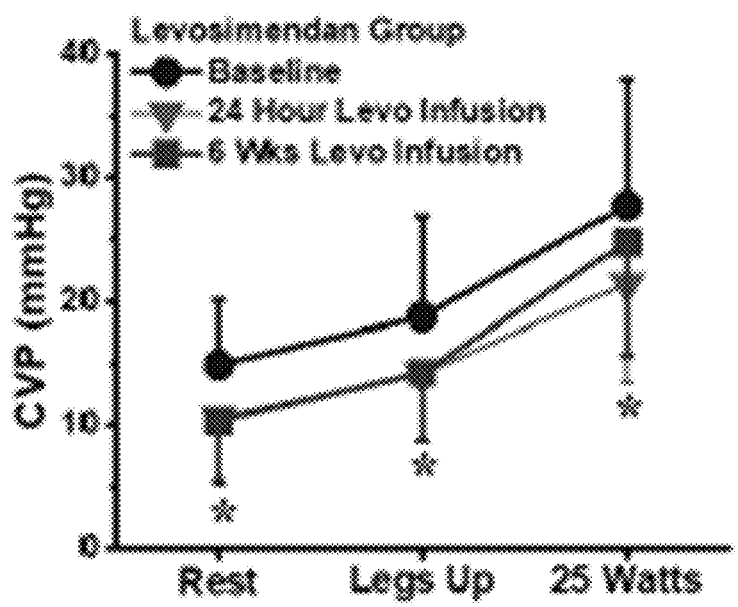
Figure 28A:
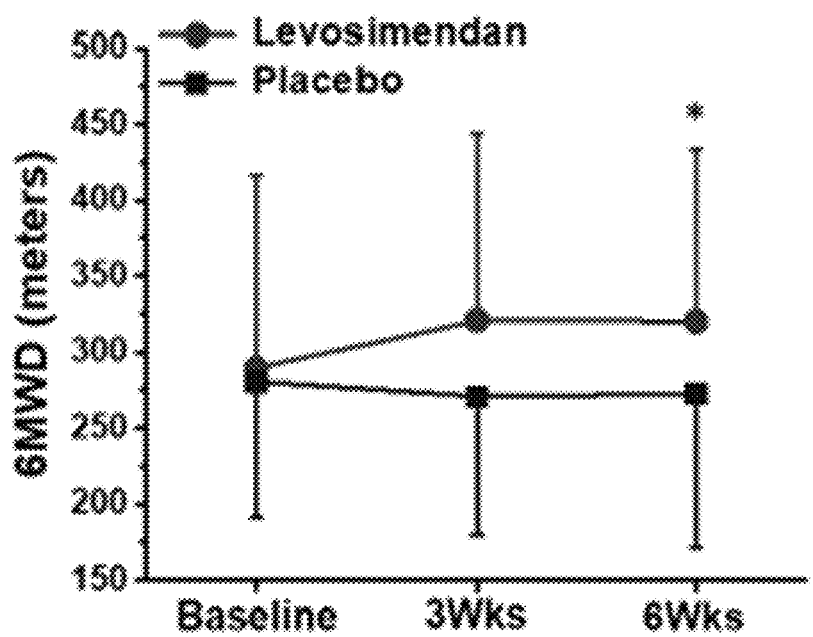
FIG. 28A: Comparison of 6 minute walk distance (6 MWD) in treatment and control groups.
Figure 28B:
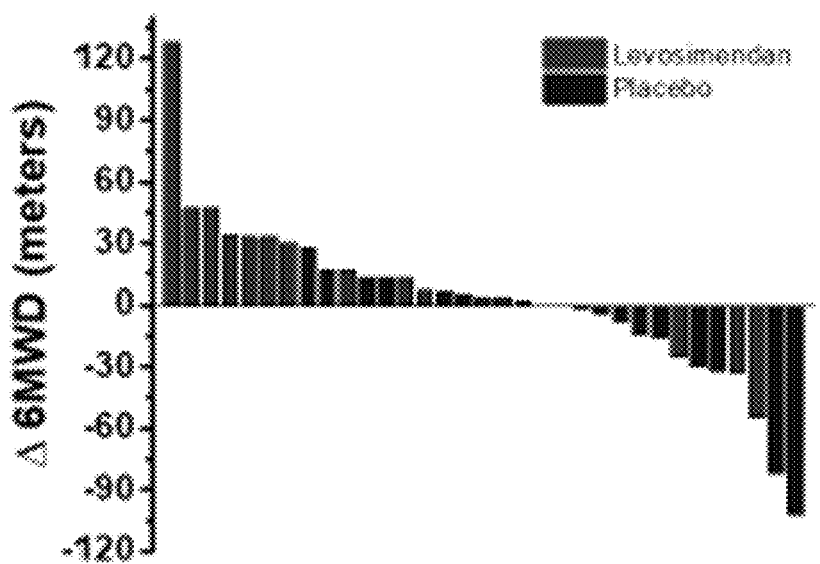
FIG. 28B: Rank ordered listing of changes in 6 MWD for each patient designated by group assignment. More patients in the treatment group had increased 6 MWD, whereas more patients in the control group had decreased 6 MWD. *p<0.05.

As reported herein, levosimendan is surprisingly found to provide effective treatment for a human subject afflicted with pulmonary hypertension and heart failure with preserved ejection fraction (PH-HFpEF). Levosimendan can improve cardiovascular hemodynamics, exercise capacity, and quality of life. The study showed evidence that the levosimendan infusion was able to reduce pulmonary capillary wedge pressure, right atrial pressure, and mean pulmonary arterial pressure. Additionally, levosimendan infusion was able to increase cardiac output, quality of life and 6-minute walk distance. The statistically significant improvement in 6-minute walk distance in levosimendan treated patients (FIG. 15) is particularly noteworthy as this is the first multicenter placebo controlled trial in HFpEF or PH-HFpEF patients to ever show that a pharmacologic agent can improve in 6 minute walk distance. Since the trial was not sized or designed to show a difference in 6 minute walk distance this was a very surprising finding.

Furthermore, levosimendan is also surprisingly found to be safe when administered in a non-hospital or non-clinical setting and when self-administered. Levosimendan treatment was provided in an outpatient setting, as well as in the human subject's home. Based on the results from the study, there is confirmation for the first time that home administration of levosimendan can be done safely in PH-HFpEF patients.

Additionally, levosimendan is also surprisingly found to be safe when given to PH-HFpEF patients in weekly 24-hour infusions. While other studies have evaluated intermittent dosing of levosimendan to treat HFrEF patients, none of these studies have evaluated weekly 24-hour infusions of levosimendan. Most of these other studies evaluated infusions every 2, 3, 4 weeks with infusion durations of only 6-12 hours.

Results presented herein also show that we have discovered a means of identifying PH-HFpEF patients who have a high likelihood of responding to levosimendan, i.e. a means of identifying PH-HFpEF responders to levosimendan. The relative increase in patient's stroke volume observed at 25 watts of exercise, compared to at rest, is a strong predictor of a patient's response. Without being bound to any mechanistic theory, this indicator may identify whether a patient has adequate cardiac reserve needed to respond to levosimendan therapy.

These aforementioned surprising results are the first of their kind seen in PH-HFpEF patients and are even more surprising when viewed in light of the extremely high failure rate of previous trials.

REFERENCES

Banfor, P. N., et al. (2008). Comparative effects of levosimendan, OR-1896, OR-1855, dobutamine, and milrinone on vascular resistance, indexes of cardiac function, and O2 consumption in dogs. American Journal of Physiology—Heart and Circulatory Physiology, 294(1), H238-H248.

Bittner, B., et al. (2018). Subcutaneous administration of biotherapeutics: an overview of current challenges and opportunities. BioDrugs, 32(5), 425-440.

Borlaug et al. Levosimendan Improves Hemodynamics And Submaximal Exercise Capacity In PH-HFpEF: Primary Results from the Help-PH-HFpEF Multicenter Randomized Controlled Trial Heart Society of America—Late Breaking Clinical Trials Session, Oct. 3, 2020 4:30 PM-5:30 PM.

Burkhoff et al. "24-hour Levosimendan Infusion Decreases Biventricular Filling Pressures and Increases Cardiac Output at Rest and Exercise in PH-HFpEF." Circulation 142.Suppl_3 (2020): A15294-A15294.

Chrusciel, P., et al. (2014) Defining the role of trimetazidine in the treatment of cardiovascular disorders: some insights on its role in heart failure and peripheral artery disease. Drug, 74(9) 971-980.

De Luca, L., et al. (2006). Effects of levosimendan on left ventricular diastolic function after primary angioplasty for acute anterior myocardial infarction: a Doppler echocardiographic study. Journal of the American Society of Echocardiography, 19(2), 172-177.

Dixon, D. D., et al. (2015). Combined post- and pre-capillary pulmonary hypertension in heart failure with preserved ejection fraction. Heart failure reviews, 21(3), 285-297.

Du Toit, E. F., et al. (2008). A role for the RISK pathway and KATP channels m pre- and post-conditioning induced by levosimendan n the isolated guinea pig heart. British journal of pharmacology, 154(1), 41-50

ElGuindy, A., et al. (2012). Heart failure with preserved ejection fraction. Global Cardiology Science and Practice, 2012(1), 10.

Erdei, N., et al. (2006). The levosimendan metabolite OR-1896 elicits vasodilation by activating the KATP and BKCa channels in rat isolated arterioles. British journal of pharmacology, 148(5), 696-702.

Galie, N., et al. (2009). Guidelines for the diagnosis and treatment of pulmonary hypertension: the Task Force for the Diagnosis and Treatment of Pulmonary Hypertension of the European Society of Cardiology (ESC) and the European Respiratory Society (ERS), endorsed by the International Society of Heart and Lung Transplantation (ISHLT). European heart journal, 30(20), 2493-2537

Gorter, T. M., et al. (2018). Right heart dysfunction and failure in heart failure with preserved ejection fraction: mechanisms and management. Position statement on behalf of the Heart Failure Association of the European Society of Cardiology. European journal of heart failure. 20(1), 16-37.

Grossini, E., et al. (2005). Hemodynamic effect of intracoronary administration of levosimendan in the anesthetized pig. Journal of cardiovascular pharmacology, 46(3), 333-342.

Haikala, H., et al. (1995). Mechanisms of action of calcium-sensitizing drugs. Journal of cardiovascular pharmacology. 26. S10-9.

Hajjar, R. J., et al. (1991). Calcium-sensitizing inotropic agents in the treatment of heart failure: a critical view. Cardiovascular drugs and therapy 5(6), 961-965.

Hasenfuss, G., et al. (1998). Influence of the novel inotropic agent levosimendan on isometric tension and calcium cycling in failing human myocardium. Circulation, 98(20), 2141-2147.

Hawthorne, K. M., et al. (2012). Quality assessment in dobutamine stress echocardiography: what are the clinical predictors associated with a non-diagnostic test?. Cardiology research, 3(2), 73.

Hoeper, M. M., et al. (2016). A global view of pulmonary hypertension. The Lancet Respiratory Medicine, 4(4), 306-322.

Jiang, R., et al. (2018). Efficacy and safety of a calcium sensitizer, levosimendan, in patients with right heart failure due to pulmonary hypertension. The clinical respiratory journal, 12(4), 1518-1525.

Kheinen, P., et al. (2001). Levosimendan increases diastolic coronary flow in isolated guinea-pig heart by opening ATP-sensitive potassium channels. Journal of cardiovascular pharmacology, 37(4), 367-374.

Kelly, J. P., et al. (2015) Patient selection in heart failure with preserved ejection fraction clinical trials. Journal of the American College of Cardiology. 65(16), 1668-1682.

Kivikko, M., et al. (2002). Pharmacodynamics and safety of a new calcium sensitizer, levosimendan, and its metabolites during an extended infusion in patients with severe heart failure. The Journal of Clinical Pharmacology, 42(1), 43-51.

Kivikko, M., et al. (2003). Sustained hemodynamic effects of intravenous levosimendan. Circulation. 107(1), 81-86.

Klapholz, M., et al. (2004). Hospitalization for heart failure in the presence of a normal left ventricular ejection fraction: results of the New York Heart Failure Registry. Journal of the American College of Cardiology, 43(8), 1432-1438.

Kleber, F. X., et al. (2009). Repetitive dosing of intravenous levosimendan improves pulmonary hemodynamics in patients with pulmonary hypertension: results of a pilot study. The Journal of Clinical Pharmacology, 49(1), 109-115.

Kostis, J. B., et al. (2004). Omapatrilat and enalapril in patients with hypertension: the Omapatrilat Cardiovascular Treatment vs. Enalapril (OCTAVE) trial. American journal of hypertension, 17(2), 103-111.

Lai, Y. C., et al. (2019). Insights into the pulmonary vascular complications of heart failure with preserved ejection fraction. The Journal of physiology, 597(4), 1143-1156.

Laurent, S., et al. (2000). Antihypertensive effects of fasidotril, a dual inhibitor of neprilysin and angiotensin-converting enzyme, in rats and humans. Hypertension, 35(5), 1148-1153.

Levine, A. R., et al. (2019). Pulmonary vascular disease in the setting of heart failure with preserved ejection fraction. Trends in cardiovascular medicine, 29(4), 207-217.

Louhelainen, M., et al. (2009). Effects of calcium sensitizer OR-1986 on cardiovascular mortality and myocardial remodelling in hypertensive Dahl/Rapp rats. Acta physiologica Polonica, 12(3), 41.

Louhelainen, M., et al. (2010). Effects of the calcium sensitizer OR-1896, a metabolite of levosimendan, on post-infarct heart failure and cardiac remodelling in diabetic Goto-Kakizaki rats. British journal of pharmacology. 160(1), 142-152.

Maytin, M., et al. (2005). Cardioprotection: a new paradigm in the management of acute heart failure syndromes. The American journal of cardiology 96(6), 26-31.

McLaughlin, V. V., et al. (2009). ACCF/AHA 2009 expert consensus document on pulmonary hypertension: a report of the American College of Cardiology Foundation Task Force on expert consensus documents and the American Heart Association developed in collaboration with the American College of Chest Physicians; American Thoracic Society, Inc.; and the Pulmonary Hypertension Association. Journal of the American College of Cardiology, 53(17), 1573-1619.

Michaels, A. D., et al. (2005). Effects of intravenous levosimendan on human coronary vasomotor regulation, left ventricular wall stress, and myocardial oxygen uptake. Circulation, 111(12), 1504-1509.

Northridge, D. B., et al. (1999). Comparison of the short-term effects of candoxatril, an orally active neutral endopeptidase inhibitor, and frusemide in the treatment of patients with chronic heart failure. *American heart journal,* 138(6), 1149-1157.

Norton, G. R., et al (1999). Sustained Antihypertensive Actions of a Dual Angiotensin-Converting Enzyme Neutral Endopeptidase Inhibitor. Sampatrilat, in Black Hypertensive Subjects. *American journal of hypertension,* 12(6), 563-571.

Oktay, A. A., et al. (2013). The emerging epidemic of heart failure with preserved ejection fraction. *Current heart failure reports,* 10(4), 401-410.

Oldroyd, S. H., et al. (2019). Pulmonary Hypertension.

Oudiz, R. J., et al. (2007). Pulmonary hypertension associated with left-sided heart disease. *Clinics in chest medicine,* 28(1), 233-241

Opitz, Christian F., et al. (2016). Pre-capillary, combined, and post-capillary pulmonary hypertension: a pathophysiological continuum. *Journal of the American College of Cardiology* 68.4: 368-378.

Pataricza, J., et al. (2000). Comparison of the vasorelaxing effect of cromakalim and the new inodilator, levosimendan, in human isolated portal vein. *Journal of pharmacy and pharmacology,* 52(2), 213-217.

Peacock, A. J., et al. (2004). *Pulmonary Circulation: Diseases and Their Treatment.* CRC Press.

Pollesello, P., et al. (1994). Binding of a new Ca2+ sensitizer, levosimendan, to recombinant human cardiac troponin C. A molecular modelling, fluorescence probe, and proton nuclear magnetic resonance study. *Journal of Biological Chemistry,* 269(46), 28584-28590.

Pollesello, P., et al. (2007). The cardioprotective effects of levosimendan: preclinical and clinical evidence. *Journal of cardiovascular pharmacology.* 50(3), 257-263.

Segreti, J. A., et al. (2008). Evoked changes in cardiovascular function in rats by infusion of levosimendan, OR-1896 [(R)—N-(4-(4-methyl-6-oxo-1, 4, 5, 6-tetrahydropyridazin-3-yl) phenyl) acetamide], OR-1855 [(R)-6-(4-aminophenyl)-5-methyl-4, 5-dihydropyridazin-3 (2H)-one], dobutamine, and milrinone: comparative effects on peripheral resistance, cardiac output, dP/dt, pulse rate, and blood pressure. *Journal of Pharmacology and Experimental Therapeutics,* 325(1), 331-340.

Shaw, S. J., et al. (2016). Phenotype-specific treatment of heart failure with preserved ejection fraction: a multiorgan roadmap. *Circulation,* 134(1), 73-90.

Simonneau, G., et al. (2009). Updated clinical classification of pulmonary hypertension. *Journal of the American College of Cardiology,* 54 (1 Supplement), S43-S54.

Sorsa, T., et al. (2004). The contractile apparatus as a target for drugs against heart failure: interaction of levosimendan, a calcium sensitiser, with cardiac troponin c. *Molecular and cellular biochemistry,* 266(1-2), 87-107.

Szilagyi, S., et al. (2004). The effects of levosimendan and OR-1896 on isolated hearts, myocyte-sized preparations and phosphodiesterase enzymes of the guinea pig. *European journal of pharmacology,* 486(1), 67-74.

Teerlink, J. R., et al. (2016). RELAX-REPEAT: a multicenter, prospective, randomized, double-blind study evaluating the safety and tolerability of repeat doses of serelaxin in patients with chronic heart failure. *Journal of Cardiac Failure,* 22(8), S14-S15.

Torres, F., et al. (2019). Efficacy and safety of ralinepag, a novel oral IP agonist, in PAH patients on mono or dual background therapy: results from a phase 2 randomised, parallel group, placebo-controlled trial. *European Respiratory Journal,* 54(4).

Vandoni, M., et al. (2018). Six minute walk distance and reference values in healthy Italian children: A cross-sectional study. *PloS one,* 13(10).

Virgadamo, S., et al. (2015). Digoxin: A systematic review in atrial fibrillation, congestive heart failure and post myocardial infarction. *World journal of cardiology,* 7(11), 808.

Wait, J. C., et al. (2006). Metabolism of [14C] gemopatrilat after oral administration to rats, dogs, and humans. *Drug metabolism and disposition,* 34(6), 961-970.

Yancy, C. W., et al. (2013), 2013 ACCF/AHA guideline for the management of heart failure: a report of the American College of Cardiology Foundation/American Heart Association Task Force on Practice Guidelines. *Journal of the American College of Cardiology,* 62(16), e147-e239.

Yancy, C. W., et al. (2013). 2013 ACCF/AHA guideline for the management of heart failure: executive summary: a report of the American College of Cardiology Foundation/American Heart Association Task Force on Practice Guidelines. *Circulation,* 128(16), 1810-1852.

Yokoshiki, H., et al. (1997). Levosimendan, a novel Ca2+ sensitizer, activates the glibenclamide-sensitive K+ channel in rat arterial myocytes. *European journal of pharmacology,* 333(2-3), 249-259.

What is claimed is:

1. A method for improving exercise capacity as measured by an at least 5 meter increase in the six (6) minute walk distance in a human subject afflicted with Pulmonary Hypertension Heart Failure with preserved Ejection Fraction (PH-HFpEF) comprising intravenously, orally, or subcutaneously administering to the human subject an amount of levosimendan, its metabolites OR-1896 or OR-1855, or a combination thereof, so as to improve the human subject's exercise capacity by an at least 5 meter increase in the six (6) minute walk distance.

2. The method of claim 1, wherein the administering is via IV administration.

3. The method of claim 2, wherein the administering is given via a 24-hour infusion or the administering is chronic administration given via a less than 24-hour infusion.

4. The method of claim 1, wherein the administration is via oral dosing.

5. The method of claim 1, wherein the administration is subcutaneous administration of a subcutaneous formulation.

6. The method of claim 1, wherein the amount of levosimendan its metabolites OR-1896 or OR-1855, or a combination thereof, is administered in combination with a cardiovascular drug.

7. The method of claim 6, wherein the cardiovascular drug is a PDE inhibitor, a phosphodiesterase-5 (PDE5) inhibitor, an endothelin receptor antagonist (ERA), a prostanoid, a soluble guanylate cyclase stimulator, a nitrate, a nitrite, an NO donor, a calcium channel blocker (CCB), a fatty acid oxidation inhibitor, a beta-blocker (BB), an angiotensin-converting enzyme (ACE) inhibitor, a neprilysin inhibitor, a neprilysin and angiotensin receptor blocker (ANRI), an angiotensin II receptor blocker (ARB), a diuretic, an aldosterone antagonist, digoxin, ivabradine, hydralazine, seralaxin, a natriuretic peptide, an atrial natriueretic peptide (ANP), a natriuretic peptide, a K-ATP channel activator, a NEP inhibitor, or a prostacyclin.

8. The method of claim 6, wherein the cardiovascular drug is a pulmonary vasodilator drug and wherein the amount of levosimendan, its metabolites OR-1896 or OR-1855, or a combination thereof, administered in combination with the pulmonary vasodilator drug is administered to a human subject afflicted with pre and post capillary pulmonary hypertension and heart failure with preserved ejection fraction (Cpc-PH-HFpEF).

9. The method of claim 1, wherein the administering of the amount of levosimendan results in steady state blood levels of OR1896 in the range of 0.20 ng/mL to 25.00 ng/mL.

10. The method of claim 1, wherein the administering of the amount of levosimendan results in steady state blood levels of OR1896 in the range of 0.50 ng/mL to 10.00 ng/mL.

11. The method of claim 1, wherein the treating comprises improving exercise capacity as measured by an at least 5 meter increase in the six (6) minute walk distance of the human subject afflicted with PH-HFpEF.

12. The method of claim 1, wherein the method further improves the human subject's quality of life.

13. The method of claim 12, wherein the improvement in the human subject's quality of life is measured by a patient reported outcome assessment tool.

14. The method of claim 12, wherein the improvement in the human subject's quality of life is measured by a Likert scale that is a five (5) point patient reported outcome assessment tool.

15. The method of claim 12, wherein the improvement is a change in the human subject's patient reported outcome assessment tool score of at least 1.

16. The method of claim 12, wherein the improvement is a change in the human subject's patient reported outcome assessment tool score of at least 2.

17. The method of claim 4, wherein the oral dosing comprises an immediate release formulation or an extended-release formulation.

18. The method of claim 1, wherein the subject is orally administered between 1-4 mg of levosimendan, its metabolites OR-1896 or OR-1855, or a combination thereof, per day.

19. The method of claim 1, wherein no arrythmias, atrial or ventricular, are observed when comparing baseline electrocardiographic monitoring with 72-hour monitoring after 5 weeks of administration.

20. The method of claim 1, wherein the administering presents no more statistically significant serious adverse events than the matching placebo.

* * * * *